US011884983B2

(12) United States Patent
Santi et al.

(10) Patent No.: US 11,884,983 B2
(45) Date of Patent: Jan. 30, 2024

(54) METHOD FOR PREDICTING RESISTANCE

(71) Applicant: Aqua Gen AS, Trondheim (NO)

(72) Inventors: Nina Santi, Trondheim (NO); Thomas Moen, Ås (NO); Jørgen Ødegård, Sande I Vestfold (NO)

(73) Assignee: Aqua Gen AS, Trondheim (NO)

( * ) Notice: Subject to any disclaimer, the term of this patent is extended or adjusted under 35 U.S.C. 154(b) by 0 days.

(21) Appl. No.: 15/527,592

(22) PCT Filed: Nov. 18, 2015

(86) PCT No.: PCT/NO2015/050218
§ 371 (c)(1),
(2) Date: May 17, 2017

(87) PCT Pub. No.: WO2016/080844
PCT Pub. Date: May 26, 2016

(65) Prior Publication Data
US 2019/0241980 A1   Aug. 8, 2019

(30) Foreign Application Priority Data

Nov. 18, 2014  (NO) .................................. 20141382

(51) Int. Cl.
*C12Q 1/6888*   (2018.01)
(52) U.S. Cl.
CPC ..... *C12Q 1/6888* (2013.01); *C12Q 2600/124* (2013.01); *C12Q 2600/156* (2013.01)
(58) Field of Classification Search
None
See application file for complete search history.

(56) References Cited

FOREIGN PATENT DOCUMENTS

WO    WO 2014/006428    1/2014

OTHER PUBLICATIONS

Ozaki et al. Mol. Genet. Genomics (2001)265:23-31 (Year: 2001).*
Berthelot et al. (Nature Communications, vol. 5; 3657; doi: 10.1038, Apr. 22, 2014) (Year: 2014).*
GenBank FR904293.1. (May 27, 2014) (Year: 2014).*
Palit et la. Molecular Ecology Resources, Oct. 8, 2014 (Year: 2014).*
Kalinowski et al. (Molecular Ecology Resources, doi:10.1111/j.1755-0998.2010.02932.x., 2010) (Year: 2010).*
Sanchez, BMC Genomics, vol. 10, No. 559, 2009 (Year: 2009).*
Palti et al. Molecular Ecology Resources, Oct. 2014, pp. 662-672 (Year: 2014).*
Colussi et al., Association of a specific major histocompatibility complex class IIβ single nucleotide polymorphism with resistance to lactococcosis in rainbow trout, Oncorhynchus mykiss (Walbaum), 38 Journal of Fish Diseases 27-35 (2015).
Gheyas et al., Segregation of infectious pancreatic necrosis resistance QTL in the early life cycle of Atlantic Salmon (Salmo salar), 41 Animal Genetics 531-536 (2010).
Houston et al., Characterisation of QTL-linked and genome-wide restriction site-associated DNA (RAD) markers in farmed Atlantic salmon, 13(244) BMC Genomics 1-15 (2012).
Lo et al., Altered gene expression patterns of innate and adaptive immunity pathways in transgenic rainbow trout harboring Cecropin P1 transgene, 15(887) BMC Genomics 1-13 (2014).
Moen et al., Confirmation and fine-mapping of a major QTL for resistance to infection pancreatic necrosis in Atlantic salmon (Salmo salar): population-level associations between markers and trait, 10(368) BMC Genomics 1-14 (2009).
Moen et al., Breeding for Resistance to Viral Diseases in Salmonids, Breeding for Disease Resistance in Farm Animals 166-179 (2011).
Ozaki et al., Quantitative trait loci (QTLs) associated with resistance/susceptibility to infectious pancreatic necrosis virus (IPNV) in rainbow trout (Oncorhynchus mykiss), 265 Mol Genet Genomics 23-31 (2001).
Ozaki et al., Identification of Additional Quantitative Trait Loci (QTL) responsible for Susceptibility to Infectious Pancreatic Necros Virus in Rainbow Trout, 42(3) Fish Pathology 131-140 (2007).
Vallejo et al., Detection of QTL in Rainbow Trout Affecting Survival When Challenged with Flavobacterium psychrophilum, 16 Mar Biotechnol 349-360 (2014).

* cited by examiner

Primary Examiner — Jeanine A Goldberg
(74) Attorney, Agent, or Firm — Panitch Schwarze Belisario & Nadel LLP; Erin M. Dunston

(57) ABSTRACT

The present invention relates generally to single nucleotide polymorphisms (SNP) associated with increased resistance of a rainbow trout (*Oncorhynchus mykiss*) to infectious pancreatic necrosis (IPN). In particular, the present invention provides methods for predicting increased resistance of a rainbow trout to infectious pancreatic necrosis (IPN) and methods for selecting a rainbow trout having increased resistant to infectious pancreatic necrosis. The present invention further provides rainbow trout, rainbow trout cells and populations thereof carrying at least one allele conferring IPN resistance ("IPN resistance allele") in their genome as well as nucleic acid molecules comprising nucleotide sequences associated with the SNPs of the present invention.

10 Claims, 3 Drawing Sheets
Specification includes a Sequence Listing.

METHOD FOR PREDICTING RESISTANCE

CROSS-REFERENCE TO RELATED APPLICATIONS

This application is a U.S. National Stage Application pursuant to 35 U.S.C. § 371 of International Patent Application PCT/NO2015/050218, filed on Nov. 18, 2015, and published as WO 2016/080844 on May 26, 2016, which claims priority to Norway Patent Application 20141382, filed on Nov. 18, 2014, all of which are incorporated herein by reference in their entireties for all purposes.

FIELD OF THE INVENTION

The present invention relates generally to polymorphisms, and in particular single nucleotide polymorphisms (SNP), associated with increased resistance of a rainbow trout (*Oncorhynchus mykiss*) to infectious pancreatic necrosis (IPN). In particular, the present invention provides methods for predicting increased resistance of a rainbow trout to infectious pancreatic necrosis (IPN) and methods for selecting a rainbow trout having increased resistant to infectious pancreatic necrosis. The present invention further provides rainbow trout, rainbow trout cells and populations thereof carrying at least one allele, such as at least two alleles, conferring IPN resistance ("IPN resistance allele") in their genome as well as nucleic acid molecules comprising nucleotide sequences associated with the SNPs of the present invention.

BACKGROUND OF THE INVENTION

Infectious Pancreatic Necrosis (IPN) is a viral disease causing large mortalities in the farming of rainbow trout, in Norway and internationally. The disease is caused by the IPN virus (IPNV), classified as an aquatic biRNA virus, causing necrosis of pancreatic cells and liver cells, resulting in lethargy and sudden mortality.

Breeding companies like AquaGen AS have run continuous fish selection programs aimed at improving the aquaculture stocks with regards to disease resistance and protocols have been developed for testing the fish's resistance to several specific diseases. These challenge tests have been used in order to select fish as broodstock that possess above-average resistance to the diseases in question. Conventional tests involve controlled challenge-testing of siblings of the breeding candidates. This methodology is, however, impeded by the fact that infected fish cannot be used as broodstock (parents of the next generation). One therefore has to resort to selecting random (un-tested) animals from the families of the tested fish that performed best in the challenge test (so-called family selection).

There is therefore a need for improved methodologies for assessing the resistance of rainbow trout to Infectious Pancreatic Necrosis (IPN), particularly methodologies that allow the direct assaying and selection of individual's resistant to IPN, while retaining the possibility of using the tested fish as broodstock.

SUMMARY OF THE INVENTION

The present inventors have solved this need by having identified polymorphism, and in particular single nucleotide polymorphisms (SNP), within the genome, and more particularly on chromosome 1, of rainbow trout which are associated with increased resistance of the fish to infectious pancreatic necrosis (IPN).

The present invention provides in a first aspect a method for predicting increased resistance of a rainbow trout (*Oncorhynchus mykiss*) to infectious pancreatic necrosis (IPN). Particularly, the present invention provides a method for predicting increased resistance of a rainbow trout (*Oncorhynchus mykiss*) to infectious pancreatic necrosis (IPN), the method comprises:
  determining the presence of at least one (such as at least two) allele conferring IPN resistance ("IPN resistance allele") within the genome (e.g. on chromosome 1 of the genome) of said rainbow trout.

According to certain embodiments, the present invention provides a method for predicting increased resistance of a rainbow trout (*Oncorhynchus mykiss*) to infectious pancreatic necrosis (IPN), the method comprises:
  determining the identity of a nucleotide of at least one allele, optionally of at least two alleles, of at least one single nucleotide polymorphism (SNP) associated with increased resistance to infectious pancreatic necrosis within the genome (e.g., on chromosome 1 of the genome) of said rainbow trout, said at least one SNP being located within said genome at a position corresponding to position 36 of the nucleotide sequence set forth in any one of SEQ ID NOs: 1 to 78 and SEQ ID NOs: 160 to 229, or at a position corresponding to position 36 of a nucleotide sequence which is derived from any one of SEQ ID NOs: 1 to 78 and SEQ ID NOs: 160 to 229 by 1 to 5, such as 1 to 2, nucleotide substitutions.

The rainbow trout has increased resistance to infectious pancreatic necrosis when the nucleotide of the at least one allele is a nucleotide corresponding to the IPN resistance allele of the respective SNP. The IPN resistance allele of each SNP is specified in Table 1.

According to certain other embodiments, the present invention provides a method for predicting increased resistance of a rainbow trout (*Oncorhynchus mykiss*) to infectious pancreatic necrosis (IPN), the method comprises:
  determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being selected from the group consisting of: AX-89929954, AX-89918280, AX-89938309, AX-89960828, AX-89930342, AX-89928530, AX-89949788, AX-89928131, AX-89949832, AX-89916790, AX-89973719, AX-89962023, AX-89921280, AX-89931666, AX-89921585, AX-89953905, AX-89952945, AX-89934682, AX-89951942, AX-89937020, AX-89924837, AX-89958601, AX-89923477, AX-89959350, AX-89929482, AX-89937712, AX-89949602, AX-89925103, AX-89938051, AX-89924174, AX-89936461, AX-89916703, AX-89935317, AX-89966423, AX-89933348, AX-89969315, AX-89919958, AX-89968417, AX-89946851, AX-89976917, AX-89945446, AX-89919457, AX-89973597, AX-89938138, AX-89971866, AX-89958882, AX-89961273, AX-89944901, AX-89919465, AX-89959425, AX-89917102, AX-89959281, AX-89916766, AX-89920507, AX-89957370, AX-89934009, AX-89929663, AX-89952300, AX-89916572, AX-89946911, AX-89974593, AX-89927158, AX-89970383, AX-89965404, AX-89955634, AX-89932926, AX-89941493, AX-89943031, AX-89957682, AX-89960611, AX-89950199, AX-89928407, AX-89962035, AX-89931951, AX-89976536, AX-89916801, AX-89929085, AX-89925267, chr1_7515539, chr1_7108873, chr1_6864558, chr1_7186663, chr1_6730531, chr1_27891953, AX_89953259, chr1_6740481, chr1_6770611, chr1_7412807, chr1_7360179, chr1_7411803, chr1_7431445, chr1_7433199, chr1_7441254, chr1_7441877, chr1_7533570, chr1_6834898, chr1_6730142, chr1_6746052, chr1_6794061, chr1_7399212, chr1_7442637, chr1_7358019, chr1_7709828, chr1_7598090, chr1_7626471, chr1_7598743, chr1_7670293, chr1_7670561, chr1_7647634, chr1_7356089, chr1_8109044, chr1_10439048, chr1_8142346, chr1_8092208, chr1_8138683, chr1_8139206, chr1_8139744, chr1_8140789, chr1_8141687, chr1_8154917, chr1_7454708, chr1_7504847, chr1_7505686, chr1_7505817, chr1_8202031, chr1_8228173, chr1_8309469, chr1_8163977, chr1_27786931, chr1_8194629, chr1_7505259, chr1_8474659, chr1_8282602, chr1_8306806, chr1_8341618, chr1_8343786, chr1_8345836, chr1_8350569, chr1_8402403, AX 89962103, chr1_8279302, chr1_8334901, chr1_7561600, AX_89956272, chr1_7938827, chr1_10810229, chr1_11007071 and chr1_10884171.

The rainbow trout has increased resistance to infectious pancreatic necrosis when the nucleotide of the at least one allele is a nucleotide corresponding to the IPN resistance allele of the respective SNP. The IPN resistance allele of each SNP is specified in Table 1.

The present invention provides in a further aspect a method for selecting a rainbow trout having increased resistance to infectious pancreatic necrosis. Particularly, the present invention provides a method for selecting a rainbow trout having increased resistance to infectious pancreatic necrosis, the method comprises:

determining the presence of at least one allele conferring IPN resistance ("IPN resistance allele") within the genome (e.g., on chromosome 1) of the genome) of said rainbow trout; and selecting said rainbow trout as having increased resistance when the at least one IPN resistance allele is present.

According to particular embodiments, the present invention provides a method for selecting a rainbow trout having increased resistance to infectious pancreatic necrosis, the method comprises:

determining the identity of a nucleotide of at least one allele, optionally of at least two alleles, of at least one single nucleotide polymorphism (SNP) associated with increased resistance to infectious pancreatic necrosis within the genome (e.g., on chromosome 1 of the genome) of said rainbow trout, said at least one SNP being located within said genome at a position corresponding to position 36 of the nucleotide sequence set forth in any one of SEQ ID NOs: 1 to 78 and SEQ ID NOs: 160 to 229, or at a position corresponding to position 36 of a nucleotide sequence which is derived from any one of SEQ ID NOs: 1 to 78 and SEQ ID NOs: 160 to 229 by 1 to 5, such as 1 to 2, nucleotide substitutions; and selecting said rainbow trout as having increased resistance when the nucleotide of the at least one allele is a nucleotide corresponding to the IPN resistance allele of the respective SNP. The IPN resistance allele of each SNP is specified in Table 1.

According to other particular embodiments, the present invention provides a method for selecting a rainbow trout having increased resistance to infectious pancreatic necrosis, the method comprises:

determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being selected from the group consisting of: AX-89929954, AX-89918280, AX-89938309, AX-89960828, AX-89930342, AX-89928530, AX-89949788, AX-89928131, AX-89949832, AX-89916790, AX-89973719, AX-89962023, AX-89921280, AX-89931666, AX-89921585, AX-89953905, AX-89952945, AX-89934682, AX-89951942, AX-89937020, AX-89924837, AX-89958601, AX-89923477, AX-89959350, AX-89929482, AX-89937712, AX-89949602, AX-89925103, AX-89938051, AX-89924174, AX-89936461, AX-89916703, AX-89935317, AX-89966423, AX-89933348, AX-89969315, AX-89919958, AX-89968417, AX-89946851, AX-89976917, AX-89945446, AX-89919457, AX-89973597, AX-89938138, AX-89971866, AX-89958882, AX-89961273, AX-89944901, AX-89919465, AX-89959425, AX-89917102, AX-89959281, AX-89916766, AX-89920507, AX-89957370, AX-89934009, AX-89929663, AX-89952300, AX-89916572, AX-89946911, AX-89974593, AX-89927158, AX-89970383, AX-89965404, AX-89955634, AX-89932926, AX-89941493, AX-89943031, AX-89957682, AX-89960611, AX-89950199, AX-89928407, AX-89962035, AX-89931951, AX-89976536, AX-89916801, AX-89929085, AX-89925267, chr1-7515539, chr1-7108873, chr1-6864558, chr1-7186663, chr1-6730531, chr1-27891953, AX-89953259, chr1-6740481, chr1-6770611, chr1-7412807, chr1-7360179, chr1-7411803, chr1-7431445, chr1-7433199, chr1-7441254, chr1-7441877, chr1-7533570, chr1-6834898, chr1-6730142, chr1_6746052, chr1-6794061, chr1-7399212, chr1-7442637, chr1-7358019, chr1-7709828, chr1-7598090, chr1-7626471, chr1-7598743, chr1-7670293, chr1-7670561, chr1-7647634, chr1-7356089, chr1-8109044, chr1-10439048, chr1-8142346, chr1-8092208, chr1-8138683, chr1-8139206, chr1-8139744, chr1-8140789, chr1-8141687, chr1-8154917, chr1-7454708, chr1-7504847, chr1-7505686, chr1-7505817, chr1-8202031, chr1-8228173, chr1-8309469, chr1-8163977, chr1-27786931, chr1-8194629, chr1-7505259, chr1-8474659, chr1-8282602, chr1-8306806, chr1-8341618, chr1-8343786, chr1-8345836, chr1-8350569, chr1-8402403, AX-89962103, chr1-8279302, chr1-8334901, chr1-7561600, AX-89956272, chr1-7938827, chr1-10810229, chr1-11007071 and chr1-10884171 and selecting said rainbow trout as having increased resistance when the nucleotide of the at least one allele is a nucleotide corresponding to the IPN resistance allele of the respective SNP. The IPN resistance allele of each SNP is specified in Table 1.

The present invention provides in a further aspect a rainbow trout, such as an isolated rainbow trout, having increased resistance to infectious pancreatic necrosis. Particularly, the present invention provides a rainbow trout or progeny thereof comprising within its genome (e.g., on chromosome 1 of its genome) at least one allele conferring IPN resistance ("IPN resistance allele").

According to certain embodiments, the present invention provides a rainbow trout or progeny thereof, such as an isolated rainbow trout or progeny thereof, which comprises within its genome (e.g., on chromosome 1 of its genome) at least one nucleotide sequence selected from the group consisting of a) the nucleotide sequences set forth in SEQ ID NOs: 79 to 156 and 230 to 299, and b) nucleotide sequences derived from any one of SEQ ID NOs: 79 to 156 and 230 to 299 by 1 to 5, such as 1 to 2, nucleotide substitutions, provide that said nucleotide substitutions are not at position 36 of said derived sequence.

The present invention provides in a further aspect a rainbow trout or progeny thereof which comprises in its genome at least one allele conferring IPN resistance obtainable by a process comprising the steps of:
genotyping the trout, selecting individuals having at least one allele preferably two alleles conferring IPN resistance ("IPN resistance allele"); and mating individuals in such a way that at least one individual within each mated pair has two alleles conferring IPN resistance.

According to certain embodiments the rainbow trout or progeny thereof obtained by the process, the at least one IPN resistance allele may be an allele of at least one single nucleotide polymorphism (SNP). Further the at least one SNP is selected from the SNPs listed in Table 1. Further the rainbow trout or progeny thereof may comprise within its genome at least one nucleotide sequence selected from the group consisting of a) the nucleotide sequences set forth in SEQ ID NOs: 79 to 156 and 230 to 299 and b) nucleotide sequences derived from any one of SEQ ID NOs: 79 to 156 and 230 to 299 by 1 to 5, such as 1 to 2, nucleotide substitutions, provided that said nucleotide substitutions are not at position 36 of said derived sequence.

The present invention provides in a further aspect a population of rainbow trout, such as an isolated population, each individual within the population having increased resistance to infectious pancreatic necrosis. Particularly, the present invention provides a population of rainbow trouts, each individual within the population comprising within its genome at least one allele conferring IPN resistance ("IPN resistance allele").

According to certain embodiments, the present invention provides a population of rainbow trout, such as an isolated population of rainbow trouts, each individual within the population comprising within its genome (e.g., on chromosome 1 of its genome) at least one nucleotide sequence selected from the group consisting of a) the nucleotide sequences set forth in SEQ ID NOs: 79 to 156 and 230 to 299, and b) nucleotide sequences derived from any one of SEQ ID NOs: 79 to 156 and 230 to 299 by 1 to 5, such as 1 to 2, nucleotide substitutions, provided that said nucleotide substitutions are not at position 36 of said derived sequence.

The present invention provides in a further aspect a rainbow trout population comprising in its genome at least one allele conferring IPN resistance obtainable by a process comprising the steps of:
genotyping the trout, selecting individuals having at least one allele preferably two alleles conferring IPN resistance ("IPN resistance allele"); and mating individuals in such a way that at least one individual within each mated pair has two alleles conferring IPN resistance According to certain embodiments the rainbow trout population obtained by the process, the at least one IPN resistance allele may be an allele of at least one single nucleotide polymorphism (SNP). Further the at least one SNP is selected from the SNPs listed in Table 1. Further the rainbow trout population may comprise within its genome at least one nucleotide sequence selected from the group consisting of a) the nucleotide sequences set forth in SEQ ID NOs: 79 to 156 and 230 to 299 and b) nucleotide sequences derived from any one of SEQ ID NOs: 79 to 156 and 230 to 299 by 1 to 5, such as 1 to 2, nucleotide substitutions, provided that said nucleotide substitutions are not at position 36 of said derived sequence.

The present invention provides in a further aspect a rainbow trout cell, such as an isolated rainbow trout cell, which comprises within its genome (e.g., on chromosome 1 of its genome) at least one allele conferring IPN resistance ("IPN resistance allele").

According to certain embodiments, the present invention provides a rainbow trout cell, such as an isolated rainbow trout cell, which comprises within its genome (e.g., on chromosome 1 of its genome) at least one nucleotide sequence selected from the group consisting of a) the nucleotide sequences set forth in SEQ ID NOs: 79 to 156 and 230 to 299, and b) nucleotide sequences derived from any one of SEQ ID NOs: 79 to 156 and 230 to 299 by 1 to 5, such as 1 to 2, nucleotide substitutions, provide that said nucleotide substitutions are not at position 36 of said derived sequence.

The present invention provides in a further aspect a population of rainbow trout cells, such as an isolated population of rainbow trout cells, each individual cell within the population comprising within its genome (e.g., on chromosome 1 of its genome) at least one allele conferring IPN resistance ("IPN resistance allele").

According to certain embodiments, the present invention provides a population of rainbow trout cells, such as an isolated population of rainbow trout cells, each individual cell within the population comprising within its genome (e.g., on chromosome 1 of its genome) at least one nucleotide sequence selected from the group consisting of a) the nucleotide sequences set forth in SEQ ID NOs: 79 to 156 and 230 to 299, and b) nucleotide sequences derived from any one of SEQ ID NOs: 79 to 156 and 230 to 299 by 1 to 5, such as 1 to 2, nucleotide substitutions, provide that said nucleotide substitutions are not at position 36 of said derived sequence.

The present invention provides in a further aspect a rainbow trout egg, such as an isolated rainbow trout egg, which comprises within its genome (e.g., on chromosome 1 of its genome) at least one allele conferring IPN resistance ("IPN resistance allele").

According to certain embodiments, the present invention provides a rainbow trout egg, such as an isolated rainbow trout egg, which comprises within its genome (e.g., on chromosome 1 of its genome) at least one nucleotide sequence selected from the group consisting of a) the nucleotide sequences set forth in SEQ ID NOs: 79 to 156 and 230 to 299, and b) nucleotide sequences derived from any one of SEQ ID NOs: 79 to 156 and 230 to 299 by 1 to 5, such as 1 to 2, nucleotide substitutions, provide that said nucleotide substitutions are not at position 36 of said derived sequence.

Present invention provides in a further aspect a population of rainbow trout eggs, such as an isolated population of rainbow trout eggs, each individual egg within the population comprising within its genome (e.g., on chromosome 1 of its genome) at least one allele conferring IPN resistance ("IPN resistance allele").

According to certain embodiments, the present invention provides a population of rainbow trout eggs, such as an isolated population of rainbow trout eggs, each individual egg within the population comprising within its genome (e.g., on chromosome 1 of its genome) at least one nucleotide sequence selected from the group consisting of a) the nucleotide sequences set forth in SEQ ID NOs: 79 to 156 and 230 to 299, and b) nucleotide sequences derived from any one of SEQ ID NOs: 79 to 156 and 230 to 299 by 1 to 5, such as 1 to 2, nucleotide substitutions, provide that said nucleotide substitutions are not at position 36 of said derived sequence.

The present invention provides in a further aspect a nucleic acid molecule, such as an isolated nucleic acid molecule, comprising at least one nucleotide sequence selected from the group consisting of a) the nucleotide sequences set forth in SEQ ID NO: 79 to 156 and 230 to 299, b) nucleotide sequences derived from any one of SEQ ID NOs: 79 to 156 and 230 to 299 by 1 to 5, such as 1 to 2, nucleotide substitutions, provided that said nucleotide substitutions are not at position 36 of said derived sequence, and c) complements of a) and b).

According to certain embodiments, the present invention provides a nucleic acid molecule, such as an isolated nucleic acid molecule, which comprises at least one nucleotide sequence selected from the group consisting of a) the nucleotide sequences set forth in SEQ ID NOs: 79, 80, 230, 231 and 232 b) nucleotide sequences derived from any one of SEQ ID NO: 79, 80, 230, 231 and 232 by 1 to 5, such as 1 to 2, nucleotide substitutions, provided that said nucleotide substitutions are not at position 36 of said derived sequence, and c) complements of a) and b).

The present invention provides in a further aspect an oligonucleotide, such as an isolated oligonucleotide, comprising at least 10 contiguous nucleotides, such as at least 16 contiguous nucleotides, of a nucleotide sequence selected from the group consisting of a) the nucleotide sequences set forth in SEQ ID NOs: 79 to 156 and 230 to 299, and b) nucleotide sequences derived from any one of SEQ ID NO: 79 to 156 and 230 to 299 by 1 to 5, such as 1 to 2, nucleotide substitutions, provided that said nucleotide substitutions are not at position 36 of said derived sequence; wherein said at least 10 contiguous nucleotides include the nucleotide at position 36 of a) or b); or a complement of said oligonucleotide.

DETAILED DESCRIPTION OF THE INVENTION

Figure 1:
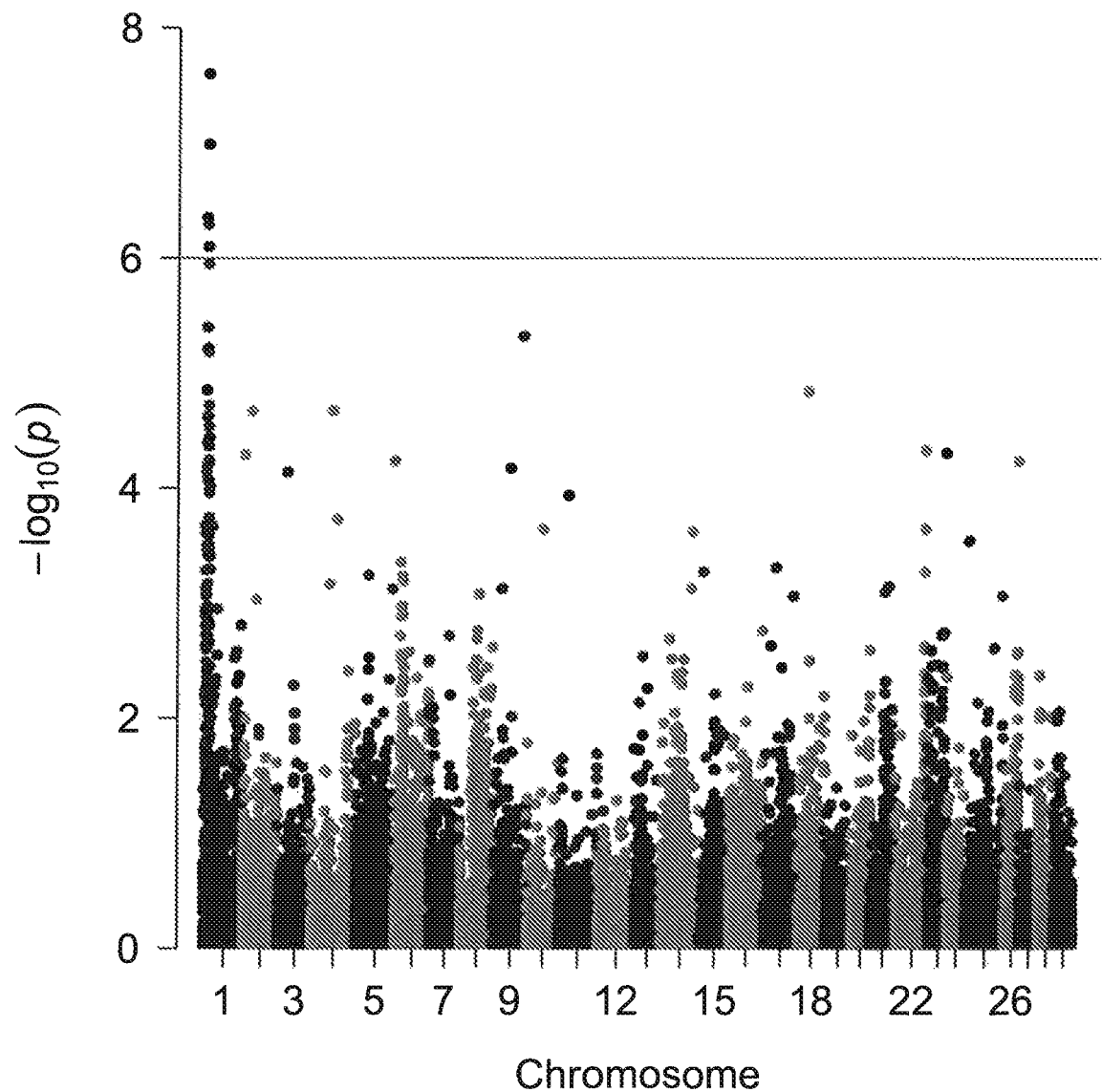
FIG. 1. "Manhattan plot" from a genome wide association study (GWAS), searching for SNPs associated with resistance to IPN in rainbow trout. SNPs distributed across the rainbow trout genome were tested for their association to IPN-resistance, and consequently, for their ability to predict IPN-resistance. Each data point represent one individual SNP, each SNP having been tested individually. The position of the SNPs (x-axis) corresponds to their position on the female genetic map. The horizontal line indicates the significance level corresponding to a false positive rate ($\alpha$) of 0.05 when the null hypothesis assumes that none of the SNPs are associated with IPN-resistance, and applying a Bonferroni correction in order to correct for the fact that (approximately) 50,000 SNPs were tested. The Bonferroni correction is highly conservative in this case, since it assumes that all tests (SNPs) are independent, which they are not. On the y-axis, the SNPs are plotted according to the negative of the base-10 logarithm of their p-values. As the figure illustrates, the SNPs most strongly associated with IPN-resistance are located on chromosome 1.

Unless specifically defined herein, all technical and scientific terms used have the same meaning as commonly understood by a skilled artisan in the fields of genetics, biochemistry, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail.

Polymorphisms and IPN Resistance Allele(s) of the Invention

The present inventors have identified a quantitative trait locus (QTL) responsible for a significant fraction of the genetic variation in resistance to IPN in rainbow trout. More specifically, the present inventors have identified polymorphisms, and in particular single nucleotide polymorphisms (SNP), within the genome, more particularly on chromosome 1, of rainbow trout which are associated with increased resistance of the fish to infectious pancreatic necrosis (IPN). Specific details of single nucleotide polymorphisms of the invention are provided in Table 1 below. The respective nucleotide sequences including the SNP (at position 36) are shown in Table 2.

The polymorphisms of the invention can be present in either of two forms, i.e., the polymorphisms have two alleles. One allele can be characterized as being an allele conferring increased resistance to infectious pancreatic necrosis. This means that a rainbow trout having such allele at the position of a polymorphism detailed herein shows increased resistance to IPN. This allele is herein denoted "IPN resistance allele". The respective IPN resistance allele for each of the single nucleotide polymorphism of the invention is specified in Table 1 below. An IPN resistance allele according to the present invention may therefore be used to predict increased resistance of a rainbow trout to infectious pancreatic necrosis. An IPN resistance allele according to the present invention may also be used to select a rainbow trout having increased resistance to infectious pancreatic necrosis. The other allele can be characterized as being an allele that does not confer increased resistance to infectious pancreatic necrosis. Such allele is herein denoted "non-IPN resistance allele".

Rainbow trout are diploid, in some case triploid organisms, and thus possess at least two copies of the polymorphisms of the invention (one copy to be found on each copy of chromosome 1).

As demonstrated herein, if at least one allele of a polymorphism, and more particularly of a SNP, is the respective IPN resistance allele then the rainbow trout has increased resistance to infectious pancreatic necrosis compared to a rainbow trout wherein both alleles are non-IPN resistance alleles (i.e. such rainbow trout being homozygous for the non-IPN resistance allele). In a great number of cases the resistance to infectious pancreatic necrosis is even further increased if both alleles of a polymorphism, and more particularly of a SNP, are the respective IPN resistance allele (such rainbow trout being homozygous for the IPN resistance allele). Such further increase is, for example, seen for SNPs AX-89929954 (SNP #1), AX-89918280 (SNP #2), and chr1_7515539 (SNP #160) which are the most statistically significant SNPs associated with IPN (see Table 3).

A polymorphism of the invention may be any of several polymorphisms associated with increased resistance of a rainbow trout to infectious pancreatic necrosis. Particularly, a polymorphism of the invention is a polymorphism located on chromosome 1 of rainbow trout (following the nomenclature of Palti et al. (2011)), i.e. a polymorphism found to be located on chromosome 1 on the basis of genetic linkage analysis, Fluorescence In Situ Hybridization (FISH) or any other method that assigns DNA polymorphisms to their respective chromosomes.

A polymorphism of the invention may be any polymorphism, including single nucleotide polymorphism, located within any of the rainbow trout genomic sequences listed in the column titled "GenBank contig" in Table 1.

A polymorphism of the invention may be any polymorphism, including single nucleotide polymorphism, located within rainbow trout genomic sequence having GenBank ID FR904293.1.

A polymorphism of the invention may be any polymorphism, including single nucleotide polymorphism, whose genetic distance from SNP AX-89929954 is smaller than or equal to 10 centi-Morgan. Here, the genetic distance is to be estimated on the basis of recombination event occurring in female rainbow trout, and not on recombination events occurring in male rainbow trout. A person who is skilled in the art will know how to estimate genetic map distances, as well as what data material is required for this estimation.

A polymorphism of the invention may be any polymorphism, including single nucleotide polymorphism, which is in strong linkage disequilibrium (LD) with SNP AX-89929954. Here, two polymorphisms are defined to be in strong LD if the square of the correlation coefficient between the two loci ($r^2$, the most commonly used measure of LD) is equal to or larger than 0.5. A person who is skilled in the art will know how to estimate $r^2$, as well as what data material is required for this estimation.

A polymorphism of the invention may be at least one of the single nucleotide polymorphisms listed in Table 1. Therefore, according to certain embodiments, the at least one SNP of the invention is selected from the SNPs listed in Table 1. Each of the SNPs listed in Table 1 is contemplated as being disclosed individually as part of the present invention.

TABLE 1

SNPs associated with increased resistance to IPN. A = Adenine, G = Guanine; C = Cytosine, T = Thymine. Affymetix ID is a unique identifier given to each SNP by Affymetrix, the provider of a commercial genotyping assay which incorporates many of the SNPs listed in the table; the Affymerix ID serves as a link to further details pertaining to the SNPs, provided in a file which can be downloaded from http://www.affymetrix.com/estore/. GenBank contig is the name of a GenBank DNA contig (a genome sequence from rainbow trout) wherein the SNP resides, and the position is the position of the SNP within this contig. dbSNP ss-no.(ss#) is the NCBI submission number of the SNP within the NCBI (National Center for Biotechnology Information) Single Nucleotide Polymorphism Database (dbSNP); the respective reference SNP number (rs#) can be retrieved from NCBI.

| SNP # | Name-Affymetrix ID | SEQ ID NO: | GenBank contig | Position in GenBank contig | dbSNP ss-No. (ss#) | IPN resistance allele | Non-IPN resistance allele |
|---|---|---|---|---|---|---|---|
| 1 | AX-89929954 | 1 | FR904293.1 | 1651243 | 1398298005 | C | A |
| 2 | AX-89918280 | 2 | FR904293.1 | 1353665 | 1399389616 | G | A |
| 3 | AX-89938309 | 3 | FR930508.1 | 112 | 1958018818 | T | G |
| 4 | AX-89960828 | 4 | FR932837.1 | 3160 | 1399779599 | T | C |
| 5 | AX-89930342 | 5 | FR904678.1 | 635143 | 1947222023 | G | T |
| 6 | AX-89928530 | 6 | CCAF010009978.1 | 26749 | 1958018819 | G | A |
| 7 | AX-89949788 | 7 | CCAF010004413.1 | 12904 | 1399149964 | G | A |
| 8 | AX-89928131 | 8 | CCAF010064480.1 | 22746 | 1398895466 | A | G |
| 9 | AX-89949832 | 9 | CCAF010004406.1 | 28738 | 1398503537 | A | C |
| 10 | AX-89916790 | 10 | FR913799.1 | 19857 | 1398404711 | T | C |
| 11 | AX-89973719 | 11 | FR904293.1 | 1133744 | 1398781172 | A | G |

TABLE 1-continued

SNPs associated with increased resistance to IPN. A = Adenine, G = Guanine; C = Cytosine, T = Thymine. Affymetix ID is a unique identifier given to each SNP by Affymetrix, the provider of a commercial genotyping assay which incorporates many of the SNPs listed in the table; the Affymerix ID serves as a link to further details pertaining to the SNPs, provided in a file which can be downloaded from http://www.affymetrix.com/estore/. GenBank contig is the name of a GenBank DNA contig (a genome sequence from rainbow trout) wherein the SNP resides, and the position is the position of the SNP within this contig. dbSNP ss-no.(ss#) is the NCBI submission number of the SNP within the NCBI (National Center for Biotechnology Information) Single Nucleotide Polymorphism Database (dbSNP); the respective reference SNP number (rs#) can be retrieved from NCBI.

| SNP # | Name-Affymetrix ID | SEQ ID NO: | GenBank contig | Position in GenBank contig | dbSNP ss-No. (ss#) | IPN resistance allele | Non-IPN resistance allele |
|---|---|---|---|---|---|---|---|
| 12 | AX-89962023 | 12 | FR905874.1 | 180661 | 1399167685 | T | G |
| 13 | AX-89921280 | 13 | CCAF010065595.1 | 582 | 1958018820 | A | G |
| 14 | AX-89931666 | 14 | FR904678.1 | 34120 | 1398786470 | A | G |
| 15 | AX-89921585 | 15 | FR904678.1 | 474477 | 1958018821 | A | G |
| 16 | AX-89953905 | 16 | FR904293.1 | 1653144 | 1958018822 | G | A |
| 17 | AX-89952945 | 17 | CCAF010008412.1 | 13251 | 1398012752 | T | C |
| 18 | AX-89934682 | 18 | CCAF010013460.1 | 37152 | 1399451952 | T | G |
| 19 | AX-89951942 | 19 | CCAF010065594.1 | 2104 | 1399313562 | T | C |
| 20 | AX-89937020 | 20 | FR905950.1 | 96027 | 1398530423 | A | C |
| 21 | AX-89924837 | 21 | FR907200.1 | 27594 | 1398178048 | A | C |
| 22 | AX-89958601 | 22 | FR941615.1 | 565 | 1399167665 | G | A |
| 23 | AX-89923477 | 23 | FR904678.1 | 226522 | 1398405156 | A | C |
| 24 | AX-89959350 | 24 | FR904678.1 | 213771 | 1398405213 | T | G |
| 25 | AX-89929482 | 25 | FR915682.1 | 18182 | 1958018823 | T | G |
| 26 | AX-89937712 | 26 | CCAF010064481.1 | 7407 | 1398895514 | A | G |
| 27 | AX-89949602 | 27 | CCAF010031932.1 | 11494 | 1398103752 | G | A |
| 28 | AX-89925103 | 28 | CCAF010064481.1 | 13695 | 1398895535 | A | G |
| 29 | AX-89938051 | 29 | FR934499.1 | 1547 | 1399453527 | T | C |
| 30 | AX-89924174 | 30 | FR904977.1 | 400797 | 1397830928 | A | G |
| 31 | AX-89936461 | 31 | FR904503.1 | 739897 | 1397951621 | G | A |
| 32 | AX-89916703 | 32 | CCAF010010010.1 | 3461 | 1398072822 | T | G |
| 33 | AX-89935317 | 33 | FR950362.1 | 1884 | 1398377786 | T | C |
| 34 | AX-89966423 | 34 | FR905282.1 | 358121 | 1399924230 | C | T |
| 35 | AX-89933348 | 35 | FR904343.1 | 1639174 | 1397844923 | T | C |
| 36 | AX-89969315 | 36 | FR904977.1 | 54937 | 1958018824 | T | C |
| 37 | AX-89919958 | 37 | — | — | 1399438973 | G | A |
| 38 | AX-89968417 | 38 | CCAF010031923.1 | 32394 | 1398245860 | A | G |
| 39 | AX-89946851 | 39 | CCAF010004466.1 | 1967 | 1958018825 | G | A |
| 40 | AX-89976917 | 40 | FR904293.1 | 2327239 | 1398180239 | C | T |
| 41 | AX-89945446 | 41 | FR968676.1 | 1099 | 1399533056 | G | A |
| 42 | AX-89919457 | 42 | FR904381.1 | 1273596 | 1398863772 | G | T |
| 43 | AX-89973597 | 43 | FR906031.1 | 36393 | 1399449790 | T | C |

TABLE 1-continued

SNPs associated with increased resistance to IPN. A = Adenine, G = Guanine; C = Cytosine, T = Thymine. Affymetix ID is a unique identifier given to each SNP by Affymetrix, the provider of a commercial genotyping assay which incorporates many of the SNPs listed in the table; the Affymerix ID serves as a link to further details pertaining to the SNPs, provided in a file which can be downloaded from http://www.affymetrix.com/estore/. GenBank contig is the name of a GenBank DNA contig (a genome sequence from rainbow trout) wherein the SNP resides, and the position is the position of the SNP within this contig. dbSNP ss-no.(ss#) is the NCBI submission number of the SNP within the NCBI (National Center for Biotechnology Information) Single Nucleotide Polymorphism Database (dbSNP); the respective reference SNP number (rs#) can be retrieved from NCBI.

| SNP # | Name-Affymetrix ID | SEQ ID NO: | GenBank contig | Position in GenBank contig | dbSNP ss-No. (ss#) | IPN resistance allele | Non-IPN resistance allele |
|---|---|---|---|---|---|---|---|
| 44 | AX-89938138 | 44 | FR913799.1 | 490 | 1398404618 | T | C |
| 45 | AX-89971866 | 45 | CCAF010031920.1 | 30454 | 1958018826 | T | C |
| 46 | AX-89958882 | 46 | CCAF010052946.1 | 13953 | 1399924706 | C | A |
| 47 | AX-89961273 | 47 | CCAF010031914.1 | 39607 | 1399509347 | G | A |
| 48 | AX-89944901 | 48 | CCAF010005406.1 | 331 | 1398303825 | A | G |
| 49 | AX-89919465 | 49 | FR910575.1 | 22175 | 1398003168 | G | T |
| 50 | AX-89959425 | 50 | CCAF010011658.1 | 30908 | 1399510298 | G | A |
| 51 | AX-89917102 | 51 | CCAF010031900.1 | 8080 | 1398786550 | T | C |
| 52 | AX-89959281 | 52 | CCAF010086830.1 | 12600 | 1399845186 | G | A |
| 53 | AX-89916766 | 53 | CCAF010034613.1 | 16962 | 1398773412 | G | T |
| 54 | AX-89920507 | 54 | — | — | 1958018827 | T | A |
| 55 | AX-89957370 | 55 | HG973520.1 | 2622978 | 1399185465 | A | C |
| 56 | AX-89934009 | 56 | FR904293.1 | 2034797 | 1958018828 | G | A |
| 57 | AX-89929663 | 57 | CCAF010005452.1 | 22290 | 1958018829 | C | A |
| 58 | AX-89952300 | 58 | CCAF010056921.1 | 2048 | 1399343172 | G | T |
| 59 | AX-89916572 | 59 | FR904293.1 | 914413 | 1958018830 | T | G |
| 60 | AX-89946911 | 60 | FR904503.1 | 1083993 | 1958018831 | T | C |
| 61 | AX-89974593 | 61 | — | — | 1397844976 | C | A |
| 62 | AX-89927158 | 62 | CCAF010077121.1 | 16057 | 1399413068 | A | C |
| 63 | AX-89970383 | 63 | FR906481.1 | 114723 | 1958018832 | G | A |
| 64 | AX-89965404 | 64 | FR904294.1 | 287791 | 1958018833 | C | T |
| 65 | AX-89955634 | 65 | FR905454.1 | 302890 | 1958018834 | T | C |
| 66 | AX-89932926 | 66 | CCAF010004500.1 | 3394 | 1399419631 | G | T |
| 67 | AX-89941493 | 67 | CCAF010008330.1 | 11016 | 1398381496 | A | G |
| 68 | AX-89943031 | 68 | FR915682.1 | 18027 | 1399011222 | C | T |
| 69 | AX-89957682 | 69 | CCAF010044148.1 | 5113 | 1399499631 | A | G |
| 70 | AX-89960611 | 70 | FR904301.1 | 1592957 | 1399172382 | T | C |
| 71 | AX-89950199 | 71 | HG973520.1 | 2957326 | 1958018835 | T | C |
| 72 | AX-89928407 | 72 | FR904678.1 | 632394 | 1398105778 | T | C |
| 73 | AX-89962035 | 73 | CCAF010004633.1 | 13819 | 1398455543 | C | T |
| 74 | AX-89931951 | 74 | CCAF010011658.1 | 6770 | 1399511408 | A | C |
| 75 | AX-89976536 | 75 | HG973520.13 | 1007871 | 1399510949 | T | G |

TABLE 1-continued

SNPs associated with increased resistance to IPN. A = Adenine, G = Guanine; C = Cytosine, T = Thymine. Affymetix ID is a unique identifier given to each SNP by Affymetrix, the provider of a commercial genotyping assay which incorporates many of the SNPs listed in the table; the Affymerix ID serves as a link to further details pertaining to the SNPs, provided in a file which can be downloaded from http://www.affymetrix.com/estore/. GenBank contig is the name of a GenBank DNA contig (a genome sequence from rainbow trout) wherein the SNP resides, and the position is the position of the SNP within this contig. dbSNP ss-no.(ss#) is the NCBI submission number of the SNP within the NCBI (National Center for Biotechnology Information) Single Nucleotide Polymorphism Database (dbSNP); the respective reference SNP number (rs#) can be retrieved from NCBI.

| SNP # | Name-Affymetrix ID | SEQ ID NO: | GenBank contig | Position in GenBank contig | dbSNP ss-No. (ss#) | IPN resistance allele | Non-IPN resistance allele |
|---|---|---|---|---|---|---|---|
| 76 | AX-89916801 | 76 | FR933232.1 | 298 | 1397811509 | G | A |
| 77 | AX-89929085 | 77 | CCAF010044174.1 | 47606 | 1958018836 | G | A |
| 78 | AX-89925267 | 78 | HG973520.1 | 723322 | 1958018837 | G | T |
| 160 | chr1_7515539 | 160 | FR904293.1 | 1279149 | 1947221883 | G | T |
| 161 | chr1_7108873 | 161 | CCAF010004472.1 | 29772 | 1947221884 | G | A |
| 162 | chr1_6864558 | 162 | FR904293.1 | 1930130 | 1947221885 | C | T |
| 163 | chr1_7186663 | 163 | CCAF010004468.1 | 16367 | 1947221886 | T | C |
| 164 | chr1_6730531 | 164 | FR904293.1 | 2064157 | 1947221887 | T | G |
| 165 | chr1_27891953 | 165 | FR904658.1 | 512537 | 1947221888 | T | C |
| 166 | AX-89953259 | 166 | CCAF010004501.1 | 540 | 1947221889 | G | T |
| 167 | chr1_6740481 | 167 | FR904293.1 | 2054207 | 1947221890 | T | C |
| 168 | chr1_6770611 | 168 | FR904293.1 | 2024077 | 1947221891 | C | T |
| 169 | chr1_7412807 | 169 | FR904293.1 | 1381881 | 1947221892 | G | C |
| 170 | chr1_7360179 | 170 | FR904293.1 | 1434509 | 1947221893 | A | T |
| 171 | chr1_7411803 | 171 | FR904293.1 | 1382885 | 1947221894 | G | A |
| 172 | chr1_7431445 | 172 | FR904293.1 | 1363243 | 1947221895 | C | T |
| 173 | chr1_7433199 | 173 | FR904293.1 | 1361489 | 1947221896 | C | A |
| 174 | chr1_7441254 | 174 | FR904293.1 | 1353434 | 1947221897 | A | G |
| 175 | chr1_7441877 | 175 | FR904293.1 | 1352811 | 1947221898 | A | C |
| 176 | chr1_7533570 | 176 | FR904293.1 | 1261118 | 1947221899 | G | A |
| 177 | chr1_6834898 | 177 | FR904293.1 | 1959790 | 1947221900 | T | C |
| 178 | chr1_6730142 | 178 | FR904293.1 | 2064546 | 1947221901 | T | C |
| 179 | chr1_6746052 | 179 | FR904293.1 | 2048636 | 1947221902 | G | A |
| 180 | chr1_6794061 | 180 | FR904293.1 | 2000627 | 1947221903 | G | T |
| 181 | chr1_7399212 | 181 | CCAF010004460.1 | 4509 | 1947221904 | T | C |
| 182 | chr1_7442637 | 182 | FR904293.1 | 1352051 | 1947221905 | A | G |
| 183 | chr1_7358019 | 183 | FR904293.1 | 1436669 | 1947221906 | G | A |
| 184 | chr1_7709828 | 184 | CCAF010004440.1 | 18118 | 1947221907 | A | C |
| 185 | chr1_7598090 | 185 | CCAF010004445.1 | 30169 | 1947221908 | T | C |
| 186 | chr1_7626471 | 186 | CCAF010004445.1 | 1788 | 1947221909 | G | A |
| 187 | chr1_7598743 | 187 | CCAF010004445.1 | 29516 | 1947221910 | T | G |
| 188 | chr1_7670293 | 188 | FR904293.1 | 1124395 | 1947221911 | A | T |
| 189 | chr1_7670561 | 189 | FR904293.1 | 1124127 | 1947221912 | T | G |
| 190 | chr1_7647634 | 190 | CCAF010004444.1 | 4148 | 1947221913 | T | A |
| 191 | chr1_7356089 | 191 | FR904293.1 | 1438599 | 1947221914 | C | G |
| 192 | chr1_8109044 | 192 | FR904293.1 | 685644 | 1947221915 | G | A |
| 193 | chr1_10439048 | 193 | CCAF010013455.1 | 19790 | 1947221916 | A | C |
| 194 | chr1_8142346 | 194 | CCAF010004413.1 | 25975 | 1947221917 | T | C |
| 195 | chr1_8092208 | 195 | FR904293.1 | 702480 | 1947221918 | T | G |
| 196 | chr1_8138683 | 196 | CCAF010004413.1 | 29638 | 1947221919 | A | T |
| 197 | chr1_8139206 | 197 | CCAF010004413.1 | 29115 | 1947221920 | G | T |
| 198 | chr1_8139744 | 198 | CCAF010004413.1 | 28577 | 1947221921 | G | C |
| 199 | chr1_8140789 | 199 | CCAF010004413.1 | 27532 | 1947221922 | T | A |
| 200 | chr1_8141687 | 200 | CCAF010004413.1 | 26634 | 1947221923 | A | G |
| 201 | chr1_8154917 | 201 | CCAF010004413.1 | 13404 | 1947221924 | G | T |
| 202 | chr1_7454708 | 202 | FR904293.1 | 1339980 | 1947221925 | T | C |
| 203 | chr1_7504847 | 203 | FR904293.1 | 1289841 | 1947221926 | T | C |
| 204 | chr1_7505686 | 204 | FR904293.1 | 1289002 | 1947221927 | T | A |
| 205 | chr1_7505817 | 205 | FR904293.1 | 1288871 | 1947221928 | A | T |
| 206 | chr1_8202031 | 206 | CCAF010004411.1 | 32050 | 1947221929 | T | G |
| 207 | chr1_8228173 | 207 | CCAF010004411.1 | 5908 | 1947221930 | A | G |
| 208 | chr1_8309469 | 208 | CCAF010004406.1 | 46564 | 1947221931 | T | C |
| 209 | chr1_8163977 | 209 | CCAF010004413.1 | 4344 | 1947221932 | A | C |
| 210 | chr1_27786931 | 210 | FR904658.1 | 617559 | 1947221933 | C | G |
| 211 | chr1_8194629 | 211 | CCAF010004411.1 | 39452 | 1947221934 | A | G |
| 212 | chr1_7505259 | 212 | FR904293.1 | 1289429 | 1947221935 | G | A |
| 213 | chr1_8474659 | 213 | FR904293.1 | 320029 | 1947221936 | C | T |
| 214 | chr1_8282602 | 214 | FR904293.1 | 512086 | 1947221937 | T | G |
| 215 | chr1_8306806 | 215 | CCAF010004406.1 | 49227 | 1947221938 | T | A |
| 216 | chr1_8341618 | 216 | CCAF010004406.1 | 14415 | 1947221939 | A | G |

TABLE 1-continued

SNPs associated with increased resistance to IPN. A = Adenine, G = Guanine; C = Cytosine, T = Thymine. Affymetix ID is a unique identifier given to each SNP by Affymetrix, the provider of a commercial genotyping assay which incorporates many of the SNPs listed in the table; the Affymerix ID serves as a link to further details pertaining to the SNPs, provided in a file which can be downloaded from http://www.affymetrix.com/estore/. GenBank contig is the name of a GenBank DNA contig (a genome sequence from rainbow trout) wherein the SNP resides, and the position is the position of the SNP within this contig. dbSNP ss-no.(ss#) is the NCBI submission number of the SNP within the NCBI (National Center for Biotechnology Information) Single Nucleotide Polymorphism Database (dbSNP); the respective reference SNP number (rs#) can be retrieved from NCBI.

| SNP # | Name-Affymetrix ID | SEQ ID NO: | GenBank contig | Position in GenBank contig | dbSNP ss-No. (ss#) | IPN resistance allele | Non-IPN resistance allele |
|---|---|---|---|---|---|---|---|
| 217 | chr1_8343786 | 217 | CCAF010004406.1 | 12247 | 1947221940 | C | T |
| 218 | chr1_8345836 | 218 | CCAF010004406.1 | 10197 | 1947221941 | T | C |
| 219 | chr1_8350569 | 219 | CCAF010004406.1 | 5464 | 1947221942 | A | G |
| 220 | chr1_8402403 | 220 | FR904293.1 | 392285 | 1947221943 | G | A |
| 221 | AX-89962103 | 221 | FR904678.1 | 32488 | 1947221944 | A | G |
| 222 | chr1_8279302 | 222 | FR904293.1 | 515386 | 1947221945 | A | G |
| 223 | chr1_8334901 | 223 | CCAF010004406.1 | 21132 | 1947221946 | A | G |
| 224 | chr1_7561600 | 224 | CCAF010004449.1 | 1915 | 1947221947 | A | G |
| 225 | AX-89956272 | 225 | FR904678.1 | 215682 | 1947221948 | T | C |
| 226 | chr1_7938827 | 226 | FR904293.1 | 855861 | 1947221949 | A | G |
| 227 | chr1_10810229 | 227 | HG973520.1 | 3299862 | 1947221950 | T | C |
| 228 | chr1_11007071 | 228 | HG973520.1 | 3103020 | 1947221951 | G | T |
| 229 | chr1_10884171 | 229 | HG973520.1 | 3225920 | 1947221952 | C | T |

The NCBI dbSNP ss-no. in Table 1 above indicates a reference sequence and a position of the SNP within that reference sequence. Those skilled in the art may easily identify the reference sequence and the position of the SNP using the dbSNP ss submission number.

TABLE 2

Nucleotide sequence containing SNP. [IPN resistance allele/Non-IPN resistance allele] indicates the polymorphic site including the allele variants.

| SNP # | Name | SEQ ID NO: | Nucleotide sequence containing SNP | IPN resistance allele | Non-IPN resistance allele |
|---|---|---|---|---|---|
| 1 | AX-89929954 | 1 | GAAAGAAACAGTGATAGGCTTTTAGTGAGC ACATA[C/A]ATTTGACACACAGTTGTGTGA AAACAAAGCATGTG | C | A |
| 2 | AX-89918280 | 2 | AATATATGCCTTATATCAGGATCGCTAACCA CAGA[G/A]CAGGATTACAATTTAATACTTG CACAATATACATA | G | A |
| 3 | AX-89938309 | 3 | TCCTTGTATCGCAGAACTTTTAAATGTTTGA ATCC[T/G]TCTTGATGTTATGTGATTGGTGG ATTCAAATAAGT | T | G |
| 4 | AX-89960828 | 4 | GATGCAGGGTTGCACAGAACGTTGATGCC AGTAGT[T/C]ATGGCATGGCTCTCAGTACA AACTCATACTGAGTG | T | C |
| 5 | AX-89930342 | 5 | GAATGGCAATTAATTTCATGCTGAACTAACT GAAT[G/T]AAGAAAGGAAATGACCCCAACC CTGGTTGCATACT | G | T |
| 6 | AX-89928530 | 6 | CTCACATTCTTCACCTTATTGGAATGCATGG AAAG[G/A]CGCCATGGGAAGCTCACTGCG GTTTCGAACCTACG | G | A |
| 7 | AX-89949788 | 7 | AGTCAAAACCATGAAAAAGCTGATTTTAGA ATGAC[G/A]TTTGTAACACTCTCCATGATGA CGGTTAATAGAAG | G | A |

TABLE 2-continued

Nucleotide sequence containing SNP.
[IPN resistance allele/Non-IPN resistance allele]
indicates the polymorphic site including the allele variants.

| SNP # | Name | SEQ ID NO: | Nucleotide sequence containing SNP | IPN resistance allele | Non-IPN resistance allele |
|---|---|---|---|---|---|
| 8 | AX-89928131 | 8 | CGTGTCAATATTGGAACGACTAAATACGTG AATCT[A/G]TCAGGACGGGTGAACTGAGCA CAAATCTAGATCAT | A | G |
| 9 | AX-89949832 | 9 | AGTCCCTCCCTTAGTGGTATCAAACCATAAC TAAT[A/C]ATTTCTTCACAAATTATGGAACA AAAATAAATCCC | A | C |
| 10 | AX-89916790 | 10 | AAACGGAGTGCCGAAGACTCTGAACTCACA GACTC[T/C]CTGCCGAAAAAAACGAAAGTA ATGTCCTCAACTCT | T | C |
| 11 | AX-89973719 | 11 | TGTAAATTCATAAGTAAAGAGAACACCTGT TTAAG[A/G]AGAGCACATTATGCAAAACCT CATATGGAAAACGT | A | G |
| 12 | AX-89962023 | 12 | GCGTGGACACATGAGGGACGCTGTGCTCC CTGTGT[T/G]CTCCCAGCAACACGAGGTAA TTCTGCAGAACAACC | T | G |
| 13 | AX-89921280 | 13 | AAAGGAAGAAGAATGGTCAGGAGAGGTAA GGTTGG[A/G]AGGAATTATGCTTTTCAATG ATCTGGTCCTGCAAG | A | G |
| 14 | AX-89931666 | 14 | GCAATAATAACCATTGAAAAATATGCTTTG GGAAT[A/G]CTCCATTCTTTCCCTAGTCCA ATATGTGTTCTTT | A | G |
| 15 | AX-89921585 | 15 | AGGGGCGGTTAGACACATGGGTGTGGCTA GAAATG[A/G]GGGTTGGTGACACCCACTCC TTGGCACTCGATGAT | A | G |
| 16 | AX-89953905 | 16 | CAGCCAGCTTTCGAGTAGCAGGGAGAGGA CAGTAA[G/A]TATTGACACAGTGTAAGCAC TAGGCAGCACTAGGC | G | A |
| 17 | AX-89952945 | 17 | CAATACAATGAGGTGTAAATGGTTGAATTC ACTGT[T/C]GGATAAAGACTGCAGGACAGG CCAGTAAAACATTT | T | C |
| 18 | AX-89934682 | 18 | GTCCTCTATGCCTCCTATGAGTTCTTCGAGG CCAT[T/G]TGCAGCGTGAGTAGCTGCCTGG ACCCCATGCTGTA | T | G |
| 19 | AX-89951942 | 19 | ATTACTTTTGAATCACAGCTTCAGCATATAG CCCT[T/C]GCTATAGATACAATTCATACATC AAGATAATGACT | T | C |
| 20 | AX-89937020 | 20 | TATAGTAGATAATTGATTCAAATGGCAGTT GTATT[A/C]CACTTTTGTTTTTCTTTACAGTG GTCAGTGCTATT | A | C |
| 21 | AX-89924837 | 21 | CACACAAGGTAGATACACCTGCAGAGCATG TTTCG[A/C]AAATTAATAAGGTAAGTCTGA ATACCAAATACTGA | A | C |
| 22 | AX-89958601 | 22 | CTGTTGTTGGCCAGATTACCATCAGTGCAG TTGGA[G/A]TTCAGGCCTTATCTCTGCCTCA CACAACATCATCT | G | A |
| 23 | AX-89923477 | 23 | ATGGGTCGTGTTCATCAGGCAGAAAAATGA CGTAT[A/C]ATGCCCTAATGAACATGACCCT GGCATTACCTAGA | A | C |
| 24 | AX-89959350 | 24 | GAACCCCTAGGCTAGATGTTCAACCTGGCC TCAGG[T/G]CAATTCTGAAGATTGGTACG CAAATATGTTCGCC | T | G |
| 25 | AX-89929482 | 25 | CTGTTCATTCTGTCTGTTTCAGTTGGTGCTC TGGA[T/G]AGGAGAAAAGCCCACCTGCTGT GAGCCCCTTATTG | T | G |

TABLE 2 -continued

Nucleotide sequence containing SNP.
[IPN resistance allele/Non-IPN resistance allele]
indicates the polymorphic site including the allele variants.

| SNP # | Name | SEQ ID NO: | Nucleotide sequence containing SNP | IPN resistance allele | Non-IPN resistance allele |
|---|---|---|---|---|---|
| 26 | AX-89937712 | 26 | TCAGCGTCCTACAGCTAAACCATACGATGA AATTA[A/G]AACAATAAATTCAGTGTGATA TCCGTTATGGACCA | A | G |
| 27 | AX-89949602 | 27 | AGGTGGCAGGAAAAAGAATACCTCCAGCC AATCGC[G/A]TGACATCTGTCCATTCAAGCT GCAGCGAATCTGAC | G | A |
| 28 | AX-89925103 | 28 | CACGTCTCTCCAAAACGTTTCCACTTACTTT CCCA[A/G]GAAGCCTTTCCCGTTGGGCTGC TCCTTCAGCCACT | A | G |
| 29 | AX-89938051 | 29 | TCCATAGTGGCTACCAGCCCACATACGCAC TGACA[T/C]AATCACAGACAGACTGACAGA CAGCAGCTTGATCA | T | C |
| 30 | AX-89924174 | 30 | ATTTGAGAATCAGATGCAGAAGAGCAAGG TTTTCC[A/G]AGCCTGTGGCTATCCTCCATA CGATTCAACCACCT | A | G |
| 31 | AX-89936461 | 31 | TACCGTACAGCCCTGCTAAAGGAGGAAAAC AAGGG[G/A]CATGATGGTATGTCTTGGGGC TTCCTCAGGGCCCA | G | A |
| 32 | AX-89916703 | 32 | AAACAACTCTTCAAGATGATGAGTAACAAC CAAAG[T/G]CAGAAATTCCCCTTAAAATAA CTGAAAGGAAAAAG | T | G |
| 33 | AX-89935317 | 33 | GTGTTTGTAAACTGGTAATTGAAATTGTACT GATA[T/C]CAGATGATGTAGAAATAAATGT GTTTTGATGTAGG | T | C |
| 34 | AX-89966423 | 34 | TACAGAGGAGCTATGGGCTTCATCCTCATG TACGA[C/T]ATCTGCAATGAAGAGTCCTTCA ACGCTGTGCAGGA | C | T |
| 35 | AX-89933348 | 35 | GGCCCCATTATTTTGGCTTCTTGTGTAGCAG ACTT[T/C]GTAGTGTGTAAGGAAGCCTTGCT GGTCTTGCACAG | T | C |
| 36 | AX-89969315 | 36 | TCTGCTGAGCTCCCCTGAAAGACTGTGAGT CACAA[T/C]GGTCATTTATTTACCTTCTCTGC TTCACTCAACAC | T | C |
| 37 | AX-89919958 | 37 | ACTATTCCTCACATGCTACAGAATAGCTAG GGTAA[G/A]AGGATAGTAACATTAACCATA ACACCAAAGCTAAT | G | A |
| 38 | AX-89968417 | 38 | TCCAGTCCCACTAGTTTGGCTTTGAAGTCGC GGAT[A/G]GTAGACTCGCTCTTGTATCTCTT CTCAGTCAGGTC | A | G |
| 39 | AX-89946851 | 39 | GTAAAGGCTAGCAGACCCTGGGAACATTCC CCTGC[G/A]CTCAGCCTCTCTGCCATGGAG GAAATGCTAAAAGT | G | A |
| 40 | AX-89976917 | 40 | TTTTGAACAGCACTTATCTCTTCTCTCCAGA GGGG[C/T]ATATCACAGAGCATGACCAAAA AGTTAGCCAGCTA | C | T |
| 41 | AX-89945446 | 41 | AAGTTGACCTCTTATGATTTTATTATTGGTT TGTG[G/A]GCAAGATGTTCTGTCCAGGTT TCAACTTATAGCC | G | A |
| 42 | AX-89919457 | 42 | ACCACCACACCTGCCTGAGTCATGTAAGAA GATTA[G/T]GCATGGTGGATGGAGGTGGG AAGACAATTAATGGT | G | T |
| 43 | AX-89973597 | 43 | TGGTCGTCTGAGCCCTATGTAGTGAATTCA AACTT[T/C]CTTGTCTAAGCCAAGTATCAAC CTGCAAACCCAAG | T | C |

TABLE 2 -continued

Nucleotide sequence containing SNP.
[IPN resistance allele/Non-IPN resistance allele]
indicates the polymorphic site including the allele variants.

| SNP # | Name | SEQ ID NO: | Nucleotide sequence containing SNP | IPN resistance allele | Non-IPN resistance allele |
|---|---|---|---|---|---|
| 44 | AX-89938138 | 44 | TCCCCTTCTGTGTGCTCAAGGTGTGAATATT TTAT[T/C]GTTAACTTACTTCACTCGTGTCCT GCAGTTAGATG | T | C |
| 45 | AX-89971866 | 45 | AGCAGGCAGGTTGAGACAAGCCTGCAGGG CCAATA[T/C]CTGTCACTATCATAACTCAAG CCAACAATACCCAA | T | C |
| 46 | AX-89958882 | 46 | CTTGCTTGCCATCACCCGTCTGGTCCAAGG GACTA[C/A]GGTCAATATAACCTCCAATCTT AGTAACCTACCTC | C | A |
| 47 | AX-89961273 | 47 | GCAGACACCCTGGGCAGCGTTGGAGTGAT CATCTC[G/A]GCCATCCTGATGCAGAAGTA TGACCTGATGATCGC | G | A |
| 48 | AX-89944901 | 48 | AACTGGGCTAAAACGATGGGACGGTGTGC GAAAAC]A/G]AACTAACCCTAACCAGAAAA TTGTATGCTTTGTTT | A | G |
| 49 | AX-89919465 | 49 | ACCACCTTCACATTAACCTTCTCCATGACAA AACA[G/T]CCCCAAGCCTGAACAGCCCCTA GCCCCTTCCACTA | G | T |
| 50 | AX-89959425 | 50 | GAAGACACAAACTCAACAAGAGCACAACA ACACAG[G/A]CTTAAGGTACTGCAATTCCT GCTTATTTTCATAAA | G | A |
| 51 | AX-89917102 | 51 | AAATGAAAAGCGAGAAAGGACGGAGGTAT TTTAAA[T/C]ATATTTACCATAGTACTCACC GAAGGCTGCAGCCA | T | C |
| 52 | AX-89959281 | 52 | GAAATTGCCCCTTGATTTTGTCAGTTTAGCG ATCA[G/M]TATACACAAAATAATTAACTAAA GGAACAACCATA | G | A |
| 53 | AX-89916766 | 53 | AAACCACATGGTCTTCCTGCAACTTTGTGCC AAAT[G/T]AGTAGTTTCACAATGAACGTTGT GAGGTCTGCAGC | G | T |
| 54 | AX-89920507 | 54 | AGACACACAGCAGACTAGACTGAGGATGT GAACCA[T/A]TCCTCCACTTAATGCAAATGC AGGGACACATTCAG | T | A |
| 55 | AX-89957370 | 55 | CTATTCCTGCTTACCGTAGTTGAACTGGCTG TTGG[A/C]TTTCTCACAGTTGATGATGTTGA AGCGATAGGGCA | A | C |
| 56 | AX-89934009 | 56 | GGTGTAAGTACAGACTCTTTGAAAGCATGC AAATA[G/A]AAGTAAAGACACTGTCATTCC TTTAAATGTTCTTG | G | A |
| 57 | AX-89929663 | 57 | CTTCTTTATTTGCTATGATTATTACTTAATAG TGC[C/A]GATTGTATTTGTCATCCGTATTGA CTGCAGAACTA | C | A |
| 58 | AX-89952300 | 58 | ATTGTTCAAGGACATTATGCTTGTCCTACAT ATTG[G/T]CAATTTGATGTCGTTCTTTAACA TTTATAATTGAT | G | T |
| 59 | AX-89916572 | 59 | AAAACTTCTTAAGGGACAAGAAGGAAGTT GAAGTT[T/G]GGGGTGGGCTAGGAAGATA AAGAGTTGGGGGTGTG | T | G |
| 60 | AX-89946911 | 60 | ACCAACACAGAGATGAGACGTGCCGAGCG CAAGGC[T/C]ACCAAGAAGAAGCTCCCGCT GAAACGAGAGATGGA | T | C |
| 61 | AX-89974593 | 61 | TTAATCTAACTCACTCTCCATAACATCACAG AAGT[C/A]GATGTATTCGATTATAACAAGCT CAGGGCTGTCAT | C | A |

TABLE 2 -continued

Nucleotide sequence containing SNP.
[IPN resistance allele/Non-IPN resistance allele]
indicates the polymorphic site including the allele variants.

| SNP # | Name | SEQ ID NO: | Nucleotide sequence containing SNP | IPN resistance allele | Non-IPN resistance allele |
|---|---|---|---|---|---|
| 62 | AX-89927158 | 62 | CCCTTTACCTAGAATGGTCTGCAGCGTGAT GTCAA[A/C]GTGGTTATTTTGTCCATTGTTG CCAGTGATAAGCC | A | C |
| 63 | AX-89970383 | 63 | TGCAGAATGGACAACTGAAGAGAGATATG TCGCAC[G/A]TGAGGGAAACAACTCCGTGT CTAGGCCTTCTGAAG | G | A |
| 64 | AX-89965404 | 64 | GTTAGTGAAAGCCATTTCAGGGTAAACCCT CCAGG[C/T]CGTCCAATGTACCATAGAAGC AAAACAATGATAAT | C | T |
| 65 | AX-89955634 | 65 | CCCATCTGTCAGAACCTTGCCCACAGCTGTT TCCC[T/C]ACTCAATGAAAACAAGCTAACAT CCTGCAGGTTGA | T | C |
| 66 | AX-89932926 | 66 | GGAATATTCGAACGGCTTGTTGTCCAATGA GTCGG[G/T]GGCCTTACCACCACAAACCCC AAGGCCTGAGGCAG | G | T |
| 67 | AX-89941493 | 67 | TTAAGAGAGTCACAAACATGAAAAACTGTG ATAGT[A/G]CAAAGAAGATGAACGATAGG CTTGTGGATAGATTA | A | G |
| 68 | AX-89943031 | 68 | TTTATTTCAGCATTTAGCCCAATCCTGCTAA GAAC[C/T]GTCAGTTAATCACTAATTAGGA GAATATCAATAAA | C | T |
| 69 | AX-89957682 | 69 | CTCGAAGTAAGAAATGAAGCTGCAGGTCTG CAGGC[A/G]GAGTGCTGTCAGTGGAATATA ATACCCTTAATAGA | A | G |
| 70 | AX-89960611 | 70 | GATAAGGATGCAACAGATTTATTTTAGTTTT AGAT[T/C]ATGCTTTTCAGACTGATTTCGGCT CTTAAAAAGATA | T | C |
| 71 | AX-89950199 | 71 | TCTCTGTTCAATATTTAGAATAAAAAGCTGA CAAA[T/C}GTCACGTAATGGACTGGAAACA GCAGACACATGGC | T | C |
| 72 | AX-89928407 | 72 | CTATAGGTGGATGATATGATATGGTTGCAG CTAGA[T/C]AGTGACAGCTGCCTACCTTGTA AGTACCACCTCGA | T | C |
| 73 | AX-89962035 | 73 | GCGTTTCCAGTAAAACGACGTCCCCCTTCG CCCTA[C/T]ATTTAATGAGCACGTAGTCTAG ATTTTTGTTTAAC | C | T |
| 74 | AX-89931951 | 74 | GCAGGTTTTTGCAGAAATCAGTTGCTAATA AAGTT[A/C]TTCTGTAACCATTGTATAAGCA GGGTCACCATGAC | A | C |
| 75 | AX-89976536 | 75 | TTTCTCTTAATGCATCATCCTTGTGCGAAAT CATG[T/G]TAAGTACACACCGTTAAAGTTA GGTGCTTTGTTAC | T | G |
| 76 | AX-89916801 | 76 | AAACTAATGAAAAACACAAGAGTGCCTGCA GTAAC[G/A]CTGTACTAACGCTGTACTAAC AGTACACTCTCAGG | G | A |
| 77 | AX-89929085 | 77 | CTGCAGCAGATGGAACTATATCTCTAGTGG CTGTG[G/A]GTGGAGGAGGAGATGTGGTG AAGACTGAGCAGACA | G | A |
| 78 | AX-89925267 | 78 | CAGAAAGGAAAAATGTGTCAAAGTTCTAGA TAGTG[G/T]GTGGAAAGACTCAAACAATGC AGTTTGGAATGAAG | G | T |
| 160 | chr1_7515539 | 160 | ATAATTTACTTTTAAGATTTCTGACCGGCCT TGTT[G/T]TTTTTGCTTATGTGCCATTATTGC CGGCTAGACCA | G | T |

TABLE 2 -continued

Nucleotide sequence containing SNP.
[IPN resistance allele/Non-IPN resistance allele]
indicates the polymorphic site including the allele variants.

| SNP # | Name | SEQ ID NO: | Nucleotide sequence containing SNP | IPN resistance allele | Non-IPN resistance allele |
|---|---|---|---|---|---|
| 161 | chr1_7108873 | 161 | TAAAGAACAAGAAAACAGTACACATGCATT AACTC[G/A]CCATGTTGGTGTTGGAGAACT CGATACAGAGACAG | G | A |
| 162 | chr1_6864558 | 162 | CTCATGGAGAGGCATATCTTGTCCTATCCCC ATAA[C/T]GGCCACCTGGTAATGAGCCGTG AAACACTAGAGCC | C | T |
| 163 | chr1_7186663 | 163 | CCATTTAGATTATTCAACGGTGAAACATACA CATC[T/C]TGTAAATTACTCTCAGGTAACCG GACTTGATTTGT | T | C |
| 164 | chr1_6730531 | 164 | GTTTGTAGCCCCATCTCACTGGCTTCTTGAA AGTA[T/G]AATTTATTATGATTGTTTAATTA TAATAGTGAATA | T | G |
| 165 | chr1_27891953 | 165 | ATTTCATGTATTGGCCAACAAACGAACTTGT AGGC[T/C]TACGTGCCATGGTTGTCACATTT TAATAAAACATG | T | C |
| 166 | AX-89953259 | 166 | CACAGTTATAGCAACACTTAAGTAGAATGG AAATG[G/T]TTTCATTTAATTTTAGTCAGTT GGCATTCAGTTGA | G | T |
| 167 | chr1_6740481 | 167 | AGTCTGCAGACCCTACCCAGCCTGGTCTCC CAGGC[T/C]GTCACACAGCAGCACAGGGAC TTTCTGGATGGCTT | T | C |
| 168 | chr1_6770611 | 168 | ATTTCATGAACCTACACAAATCCAGTGTCAG GAAA[C/T]CCTTATAAACTTTTGCTCATGGG TGTGGAGATGTG | C | T |
| 169 | chr1_7412807 | 169 | ATAGGGCCAAGACAGAAGACAGACATGAA AGTCCT[G/C]CTGACGGGCAAAACATACAG ACCCCACCTGGAGAA | G | C |
| 170 | chr1_7360179 | 170 | TTCAGTTCAGTCAAACTGGCTGTCGTTGGC GCTGC[A/T]GGACTAGCTGGCACATTCAAT GGGAATCGTTTGTC | A | T |
| 171 | chr1_7411803 | 171 | AAAGGTCTTGATGGATATTGTGAGTTATCG GTGTC[G/A]TAAGAAATCGCCACCTCGCAA CCCATGCGACCCCA | G | A |
| 172 | chr1_7431445 | 172 | ACTCCAAAGCCACCACAGTCTCCTCCAGCCA TGGT[C/T]CATCCCTCCAGTAGCCCAACCAA TTACCAAACAGA | C | T |
| 173 | chr1_7433199 | 173 | ACATGCGACACATGGACAGATTAATTAGAT TGGGT[C/A]ACAACACATTGTATTGCAAAC ATGTGAAGCTATAA | C | A |
| 174 | chr1_7441254 | 174 | CTCTCATTCCTCCTATTCATATGTATATACAC TGG[A/G]CTAGTTAGTGTTATGGTTGTTATT CACTGGCAATA | A | G |
| 175 | chr1_7441877 | 175 | CAAACAACCCTGGAAGTCAAATCAAGAGGC AAGGC[A/C]CTGTGTTTCCTTGAAAGCCAG AGCTGTTTGTGTCC | A | C |
| 176 | chr1_7533570 | 176 | GGACCAGTGTTTCATATCCTGTGGTGAGCT TCACA[G/A]GTCAAATGTGATTAATCATAAT TGAAATCAAATTA | G | A |
| 177 | chr1_6834898 | 177 | AAGAGAATATTTGGAATAGCATTGGCAAAT ACACC[T/C]AGTGGGGTGGAGCTGCGTCAG TAGTGCACAGCACA | T | C |
| 178 | chr1_6730142 | 178 | GAAAATACTGTTACTGTAGAATATAATAGT CATAA[T/C]CCTCTGATCCAAATAATTATGC ATAGGTAGTGTTC | T | C |

TABLE 2-continued

Nucleotide sequence containing SNP.
[IPN resistance allele/Non-IPN resistance allele]
indicates the polymorphic site including the allele variants.

| SNP # Name | SEQ ID NO: | Nucleotide sequence containing SNP | IPN resistance allele | Non-IPN resistance allele |
|---|---|---|---|---|
| 179 chr1_6746052 | 179 | CTCAACATAATTAAATACCAACACCAATGTA AATC[G/A]TTCTTCAGAAACATTGAGTAAAT ATACCTTTACTA | G | A |
| 180 chr1_6794061 | 180 | AGAAAGCAGGAAGTTCAGGGGTCAACTGG GCAAGG[G/T]CAATAAGAGGCATTTCTAAC CGTGATCCTGAACCC | G | T |
| 181 chr1_7399212 | 181 | CGAATCAAGCCAAATAAAGCGGCCACATCT CAAAT[T/C]TGGTCAGCCTTTGGAGGAGAA CGATAAACGGACTT | T | C |
| 182 chr1_7442637 | 182 | CCGCAGATGACATCACTACACTGCCTGATA CAGCA[A/G]AGCGTGCTTTGCGGTGAGTTA AAAAAATACCATGG | A | G |
| 183 chr1_7358019 | 183 | CATGAGCTCAAGCACATCTGCTTCTTTCTTC AGGG[G/A]AAAAAAATACAGGGATCCCCA ACTGCATTTGATTT | G | A |
| 184 chr1_7709828 | 184 | TGTAGTCTAATAATGAGGGGATTAGTGAAA ACTTT[A/C]AGTCAGACCTTTGTCTTTAAAA CAATAGATTTCTG | A | C |
| 185 chr1_7598090 | 185 | ATGTTGGCATTGTAGGTGTCATAGCAACCA GGACC[T/C]AATCCCTGTACCAAACATGTG ATTAAAAACATATA | T | C |
| 186 chr1_7626471 | 186 | TTACCCGGCTAAGGAGCGCTTTCTTCGCACT TGGA[G/A]TATAATGAAACCTCAAACTGTC TCATTTAATATGC | G | A |
| 187 chr1_7598743 | 187 | TTGGGACAGTTTAACGTTCACCTCAGGAAT CCACA[T/G]CCTTTCATTTTAAGTTTATTTTA CTTGGCAGAGCA | T | G |
| 188 chr1_7670293 | 188 | CAACAATGCAACAGAAATTAGTGTGTGACA AAAAT[A/T]TGAACGGCTGCTTTGAAAATT ATTATCAAGGCAGT | A | T |
| 189 chr1_7670561 | 189 | GTGCCCTTATCTTACCGCTGATCAGTGGCA ACCCA[T/G]TAGTTTTTACTAACTGAAAACA CCATTGACATTCT | T | G |
| 190 chr1_7647634 | 190 | ACTGCCTGGTTATGACACCTGAACCCTACA GAGAG[T/A]GTGGGGCTATAGTTAAAATTT ACTCCCCTAAGGTT | T | A |
| 191 chr1_7356089 | 191 | AGGATCCCATCCCATAATGAATGGGTCTAG CTATA[C/G]ATTTATGACCAGTTGTTTTCCG GGTTTATGACCTC | C | G |
| 192 chr1_8109044 | 192 | TAAATAGCTTTGTGGAGTAGATTATGAATT GTATT[G/A]ATGCCATATCCACTGTTCTGCA ATGACTCTCCATA | G | A |
| 193 chr1_10439048 | 193 | ACCCTTTGATGTGATTTGCTTCTGAGAAACA TCAT[A/C]ATTTATTGATGCTTCCATTAAAG TAGCATAGATGT | A | C |
| 194 chr1_8142346 | 194 | AAATCACAGTGCAGTTATCACAAAACATTA TCTTC[T/C]GTGTTGTAGCCTAACTAGACTA TACAGCTGTAAAA | T | C |
| 195 chr1_8092208 | 195 | AAGTTTGTACCCCAAATTTCCATTTATGGAA TGGA[T/G]AGTTTAATTGCATTTTTGGATTG ATACAGTAACCA | T | G |
| 196 chr1_8138683 | 196 | GGGTTATGTATAAATCGATGTAATTATTATT TTTG[A/T]TTTAAAAGGTATAATATTGTATA ACATTGTAATAA | A | T |

TABLE 2 -continued

Nucleotide sequence containing SNP.
[IPN resistance allele/Non-IPN resistance allele]
indicates the polymorphic site including the allele variants.

| SNP # Name | SEQ ID NO: | Nucleotide sequence containing SNP | IPN resistance allele | Non-IPN resistance allele |
|---|---|---|---|---|
| 197 chr1_8139206 | 197 | GATGGCATTCACTATCCTTTAACACCACATCGTAG[G/T]TGATGTGGCACAAAAGCAGTGCTTAAAAAATAAAT | G | T |
| 198 chr1_8139744 | 198 | CACACAAAAACTATTAGCCCATCGTTGGTATAGTG[G/C]CAAAATGTTTTAAATGTCAGCAATCAAATTCAAGA | G | C |
| 199 chr1_8140789 | 199 | TCAGTGACGGCTGTGAACATAAAGGGTATAGTTGC[T/A]TTACTGGTCCACGTTCAAAAACCAGAGTTGAGATT | T | A |
| 200 chr1_8141687 | 200 | ACCAATTTTATAGTGACACAGAAAAATATCTAGAT[A/G]GATTCTCACCAAAGAGACCATATTTTGAAATAGT | A | G |
| 201 chr1_8154917 | 201 | CTCGATCTTCTCAAGTCAAGTGGCCAATTAAATAT[G/T]AATCTAAACACAACAATCCAGTTTGACTAGTTGTT | G | T |
| 202 chr1_7454708 | 202 | AGGACACACGCTGGGTGAGCAACACACATCCCCAG[T/C]CCCCCTGAGAAATCAGGCTTCTTACAAGGTTATAA | T | C |
| 203 chr1_7504847 | 203 | GGGGCCTTTGTCACACAGAAAGAGATGACATCAGT[T/C]GCAAGAGAGGCCATCAGTGTGTTCAAGGACTGGAA | T | C |
| 204 chr1_7505686 | 204 | GGAAGTCTAGGGTGGAAGGGAGGACATTGTGCGGG[T/A]CGTTCCACCAATTGAGTACCTTTTCAGCAGTCACT | T | A |
| 205 chr1_7505817 | 205 | CATCTCAAAAATAAGTTAAATAAATAAATTACTAT[A/T]GTAAGTGCCAAATAAAGTAACAGGGTTGAATTTTA | A | T |
| 206 chr1_8202031 | 206 | TGTAGATTAAACAACAAAGTCAGATTATCTGAGCC[T/G]GTGTGCCCCAACTTCAACAAGGAGACCGTATTGT | T | G |
| 207 chr1_8228173 | 207 | TTATCAATAATTATAATCAATGACTCACATCTTGA[A/G]ATCTACAGATGTAGACTTGTGATTGAGCTACTGT | A | G |
| 208 chr1_8309469 | 208 | AACGACCTCATACTGGGCCGGAGGATCTCCTTCTA[T/C]GAGCTCAGGGGGAAATAGGGTGTGGGAACTTCTC | T | C |
| 209 chr1_8163977 | 209 | AACAATACACTCTTGTCACTTGCCTTTACTGAGAA[A/C]GTCGTGGTGGACACCAGATTCCCATGTGAAGGAGA | A | C |
| 210 chr1_27786931 | 210 | AAGTCATTGACCTTGCTGCCTTGGTCGTCCCTCTC[C/G]GTGGTGGTGAACACGCGCGTTTTGGACTCCTCTGT | C | G |
| 211 chr1_8194629 | 211 | TGCTGAAGCTGGACAAGGAGAACGCCGTCGACCGC[A/G]CAGAGCAGGCTGAGACCGACAAGAAGGCAGCAGAG | A | G |
| 212 chr1_7505259 | 212 | GATCAGCTGGAGAACATCTACAAGGACAATCCCCT[G/A]GTGAATCTCCATTATGCCACTTTTAGCCAACAACT | G | A |
| 213 chr1_8474659 | 213 | TATGAGCAGCTGAAAAACAATTAAAATATTTTTTT[C/T]CCTGTGTTTGAGGAAGGGGAAGAGTGGACCCAGGG | C | T |
| 214 chr1_8282602 | 214 | ATATTTCCTTCCTCACATCCCTGGCAATTATAGTA[T/G]AATCTGAGCCATAACAACATGACCTGGATAGATGA | T | G |

TABLE 2 -continued

Nucleotide sequence containing SNP.
[IPN resistance allele/Non-IPN resistance allele]
indicates the polymorphic site including the allele variants.

| SNP # | Name | SEQ ID NO: | Nucleotide sequence containing SNP | IPN resistance allele | Non-IPN resistance allele |
|---|---|---|---|---|---|
| 215 | chr1_8306806 | 215 | AAATAATGGCATGCATTTGATATTAGTGTATGTTT[T/A]AAAACATTACAGGTTACAGAGAAACTATAAGGAAT | T | A |
| 216 | chr1_8341618 | 216 | ACATTCAGGTAATGGTACATTTTGTTTAATTAAAC[A/G]ACTTTCCATAGTTTGTGGAGAAAGGGTGTGTACTC | A | G |
| 217 | chr1_8343786 | 217 | GGTTTTATGCTTGAACATTCATTTTGGAATTTCCA[C/T]GACTGTCTCTAGCTGCTTTAATCTTCTTTCAAGGA | C | T |
| 218 | chr1_8345836 | 218 | TAGATGTTGAGTATATCTAACACTTCCAGAACATC[T/C]AGTTTAGTGCTGATGTGTCATTTCTGTTCCAGGCA | T | C |
| 219 | chr1_8350569 | 219 | CAATGGAACGCCTCCTCTTTCTAATAACCCTAGTA[A/G]AGTGCCGTCAAATGTCGTTGACAGATTTGAGTCTT | A | G |
| 220 | chr1_8402403 | 220 | AAAGGATATATTGATGAATATGACCTATGTACTGT[G/A]CTACTTAAATTCAGATAGCTGTTTGTTCATGTGTG | G | A |
| 221 | AX-89962103 | 221 | GCTATATTAATTCAGAAATGCCATTTTCTGTCATG[A/G]GGGAAAATATAGTTTTACACTTATCCCAGAAACAC | A | G |
| 222 | chr1_8279302 | 222 | TGTACATTGTAAAGATGGAGAAATATTGACAAAAA[A/G]ATGTCGTATAGGCTACTGTATTACTTGATATGTTT | A | G |
| 223 | chr1_8334901 | 223 | TTTAACCCAGCATTGTGACACATTTTTATTAAATC[A/G]AGGATGTGCAGTTTGTTTTATCCACTTCATTAATA | A | G |
| 224 | chr1_7561600 | 224 | AATTTGACCAATTTGTCTTCATACATTTCAGATAA[A/G]CTCACGATTCTTAAGTCATGTTGTATTTTTACCGA | A | G |
| 225 | AX-89956272 | 225 | CCTGACTGAAAGCAGGGCACAATATCAGGAAGTTGATTAGCCACCATCATGGCGGTGGAAAATTGTGCTT | T | C |
| 226 | chr1_7938827 | 226 | GTTATGGTGAAAGAGAAGCTCAGTTACGGAGCACA[A/G]CAGCAAATCCTCAACAAGCCAAACCTGCAAGACAA | A | G |
| 227 | chr1_10810229 | 227 | GACATCTGGAGAGCTAAGGAAACAACCAAGCCTGTGGAACTTCTATTGGGTGTCTCTGCTAGCAGTCCAA | T | C |
| 228 | chr1_11007071 | 228 | CAATAACTAGAAAAATACATTTCCTAAAGAAAATG[G/T]GTGTGCTTGCTTGCTTGTCTTAAAGTATTTATGTT | G | T |
| 229 | chr1_10884171 | 229 | TATCAGGACAAGCTGGAACTAGATAGCTGGTTATG[C/T]AACGTTAACTATTGGGATCAGAAACTGAACTAGCT | C | T |

The column in Table 2 labeled "Nucleotide sequence containing SNP" provides a reference nucleotide sequence for identification of the SNP within the genome of a rainbow trout. The sequences SEQ ID NO: 1 to 78 and SEQ ID NOs: 160 to 229 are each polymorphic sequences including a polymorphic site. A "polymorphic sequence" is a nucleotide sequence including a polymorphic site at which a SNP occurs. All or only part of the polymorphic sequence flanking the polymorphic site can be used by the skilled practitioner to identify the SNP within the genome of a rainbow trout.

According to particular embodiments, the at least one SNP of the invention is selected from the group consisting of: AX-89929954, AX-89918280, AX-89938309, AX-89960828, AX-89930342, AX-89928530, AX-89949788, AX-89928131, AX-89949832, AX-89916790, AX-89973719, AX-89962023, AX-89921280, AX-89931666, AX-89921585, AX-89953905, AX-89952945, AX-89934682, AX-89951942, AX-89937020, AX-89924837, AX-89958601, AX-89923477, AX-89959350, AX-89929482, AX-89937712, AX-89949602, AX-89925103, AX-89938051, AX-89924174, AX-89936461, AX-89916703, AX-89935317, AX-89966423, AX-89933348, AX-89969315, AX-89919958, AX-89968417, AX-89946851, AX-89976917, AX-89945446, AX-89919457, AX-89973597, AX-89938138, AX-89971866, AX-89958882, AX-89961273, AX-89944901, AX-89919465, AX-89959425, AX-89917102, AX-89959281, AX-89916766, AX-89920507, AX-89957370, AX-89934009, AX-89929663, AX-89952300, AX-89916572, AX-89946911, AX-89974593, AX-89927158, AX-89970383, AX-89965404, AX-89955634, AX-89932926, AX-89941493, AX-89943031, AX-89957682, AX-89960611, AX-89950199, AX-89928407, AX-89962035, AX-89931951, AX-89976536, AX-89916801, AX-89929085, AX-89925267, chr1_7515539, chr1_7108873, chr1_6864558, chr1_7186663, chr1_6730531, chr1_27891953, AX-89953259, chr1_6740481, chr1_6770611, chr1_7412807, chr1_7360179, chr1_7411803, chr1_7431445, chr1_7433199, chr1_7441254, chr1_7441877, chr1_7533570, chr1_6834898, chr1_6730142, chr1_6746052, chr1_6794061, chr1_7399212, chr1_7442637, chr1_7358019, chr1_7709828, chr1_7598090, chr1_7626471, chr1_7598743, chr1_7670293, chr1_7670561, chr1_7647634, chr1_7356089, chr1_8109044, chr1_10439048, chr1_8142346, chr1_8092208, chr1_8138683, chr1_8139206, chr1_8139744, chr1_8140789, chr1_8141687, chr1_8154917, chr1_7454708, chr1_7504847, chr1_7505686, chr1_7505817, chr1_8202031, chr1_8228173, chr1_8309469, chr1_8163977, chr1_27786931, chr1_8194629, chr1_7505259, chr1_8474659, chr1_8282602, chr1_8306806, chr1_8341618, chr1_8343786, chr1_8345836, chr1_8350569, chr1_8402403, AX-89962103, chr1_8279302, chr1_8334901, chr1_7561600, AX-89956272, chr1_7938827, chr1_10810229, chr1_11007071 and chr1_10884171.

According to other particular embodiments, the at least one SNP of the invention is selected from the group consisting of: AX-89929954, AX-89918280, AX-89938309, AX-89960828, AX-89930342, AX-89928530, AX-89949788, AX-89928131, AX-89949832, AX-89916790, AX-89973719, AX-89962023, AX-89921280, AX-89931666, AX-89921585, AX-89953905, AX-89952945, AX-89934682, AX-89951942, AX-89937020, AX-89924837, AX-89958601, AX-89923477, AX-89959350, AX-89929482, AX-89937712, AX-89949602, AX-89925103, AX-89938051, AX-89924174, AX-89936461, AX-89916703, AX-89935317 and AX-89966423.

According to other particular embodiments, the at least one SNP of the invention is selected from the group consisting of: AX-89929954, AX-89918280, AX-89938309, AX-89960828, AX-89930342, AX-89928530, AX-89949788, AX-89928131, AX-89949832, AX-89916790, AX-89973719, AX-89962023, AX-89921280, AX-89931666, AX-89921585, AX-89953905, AX-89952945 and AX-89934682.

According to other particular embodiments, the at least one SNP of the invention is AX-89929954 or AX-89918280.

According to more particular embodiments, the at least one SNP of the invention is AX-89929954.

According to other more particular embodiments, the at least one SNP of the invention is AX-89918280.

According to further particular embodiments, the at least one SNP of the invention is selected from the group consisting of: chr1_7515539, chr1_7108873, chr1_6864558, chr1_7186663, chr1_6730531, chr1_27891953, AX-89953259, chr1_6740481, chr1_6770611, chr1_7412807, chr1_7360179, chr1_7411803, chr1_7431445, chr1_7433199, chr1_7441254, chr1_7441877, chr1_7533570, chr1_6834898, chr1_6730142, chr1_6746052, chr1_6794061, chr1_7399212, chr1_7442637, chr1_7358019, chr1_7709828, chr1_7598090, chr1_7626471, chr1_7598743, chr1_7670293, chr1_7670561, chr1_7647634, chr1_7356089, chr1_8109044, and chr1 10439048.

According to further particular embodiment, the at least one SNP of the invention is selected from the group consisting of: chr1_7515539, chr1_7108873 and chr1_6864558.

According to certain embodiments, the at least one SNP of the invention is selected from the SNPs corresponding to position 36 of the polymorphic sequences set forth in any one of SEQ ID NOs: 1 to 78 and SEQ ID NOs: 160 to 229.

According to particular embodiments, the at least one SNP of the invention is selected from the SNPs corresponding to position 36 of the polymorphic sequences set forth in any one of SEQ ID NOs: 1 to 34.

According to further other particular embodiments, the at least one SNP of the invention is selected from the SNPs corresponding to position 36 of the polymorphic sequences set forth in any one of SEQ ID NOs: 160 to 193.

According to further other particular embodiments, the at least one SNP of the invention is selected from the SNPs corresponding to position 36 of the polymorphic sequences set forth in any one of SEQ ID NOs: 1 to 18.

According to further other particular embodiments, the at least one SNP of the invention is selected from the SNPs corresponding to position 36 of the polymorphic sequences set forth in any one of SEQ ID NOs: 160 to 162

According to particular embodiments, the at least one SNP of the invention is selected from the SNPs corresponding to position 36 of the polymorphic sequences set forth in SEQ ID NO: 1 or SEQ ID NO: 2.

According to more particular embodiments, the at least one SNP of the invention is the SNP defined by position 36 of the polymorphic sequence set forth in SEQ ID NO: 1.

According to more particular embodiments, the at least one SNP of the invention is the SNP defined by position 36 of the polymorphic sequence set forth in SEQ ID NO:2.

According to particular embodiments, the at least one SNP of the invention is selected from the SNPs corresponding to position 36 of the polymorphic sequences set forth in SEQ ID NO: 230, SEQ ID NO: 231 and SEQ ID NO:232.

According to more particular embodiments, the at least one SNP of the invention is the SNP defined by position 36 of the polymorphic sequence set forth in SEQ ID NO: 230.

According to more particular embodiments, the at least one SNP of the invention is the SNP defined by position 36 of the polymorphic sequence set forth in SEQ ID NO:231.

According to more particular embodiments, the at least one SNP of the invention is the SNP defined by position 36 of the polymorphic sequence set forth in SEQ ID NO: 232.

It is understood that the foregoing disclosure regarding the polymorphisms of the invention, and in particular regarding SNPs and IPN resistance allele(s), is applicable to the following aspects.

Methods of the Invention

The present invention provides in a one aspect a method for predicting increased resistance of a rainbow trout (*Oncorhynchus mykiss*) to infectious pancreatic necrosis (IPN). Particularly, the present invention provides a method for predicting increased resistance of a rainbow trout (*Oncorhynchus mykiss*) to infectious pancreatic necrosis (IPN), the method comprises:
    determining the presence of at least one allele conferring IPN resistance ("IPN resistance allele") within the genome (e.g., on chromosome 1 of the genome) of said rainbow trout.

According to certain embodiments, the at least one IPN resistance allele is an allele of at least one polymorphism, such as at least one single nucleotide polymorphism (SNP).

According to certain embodiments, the at least one SNP is selected from the SNPs listed in Table 1. Each of the SNPs listed in Table 1 is contemplated as being disclosed individually as part of the present invention.

According to certain embodiments, the present invention provides a method for predicting increased resistance of a rainbow trout (*Oncorhynchus mykiss*) to infectious pancreatic necrosis (IPN), the method comprises:
    determining the identity of a nucleotide of at least one allele, optionally of at least two alleles, of at least one single nucleotide polymorphism (SNP) associated with increased resistance to infectious pancreatic necrosis within the genome (e.g., on chromosome 1 of the genome) of said rainbow trout, said at least one SNP being located within said genome at a position corresponding to position 36 of the nucleotide sequence set forth in any one of SEQ ID NOs: 1 to 78 and SEQ ID NOs: 160 to 229, or at a position corresponding to position 36 of a nucleotide sequence which is derived from any one of SEQ ID NOs: 1 to 78 and SEQ ID NOs: 160 to 229 by 1 to 5, such as 1 to 2, nucleotide substitutions.

The rainbow trout has increased resistance to infectious pancreatic necrosis when the nucleotide of the at least one allele is a nucleotide corresponding to the IPN resistance allele of the respective SNP. The IPN resistance allele of each SNP is specified in Table 1 (and repeated in Table 2).

According to particular embodiments, the method comprises:
    determining the identity of a nucleotide of at least one allele, optionally of at least two alleles, of at least one single nucleotide polymorphism (SNP) associated with increased resistance to infectious pancreatic necrosis within the genome (e.g., on chromosome 1 of the genome) of said rainbow trout, said at least one SNP being located within said genome at a position corresponding to position 36 of the nucleotide sequence set forth in any one of SEQ ID NOs: 1 to 34 and 160 to 193, or at a position corresponding to position 36 of a nucleotide sequence which is derived from any one of SEQ ID NOs: 1 to 34 and 160 to 193 by 1 to 5, such as 1 to 2, nucleotide substitutions.

The rainbow trout has increased resistance to infectious pancreatic necrosis when the nucleotide of the at least one allele is a nucleotide corresponding to the IPN resistance allele of the respective SNP. The IPN resistance allele of each SNP is specified in Table 1.

According to other particular embodiments, the method comprises:
    determining the identity of a nucleotide of at least one allele, optionally of at least two alleles, present at a polymorphic site of at least one single nucleotide polymorphism (SNP) associated with increased resistance to infectious pancreatic necrosis within the genome (e.g., on chromosome 1 of the genome) of said rainbow trout, said at least one SNP being located within said genome at a position corresponding to position 36 of the nucleotide sequence set forth in any one of SEQ ID NOs: 1 to 18 and 160 to 162, or at a position corresponding to position 36 of a nucleotide sequence which is derived from any one of SEQ ID NOs: 1 to 18 and 160 to 162. by 1 to 5, such as 1 to 2, nucleotide substitutions.

The rainbow trout has increased resistance to infectious pancreatic necrosis when the nucleotide of the at least one allele is a nucleotide corresponding to the IPN resistance allele of the respective SNP. The IPN resistance allele of each SNP is specified in Table 1.

According to more particular embodiments, the method comprises:
    determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being located within said genome at a position corresponding to position 36 of the nucleotide sequence set forth in SEQ ID NO: 1 or SEQ ID NO: 2, or at a position corresponding to position 36 of a nucleotide sequence which is derived from SEQ ID NO: 1 or SEQ ID NO: 2 by 1 to 5, such as 1 to 2, nucleotide substitutions;
    wherein the presence of a cytosine at the position corresponding to position 36 of SEQ ID NO: 1 or the presence of a guanine at the position corresponding to position 36 of SEQ ID NO: 2 indicates that the rainbow trout has increased resistance to infectious pancreatic necrosis.

According to further more particular embodiments, the method comprises:
    determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being located within said genome at a position corresponding to position 36 of the nucleotide sequence set forth in SEQ ID NO: 160, SEQ ID NO: 161 or SEQ ID NO: 162, or at a position corresponding to position 36 of a nucleotide sequence which is derived from SEQ ID NO: 160, SEQ ID NO: 161 or SEQ ID 162 by 1 to 5, such as 1 to 2, nucleotide substitutions;

wherein the presence of a guanine at the position corresponding to position 36 of SEQ ID NO: 160, the presence of a guanine at the position corresponding to position 36 of SEQ ID NO: 161 or the presence of a cytokine at the position corresponding to position 36 SEQ ID NO:162 indicates that the rainbow trout has increased resistance to infectious pancreatic necrosis.

According to more particular embodiments, the method comprises:

determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being located within said genome at a position corresponding to position 36 of the nucleotide sequence set forth in SEQ ID NO: 1, or at a position corresponding to position 36 of a nucleotide sequence which is derived from SEQ ID NO: 1 by 1 to 5, such as 1 to 2, nucleotide substitutions;

wherein the presence of a cytosine at the position corresponding to position 36 of SEQ ID NO: 1 indicates that the rainbow trout has increased resistance to infectious pancreatic necrosis.

According to more particular embodiments, the method comprises:

determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being located within said genome at a position corresponding to position 36 of the nucleotide sequence set forth in SEQ ID NO: 2, or at a position corresponding to position 36 of a nucleotide sequence which is derived from SEQ ID NO: 2 by 1 to 5, such as 1 to 2, nucleotide substitutions;

wherein the presence of a guanine at the position corresponding to position 36 of SEQ ID NO: 2 indicates that the rainbow trout has increased resistance to infectious pancreatic necrosis.

According to further more particular embodiments, the method comprises:

determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being located within said genome at a position corresponding to position 36 of the nucleotide sequence set forth in SEQ ID NO: 160, or at a position corresponding to position 36 of a nucleotide sequence which is derived from SEQ ID NO: 160 by 1 to 5, such as 1 to 2, nucleotide substitutions;

wherein the presence of a guanine at the position corresponding to position 36 of SEQ ID NO: 160 indicates that the rainbow trout has increased resistance to infectious pancreatic necrosis.

According to further more particular embodiments, the method comprises:

determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being located within said genome at a position corresponding to position 36 of the nucleotide sequence set forth in SEQ ID NO: 161, or at a position corresponding to position 36 of a nucleotide sequence which is derived from SEQ ID NO: 161 by 1 to 5, such as 1 to 2, nucleotide substitutions;

wherein the presence of a guanine at the position corresponding to position 36 of SEQ ID NO: 161 indicates that the rainbow trout has increased resistance to infectious pancreatic necrosis.

According to further more particular embodiments, the method comprises:

determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being located within said genome at a position corresponding to position 36 of the nucleotide sequence set forth in SEQ ID NO: 162, or at a position corresponding to position 36 of a nucleotide sequence which is derived from SEQ ID NO:162 by 1 to 5, such as 1 to 2, nucleotide substitutions;

wherein the presence of a cytokine at the position corresponding to position 36 of SEQ ID NO: 162 indicates that the rainbow trout has increased resistance to infectious pancreatic necrosis.

According to certain other embodiments, the present invention provides a method for predicting increased resistance of a rainbow trout (*Oncorhynchus mykiss*) to infectious pancreatic necrosis (IPN), the method comprises:

determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being selected from the group consisting of: AX-89929954, AX-89918280, AX-89938309, AX-89960828, AX-89930342, AX-89928530, AX-89949788, AX-89928131, AX-89949832, AX-89916790, AX-89973719, AX-89962023, AX-89921280, AX-89931666, AX-89921585, AX-89953905, AX-89952945, AX-89934682, AX-89951942, AX-89937020, AX-89924837, AX-89958601, AX-89923477, AX-89959350, AX-89929482, AX-89937712, AX-89949602, AX-89925103, AX-89938051, AX-89924174, AX-89936461, AX-89916703, AX-89935317, AX-89966423, AX-89933348, AX-89969315, AX-89919958, AX-89968417, AX-89946851, AX-89976917, AX-89945446, AX-89919457, AX-89973597, AX-89938138, AX-89971866, AX-89958882, AX-89961273, AX-89944901, AX-89919465, AX-89959425, AX-89917102, AX-89959281, AX-89916766, AX-89920507, AX-89957370, AX-89934009, AX-89929663, AX-89952300, AX-89916572, AX-89946911, AX-89974593, AX-89927158, AX-89970383, AX-89965404, AX-89955634, AX-89932926, AX-89941493, AX-89943031, AX-89957682, AX-89960611, AX-89950199, AX-89928407, AX-89962035, AX-89931951, AX-89976536, AX-89916801, AX-89929085 AX-89925267, chr1_7515539, chr1_7108873, chr1_6864558, chr1_7186663, chr1_6730531, chr1_27891953, AX-89953259, chr1_6740481, chr1_6770611, chr1_7412807, chr1_7360179, chr1_7411803, chr1_7431445, chr1_7433199, chr1_7441254, chr1_7441877, chr1_7533570, chr1_6834898, chr1_6730142, chr1_6746052, chr1_6794061, chr1_7399212, chr1_7442637, chr1_7358019, chr1_7709828, chr1_7598090, chr1_7626471, chr1_7598743, chr1_7670293, chr1_7670561, chr1_7647634, chr1_7356089, chr1_8109044, chr1_10439048, chr1_8142346, chr1_8092208, chr1_8138683, chr1_8139206, chr1_8139744, chr1_8140789, chr1_8141687, chr1_8154917, chr1_7454708, chr1_7504847, chr1_7505686, chr1_7505817, chr1_8202031, chr1_8228173, chr1_8309469, chr1_8163977, chr1_27786931, chr1_8194629, chr1_7505259, chr1_8474659, chr1_8282602, chr1_8306806, chr1_8341618, chr1_8343786, chr1_8345836, chr1_8350569, chr1_8402403, AX-89962103, chr1_8279302, chr1_8334901, chr1_7561600, AX-89956272, chr1_7938827, chr1_10810229, chr1_11007071 and chr1_10884171.

The rainbow trout has increased resistance to infectious pancreatic necrosis when the nucleotide of the at least one allele is a nucleotide corresponding to the IPN resistance allele of the respective SNP. The IPN resistance allele of each SNP is specified in Table 1.

According to particular embodiments, the method comprises:
determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being selected from the group consisting of: AX-89929954, AX-89918280, AX-89938309, AX-89960828, AX-89930342, AX-89928530, AX-89949788, AX-89928131, AX-89949832, AX-89916790, AX-89973719, AX-89962023, AX-89921280, AX-89931666, AX-89921585, AX-89953905, AX-89952945, AX-89934682, AX-89951942, AX-89937020, AX-89924837, AX-89958601, AX-89923477, AX-89959350, AX-89929482, AX-89937712, AX-89949602, AX-89925103, AX-89938051, AX-89924174, AX-89936461, AX-89916703, AX-89935317 and AX-89966423.

The rainbow trout has increased resistance to infectious pancreatic necrosis when the nucleotide of the at least one allele is a nucleotide corresponding to the IPN resistance allele of the respective SNP. The IPN resistance allele of each SNP is specified in Table 1.

According to particular embodiments, the method comprises:
determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being selected from the group consisting of: AX-89929954, AX-89918280, AX-89938309, AX-89960828, AX-89930342, AX-89928530, AX-89949788, AX-89928131, AX-89949832, AX-89916790, AX-89973719, AX-89962023, AX-89921280, AX-89931666, AX-89921585, AX-89953905, AX-89952945 and AX-89934682.

The rainbow trout has increased resistance to infectious pancreatic necrosis when the nucleotide of the at least one allele is a nucleotide corresponding to the IPN resistance allele of the respective SNP. The IPN resistance allele of each SNP is specified in Table 1.

According to more particular embodiments, the method comprises:
determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being AX-89929954 or AX-89918280;
wherein the presence of a cytosine at the position of AX-89929954 or a guanine at the position of AX-89918280 indicates that the rainbow trout has increased resistance to infectious pancreatic necrosis.

According to more particular embodiments, the method comprises:
determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being AX-89929954;
wherein the presence of a cytosine at the position of AX-89929954 indicates that the rainbow trout has increased resistance to infectious pancreatic necrosis.

According to more particular embodiments, the method comprises:
determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being AX-89918280;
wherein the presence of a guanine at the position of AX-89918280 indicates that the rainbow trout has increased resistance to infectious pancreatic necrosis.

According to further particular embodiments, the method comprises:
determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being selected from the group consisting of: chr1_7515539, chr1_7108873, chr1_6864558chr1_7186663, chr1_6730531, chr1_27891953, AX-89953259, chr1_6740481, chr1_6770611, chr1_7412807, chr1_7360179, chr1_7411803, chr1_7431445, chr1_7433199, chr1_7441254, chr1_7441877, chr1_7533570, chr1_6834898, chr1_6730142, chr1_6746052, chr1_6794061, chr1_7399212, chr1_7442637, chr1_7358019, chr1_7709828, chr1_7598090, chr1_7626471, chr1_7598743, chr1_7670293, chr1_7670561, chr1_7647634, chr1_7356089, chr1_8109044, and chr1 10439048.

The rainbow trout has increased resistance to infectious pancreatic necrosis when the nucleotide of the at least one allele is a nucleotide corresponding to the IPN resistance allele of the respective SNP. The IPN resistance allele of each SNP is specified in Table 1.

According to more particular embodiments, the method comprises:

determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being chr1_7515539, chr1_7108873 or chr1_6864558, wherein the presence of a guanine at the position of chr1_7515539, a guanine at the position of chr1_7108873 or a cytokine chr1_6864558 indicates that the rainbow trout has increased resistance to infectious pancreatic necrosis.

According to further more particular embodiments, the method comprises:

determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being chr1_7515539;

wherein the presence of a guanine at the position of chr1_7515539 indicates that the rainbow trout has increased resistance to infectious pancreatic necrosis.

According to more particular embodiments, the method comprises:

determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being chr1_7108873;

wherein the presence of a guanine at the position of chr1_7108873 indicates that the rainbow trout has increased resistance to infectious pancreatic necrosis.

According to more particular embodiments, the method comprises:

determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being chr1_6864558;

wherein the presence of a cytokine at the position of chr1_6864558 indicates that the rainbow trout has increased resistance to infectious pancreatic necrosis.

The methods for predicting increased resistance of a rainbow trout to IPN may involve determining the identity of a nucleotide present of at least one allele of more than one SNP, such as at least two, at least three or at least 4 SNPs. The prediction may then be based on the presence of the IPN resistance alleles for the SNPs analysed. For example, one may genotype at least SNPs AX-89929954 (SNP #1) and AX-89918280 (SNP #2). One may also genotype at least SNPs AX-89929954 (SNP #1), AX-89918280 (SNP #2) and AX-89938309 (SNP #3). One may also genotype at least SNPs AX-89929954 (SNP #1), AX-89918280 (SNP #2), AX-89938309 (SNP #3), AX-89960828 (SNP #4) and chr_1 7515539 (SNP #160).

The present invention provides in a further aspect a method for selecting a rainbow trout having increased resistance to infectious pancreatic necrosis. Particularly, the present invention provides a method for selecting a rainbow trout having increased resistance to infectious pancreatic necrosis, the method comprises:

determining the presence of at least one (such as at least two) allele conferring IPN resistance ("IPN resistance allele") within the genome (e.g., on chromosome 1 of the genome) of said rainbow trout; and selecting said rainbow trout as having increased resistance when the at least one IPN resistance allele is present.

According to certain embodiments, the at least one IPN resistance allele is an allele of at least one polymorphism, such as at least one single nucleotide polymorphism (SNP).

According to certain embodiments, the at least one SNP is selected from the SNPs listed in Table 1.

According to certain embodiments, the present invention provides a method for selecting a rainbow trout having increased resistance to infectious pancreatic necrosis, the method comprises:

determining the identity of a nucleotide of at least one allele, optionally of at least two alleles, of at least one single nucleotide polymorphism (SNP) associated with increased resistance to infectious pancreatic necrosis within the genome (e.g., on chromosome 1 of the genome) of said rainbow trout, said at least one SNP being located within said genome at a position corresponding to position 36 of the nucleotide sequence set forth in any one of SEQ ID NOs: 1 to 78 and SEQ ID NOs: 160 to 229, or at a position corresponding to position 36 of a nucleotide sequence which is derived from any one of SEQ ID NOs: 1 to 78 and SEQ ID NOs: 160 to 229 by 1 to 5, such as 1 to 2, nucleotide substitutions; and selecting said rainbow trout as having increased resistance when the nucleotide of the at least one allele is a nucleotide corresponding to the IPN resistance allele of the respective SNP. The IPN resistance allele of each SNP is specified in Table 1.

According to particular embodiments, the method comprises:

determining the identity of a nucleotide of at least one allele, optionally of at least two alleles, of at least one single nucleotide polymorphism (SNP) associated with increased resistance to infectious pancreatic necrosis within the genome (e.g., on chromosome 1 of the genome) of said rainbow trout, said at least one SNP being located within said genome at a position corresponding to position 36 of the nucleotide sequence set forth in any one of SEQ ID NOs: 1 to 34, or at a position corresponding to position 36 of a nucleotide sequence which is derived from any one of SEQ ID NOs: 1 to 34 by 1 to 5, such as 1 to 2, nucleotide substitutions; and selecting said rainbow trout as having increased resistance when the nucleotide of the at least one allele is a nucleotide corresponding to the IPN resistance allele of the respective SNP. The IPN resistance allele of each SNP is specified in Table 1.

According to further particular embodiments, the method comprises:

determining the identity of a nucleotide of at least one allele, optionally of at least two alleles, of at least one single nucleotide polymorphism (SNP) associated with increased resistance to infectious pancreatic necrosis within the genome (e.g., on chromosome 1 of the genome) of said rainbow trout, said at least one SNP being located within said genome at a position corresponding to position 36 of the nucleotide sequence set forth in any one of SEQ ID NOs: 160 to 193, or at a position corresponding to position 36 of a nucleotide sequence which is derived from any one of SEQ ID NOs: 160 to 193 by 1 to 5, such as 1 to 2, nucleotide substitutions; and selecting said rainbow trout as having increased resistance when the nucleotide of the at least one allele is a nucleotide corresponding to the IPN resistance allele of the respective SNP. The IPN resistance allele of each SNP is specified in Table 1.

According to particular embodiments, the method comprises:

determining the identity of a nucleotide of at least one allele, optionally of at least two alleles, of at least one single nucleotide polymorphism (SNP) associated with increased resistance to infectious pancreatic necrosis within the genome (e.g., on chromosome 1 of the genome) of said rainbow trout, said at least one SNP being located within said genome at a position corresponding to position 36 of the nucleotide sequence set forth in any one of SEQ ID NOs: 1 to 18, or at a position corresponding to position 36 of a nucleotide sequence which is derived from any one of SEQ ID NOs: 1 to 18 by 1 to 5, such as 1 to 2, nucleotide substitutions; and selecting said rainbow trout as having increased resistance when the nucleotide of the at least one allele is a nucleotide corresponding to the IPN resistance allele of the respective SNP. The IPN resistance allele of each SNP is specified in Table 1.

According to further particular embodiments, the method comprises:

determining the identity of a nucleotide of at least one allele, optionally of at least two alleles, of at least one single nucleotide polymorphism (SNP) associated with increased resistance to infectious pancreatic necrosis within the genome (e.g., on chromosome 1 of the genome) of said rainbow trout, said at least one SNP being located within said genome at a position corresponding to position 36 of the nucleotide sequence set forth in any one of SEQ ID NOs: 160 to 162, or at a position corresponding to position 36 of a nucleotide sequence which is derived from any one of SEQ ID NOs: 160 to 162 by 1 to 5, such as 1 to 2, nucleotide substitutions; and selecting said rainbow trout as having increased resistance when the nucleotide of the at least one allele is a nucleotide corresponding to the IPN resistance allele of the respective SNP. The IPN resistance allele of each SNP is specified in Table 1.

According to more particular embodiments, the method comprises:

determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being located within said genome at a position corresponding to position 36 of the nucleotide sequence set forth in SEQ ID NO: 1 or SEQ ID NO: 2, or at a position corresponding to position 36 of a nucleotide sequence which is derived from SEQ ID NO: 1 or SEQ ID NO: 2 by 1 to 5, such as 1 to 2, nucleotide substitutions; and selecting said rainbow trout as having increased resistance to infectious pancreatic necrosis when a cytosine is present at the position corresponding to position 36 of SEQ ID NO: 1 or a guanine is present at the position corresponding to position 36 of SEQ ID NO: 2.

According to further more particular embodiments, the method comprises:

determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being located within said genome at a position corresponding to position 36 of the nucleotide sequence set forth in SEQ ID NO: 160, SEQ ID NO:161 or SEQ ID NO: 162, or at a position corresponding to position 36 of a nucleotide sequence which is derived from SEQ ID NO: 160, SEQ ID NO:161 or SEQ ID NO: 162 by 1 to 5, such as 1 to 2, nucleotide substitutions; and selecting said rainbow trout as having increased resistance to infectious pancreatic necrosis when a guanine is present at the position corresponding to position 36 of SEQ ID NO: 160, guanine is present at the position corresponding to position 36 of SEQ ID NO: 161 or a cytokine is present at the position corresponding to position 36 of SEQ ID NO: 162.

According to more particular embodiments, the method comprises:

determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being located within said genome at a position corresponding to position 36 of the nucleotide sequence set forth in SEQ ID NO: 1, or at a position corresponding to position 36 of a nucleotide sequence which is derived from SEQ ID NO: 1 by 1 to 5, such as 1 to 2, nucleotide substitutions; and selecting said rainbow trout as having increased resistance to infectious pancreatic necrosis when a cytosine is present at the position corresponding to position 36 of SEQ ID NO: 1.

According to more particular embodiments, the method comprises:

determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being located within said genome at a position corresponding to position 36 of the nucleotide sequence set forth in SEQ ID NO: 1 or SEQ ID NO: 2, or at a position corresponding to position 36 of a nucleotide sequence which is derived from SEQ ID NO: 2 by 1 to 5, such as 1 to 2, nucleotide substitutions; and selecting said rainbow trout as having increased resistance to infectious pancreatic necrosis when a guanine is present at the position corresponding to position 36 of SEQ ID NO: 2.

According to other certain embodiments, the present invention provides a method for selecting a rainbow trout having increased resistance to infectious pancreatic necrosis, the method comprises:

determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being selected from the group consisting of: AX-89929954, AX-89918280, AX-89938309, AX-89960828, AX-89930342, AX-89928530, AX-89949788, AX-89928131, AX-89949832, AX-89916790, AX-89973719, AX-89962023, AX-89921280, AX-89931666, AX-89921585, AX-89953905, AX-89952945, AX-89934682, AX-89951942, AX-89937020, AX-89924837, AX-89958601, AX-89923477, AX-89959350, AX-89929482, AX-89937712, AX-89949602, AX-89925103, AX-89938051, AX-89924174, AX-89936461, AX-89916703, AX-89935317, AX-89966423, AX-89933348, AX-89969315, AX-89919958, AX-89968417, AX-89946851, AX-89976917, AX-89945446, AX-89919457, AX-89973597, AX-89938138, AX-89971866, AX-89958882, AX-89961273, AX-89944901, AX-89919465, AX-89959425, AX-89917102, AX-89959281, AX-89916766, AX-89920507, AX-89957370, AX-89934009, AX-89929663, AX-89952300, AX-89916572, AX-89946911, AX-89974593, AX-89927158, AX-89970383, AX-89965404, AX-89955634, AX-89932926, AX-89941493, AX-89943031, AX-89957682, AX-89960611, AX-89950199, AX-89928407, AX-89952035, AX-89931951, AX-89976536, AX-89916801, AX-89929085, AX-89925267; and chr1_7515539, chr1_7108873, chr1_6864558, chr1_7186663, chr1_6730531, chr1_27891953, AX-89953259, chr1_6740481, chr1_6770611, chr1_7412807, chr1_7360179, chr1_7411803, chr1_7431445, chr1_7433199, chr1_7441254, chr1_7441877, chr1_7533570, chr1_6834898, chr1_6730142, chr1_6746052, chr1_6794061, chr1_7399212, chr1_7442637, chr1_7358019, chr1_7709828, chr1_7598090, chr1_7626471, chr1_7598743, chr1_7670293, chr1_7670561, chr1_7647634, chr1_7356089, chr1_8109044, chr1_10439048, chr1_8142346, chr1_8092208, chr1_8138683, chr1_8139206, chr1_8139744, chr1_8140789, chr1_8141687, chr1_8154917, chr1_7454708, chr1_7504847, chr1_7505686, chr1_7505817, chr1_8202031, chr1_8228173, chr1_8309469, chr1_8163977, chr1_27786931, chr1_8194629, chr1_7505259, chr1_8474659, chr1_8282602, chr1_8306806, chr1_8341618, chr1_8343786, chr1_8345836, chr1_8350569, chr1_8402403, AX-89962103, chr1_8279302, chr1_8334901, chr1_7561600, AX-89956272, chr1_7938827, chr1_10810229, chr1_11007071 and chr1_10884171.

selecting said rainbow trout as having increased resistance when the nucleotide of the at least one allele is a nucleotide corresponding to the IPN resistance allele of the respective SNP. The IPN resistance allele of each SNP is specified in Table 1.

According to particular embodiments, the method comprises:
determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being selected from the group consisting of: AX-89929954, AX-89918280, AX-89938309, AX-89960828, AX-89930342, AX-89928530, AX-89949788, AX-89928131, AX-89949832, AX-89916790, AX-89973719, AX-89962023, AX-89921280, AX-89931666, AX-89921585, AX-89953905, AX-89952945, AX-89934682, AX-89951942, AX-89937020, AX-89924837, AX-89958601, AX-89923477, AX-89959350, AX-89929482, AX-89937712, AX-89949602, AX-89925103, AX-89938051, AX-89924174, AX-89936461, AX-89916703, AX-89935317 and AX-89966423; and selecting said rainbow trout as having increased resistance when the nucleotide of the at least one allele is a nucleotide corresponding to the IPN resistance allele of the respective SNP. The IPN resistance allele of each SNP is specified in Table 1.

According to other particular embodiments, the method comprises:
determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being selected from the group consisting of:
AX-89929954, AX-89918280, AX-89938309, AX-89960828, AX-89930342, AX-89928530, AX-89949788, AX-89928131, AX-89949832, AX-89916790, AX-89973719, AX-89962023, AX-89921280, AX-89931666, AX-89921585, AX-89953905, AX-89952945 and AX-89934682; and selecting said rainbow trout as having increased resistance when the nucleotide of the at least one allele is a the IPN resistance allele of the respective SNP. The IPN resistance allele of each SNP is specified in Table 1.

According to further particular embodiments, the method comprises:
determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being selected from the group consisting of: 7515539, chr1_7108873, chr1_6864558, chr1_7186663, chr1_6730531, chr1_27891953, AX-89953259, chr1_6740481, chr1_6770611, chr1_7412807, chr1_7360179, chr1_7411803, chr1_7431445, chr1_7433199, chr1_7441254, chr1_7441877, chr1_7533570, chr1_6834898, chr1_6730142, chr1_6746052, chr1_6794061, chr1_7399212, chr1_7442637, chr1_7358019, chr1_7709828, chr1_7598090, chr1_7626471, chr1_7598743, chr1_7670293, chr1_7670561, chr1_7647634, chr1_7356089, chr1_8109044, and chr1 10439048 and selecting said rainbow trout as having increased resistance when the nucleotide of the at least one allele is a the IPN resistance allele of the respective SNP. The IPN resistance allele of each SNP is specified in Table 1.

According to further other particular embodiments, the method comprises:
determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being selected from the group consisting of: chr1 7515539, chr1_7108873 and chr1_6864558 selecting said rainbow trout as having increased resistance when the nucleotide of the at least one allele is a the IPN resistance allele of the respective SNP. The IPN resistance allele of each SNP is specified in Table 1.

According to more particular embodiments, the method comprises:
determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being AX-89929954 or AX-89918280; and
selecting said rainbow trout as having increased resistance to infectious pancreatic necrosis when a cytosine is present at the position of AX-89929954 or a guanine is present at the position of AX-89918280.

According to more particular embodiments, the method comprises:
determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being AX-89929954; and
selecting said rainbow trout as having increased resistance to infectious pancreatic necrosis when a cytosine is present at the position of AX-89929954.

According to more particular embodiments, the method comprises:
determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being AX-89918280; and
selecting said rainbow trout as having increased resistance to infectious pancreatic necrosis when a guanine is present at the position of AX-89918280.

According to further more particular embodiments, the method comprises:
determining the identity of a nucleotide of at least one allele, optionally of at least two alleles, of at least one single nucleotide polymorphism (SNP) associated with infectious pancreatic necrosis within the genome (e.g., on chromosome 1 of the genome) of said rainbow trout, said at least one SNP being chr1-7515539, chr1_7108873 or chr1_6864558; and
selecting said rainbow trout as having increased resistance to infectious pancreatic necrosis when a guanine is present at the position of chr1 7515539, a guanine is present at the position of chr1_7108873 or a cytokine is present at the position of chr1_6864558.

The methods for selecting a rainbow trout having increased resistance to infectious pancreatic necrosis may involve determining the identity of a nucleotide of at least one allele of more than one SNP, such as at least two, at least three or at least 4 SNPs. The selection may then be based on the presence of the IPN resistance alleles for the SNPs analysed. For example, one may genotype at least SNPs AX-89929954 (SNP #1) and AX-89918280 (SNP #2). One may also genotype at least SNPs AX-89929954 (SNP #1), AX-89918280 (SNP #2) and AX-89938309 (SNP #3). One may also genotype at least SNPs AX-89929954 (SNP #1), AX-89918280 (SNP #2), AX-89938309 (SNP #4), AX-89960828 (SNP #4) and chr1_7515539 (SNP #160).

Numerous techniques are known in the art for determining the identity of a nucleotide of an allele present at a polymorphic site. For example, the determination may involve sequence analysis of the rainbow trout to be tested using, e.g., traditional sequence methodologies (e.g., the "dideoxy-mediated chain termination method, "also known as the "Sanger Method" (Sanger, F., et al., J. Molec. Biol. 94: 441 (1975); Prober et al. Science 238: 336-340 (1987)) and the "chemical degradation method" also known as the "Maxam-Gilbert method" (Maxam, A. M., et al., Proc. Natl. Acad. Sci. (U.S.A.) 74: 560 (1977). Alternatively, the determination may involve single base extension of DNA oligonucleotides terminating at the polymorphic site (e.g. iPLEX assays from Sequenom (San Diego, USA) and Infinium assays from Illumina (San Diego, USA), allele-specific ligation assays (e.g. Axiom technology from Affymetrix (San Diego, USA), allele-specific PCR (e.g. SNPtype assays from Fluidigm (San Francisco) or KASP assays from LGC Genomics (Teddington, UK)), or competitive hybridisation of probes complementary to the different alleles (e.g. the TaqMan assay from Applied Biosystems (Foster City, USA)).

Methods for the detection of allelic variation are also reviewed by Nollau et al., Clin. Chem. 43, 1114-1120, 1997; and in standard textbooks, for example "Laboratory Protocols for Mutation Detection", Ed. by U. Landegren, Oxford University Press, 1996 and "PCR", 2nd Edition by Newton & Graham, BIOS Scientific Publishers Limited, 1997.

For analyzing SNPs, it may for example be appropriate to use oligonucleotides specific for alternative SNP alleles. Such oligonucleotides which detect single nucleotide variations in target sequences may be referred to by such terms as "allele-specific oligonucleotides", "allele-specific probes", or "allele-specific primers". The design and use of allele-specific probes for analyzing polymorphisms is described in, e.g., Mutation Detection A Practical Approach, ed. Cotton et al. Oxford University Press, 1998; Saiki et al., Nature 324, 163-166 (1986); Dattagupta, EP235726; and Saiki, WO 89/11548.

Rainbow Trout of the Invention

The present invention provides in a further aspect a rainbow trout, such as an isolated rainbow trout, having increased resistance to infectious pancreatic necrosis. Particularly, the present invention provides a rainbow trout or progeny thereof comprising within its genome (e.g., on chromosome 1 of its genome) at least one allele conferring IPN resistance ("IPN resistance allele").

According to certain embodiments, the at least one IPN resistance allele is an allele of at least one polymorphism, such as at least one single nucleotide polymorphism (SNP).

According to certain embodiments, the at least one SNP is selected from the SNPs listed in Table 1.

According to certain embodiments, the at least one SNP is selected from the group consisting of: AX-89929954, AX-89918280, AX-89938309, AX-89960828, AX-89930342, AX-89928530, AX-89949788, AX-89928131, AX-89949832, AX-89916790, AX-89973719, AX-89962023, AX-89921280, AX-89931666, AX-89921585, AX-89953905, AX-89952945, AX-89934682, AX-89951942, AX-89937020, AX-89924837, AX-89958601, AX-89923477, AX-89959350, AX-89929482, AX-89937712, AX-89949602, AX-89925103, AX-89938051, AX-89924174, AX-89936461, AX-89916703, AX-89935317, AX-89966423, AX-89933348, AX-89969315, AX-89919958, AX-89968417, AX-89946851, AX-89976917, AX-89945446, AX-89919457, AX-89973597, AX-89938138, AX-89971866, AX-89958882, AX-89961273, AX-89944901, AX-89919465, AX-89959425, AX-89917102, AX-89959281, AX-89916766, AX-89920507, AX-89957370, AX-89934009, AX-89929663, AX-89952300, AX-89916572, AX-89946911, AX-89974593, AX-89927158, AX-89970383, AX-89965404, AX-89955634, AX-89932926, AX-89941493, AX-89943031, AX-89957682, AX-89960611, AX-89950199, AX-89928407, AX-89962035, AX-89931951, AX-89976536, AX-89916801, AX-89929085, AX-89925267, chr1_7515539, chr1_7108873, chr1_6864558, chr1_7186663, chr1_6730531, chr1_27891953, AX-89953259, chr1_6740481, chr1_6770611, chr1_7412807, chr1_7360179, chr1_7411803, chr1_7431445, chr1_7433199, chr1_7441254, chr1_7441877, chr1_7533570, chr1_6834898, chr1_6730142, chr1_6746052, chr1_6794061, chr1_7399212, chr1_7442637, chr1_7358019, chr1_7709828, chr1_7598090, chr1_7626471, chr1_7598743, chr1_7670293, chr1_7670561, chr1_7647634, chr1_7356089, chr1_8109044, chr1_10439048, chr1_8142346, chr1_8092208, chr1_8138683, chr1_8139206, chr1_8139744, chr1_8140789, chr1_8141687, chr1_8154917, chr1_7454708, chr1_7504847, chr1_7505686, chr1_7505817, chr1_8202031, chr1_8228173, chr1_8309469, chr1_8163977, chr1_27786931, chr1_8194629, chr1_7505259, chr1_8474659, chr1_8282602, chr1_8306806, chr1_8341618, chr1_8343786, chr1_8345836, chr1_8350569, chr1_8402403, AX-89962103, chr1_8279302, chr1_8334901, chr1_7561600, AX-89956272, chr1_7938827, chr1_10810229, chr1_11007071 and chr1_10884171.

According to particular embodiments, the at least one SNP is selected from the group consisting of: AX-89929954, AX-89918280, AX-89938309, AX-89960828, AX-89930342, AX-89928530, AX-89949788, AX-89928131, AX-89949832, AX-89916790, AX-89973719, AX-89962023, AX-89921280, AX-89931666, AX-89921585, AX-89953905, AX-89952945, AX-89934682, AX-89951942, AX-89937020, AX-89924837, AX-89958601, AX-89923477, AX-89959350, AX-89929482, AX-89937712, AX-89949602, AX-89925103, AX-89938051, AX-89924174, AX-89936461, AX-89916703, AX-89935317 and AX-89966423.

According to other particular embodiments, the at least one SNP is selected from the group consisting of: AX-89929954, AX-89918280, AX-89938309, AX-89960828, AX-89930342, AX-89928530, AX-89949788, AX-89928131, AX-89949832, AX-89916790, AX-89973719, AX-89962023, AX-89921280, AX-89931666, AX-89921585, AX-89953905, AX-89952945 and AX-89934682.

According to more particular embodiments, the at least one SNP is AX-89929954 or AX-89918280.

According to other more particular embodiments, the at least one SNP is AX-89929954.

According to other more particular embodiments, the at least one SNP is AX-89918280.

According to further other more particular embodiments, the at least one SNP is chr1_7515539, chr1_7108873, chr1_6864558, chr1_7186663, chr1_6730531, chr1_27891953, AX-89953259, chr1_6740481, chr1_6770611, chr1_7412807, chr1_7360179, chr1_7411803, chr1_7431445, chr1_7433199, chr1_7441254, chr1_7441877, chr1_7533570, chr1_6834898, chr1_6730142, chr1_6746052, chr1_6794061, chr1_7399212, chr1_7442637, chr1_7358019, chr1_7709828, chr1_7598090, chr1_7626471, chr1_7598743, chr1_7670293, chr1_7670561, chr1_7647634, chr1_7356089, chr1_8109044, and chr1 10439048.

According to other more particular embodiments, the at least one SNP is chr1 7515539, chr1_7108873 and chr1_6864558.

According to further other more particular embodiments, the at least one SNP is chr1_7515539.

According to further other more particular embodiments, the at least one SNP is chr1_7108873.

According to further other more particular embodiments, the at least one SNP is chr1_6864558.

According to certain embodiments, the rainbow trout or progeny thereof, such as an isolated rainbow trout or progeny thereof, comprises within its genome (e.g., on chromosome 1 of its genome) at least one nucleotide sequence selected from the group consisting of a) the nucleotide sequences set forth in SEQ ID NOs: 79 to 156, and 230 to 299 and b) nucleotide sequences derived from any one of SEQ ID NOs: 79 to 156 and 230 to 299 by 1 to 5, such as 1 to 2, nucleotide substitutions, provide that said nucleotide substitutions are not at position 36 of said derived sequence.

According to particular embodiments, the rainbow trout or progeny thereof, such as an isolated rainbow trout or progeny thereof, comprises within its genome (e.g., on chromosome 1 of its genome) at least one nucleotide sequence selected from the group consisting of a) the nucleotide sequences set forth in SEQ ID NOs: 79 to 112, and b) nucleotide sequences derived from any one of SEQ ID NOs: 79 to 112 by 1 to 5, such as 1 to 2, nucleotide substitutions, provide that said nucleotide substitutions are not at position 36 of said derived sequence.

According to other particular embodiments, the rainbow trout or progeny thereof, such as an isolated rainbow trout or progeny thereof, comprises within its genome (e.g., on chromosome 1 of its genome) at least one nucleotide sequence selected from the group consisting of a) the nucleotide sequences set forth in SEQ ID NOs: 79 to 96, and b) nucleotide sequences derived from any one of SEQ ID NOs: 79 to 96 by 1 to 5, such as 1 to 2, nucleotide substitutions, provide that said nucleotide substitutions are not at position 36 of said derived sequence.

According to more particular embodiments, the rainbow trout or progeny thereof, such as an isolated rainbow trout or progeny thereof, comprises within its genome (e.g., on chromosome 1 of its genome) at least one nucleotide sequence selected from the group consisting of a) the nucleotide sequences set forth in SEQ ID NO: 79 and SEQ ID NO: 80, and b) nucleotide sequences derived from any one of SEQ ID NO: 79 and SEQ ID NO: 80 by 1 to 5, such as 1 to 2, nucleotide substitutions, provided that said nucleotide substitutions are not at position 36 of said derived sequence.

According to other more particular embodiments, the rainbow trout or progeny thereof, such as an isolated rainbow trout or progeny thereof, comprises within its genome (e.g., on chromosome 1 of its genome) at least one nucleotide sequence selected from the group consisting of a) the nucleotide sequence set forth in SEQ ID NO: 79 and b) nucleotide sequences derived from SEQ ID NO: 79 by 1 to 5, such as 1 to 2, nucleotide substitutions, provided that said nucleotide substitutions are not at position 36 of said derived sequence.

According to other more particular embodiments, the rainbow trout or progeny thereof, such as an isolated rainbow trout or progeny thereof, comprises within its genome (e.g., on chromosome 1 of its genome) at least one nucleotide sequence selected from the group consisting of a) the nucleotide sequence set forth in SEQ ID NO: 80, and b) nucleotide sequences derived from SEQ ID NO: 80 by 1 to 5, such as 1 to 2, nucleotide substitutions, provided that said nucleotide substitutions are not at position 36 of said derived sequence.

According to further particular embodiments, the rainbow trout or progeny thereof, such as an isolated rainbow trout or progeny thereof, comprises within its genome (e.g., on chromosome 1 of its genome) at least one nucleotide sequence selected from the group consisting of a) the nucleotide sequences set forth in SEQ ID NOs: 230 to 263, and b) nucleotide sequences derived from any one of SEQ ID NOs: 230 to 263 by 1 to 5, such as 1 to 2, nucleotide substitutions, provide that said nucleotide substitutions are not at position 36 of said derived sequence.

According to further more particular embodiments, the rainbow trout or progeny thereof, such as an isolated rainbow trout or progeny thereof, comprises within its genome (e.g., on chromosome 1 of its genome) at least one nucleotide sequence selected from the group consisting of a) the nucleotide sequences set forth in SEQ ID NOs: 230 to 232 and b) nucleotide sequences derived from any one of SEQ ID NOs: 230 to 232 by 1 to 5, such as 1 to 2, nucleotide substitutions, provided that said nucleotide substitutions are not at position 36 of said derived sequence.

According to further other more particular embodiments, the rainbow trout or progeny thereof, such as an isolated rainbow trout or progeny thereof, comprises within its genome (e.g., on chromosome 1 of its genome) at least one nucleotide sequence selected from the group consisting of a) the nucleotide sequence set forth in SEQ ID NO: 230 and b) nucleotide sequences derived from SEQ ID NO: 230 by 1 to 5, such as 1 to 2, nucleotide substitutions, provided that said nucleotide substitutions are not at position 36 of said derived sequence.

According to further other more particular embodiments, the rainbow trout or progeny thereof, such as an isolated rainbow trout or progeny thereof, comprises within its genome (e.g., on chromosome 1 of its genome) at least one nucleotide sequence selected from the group consisting of a) the nucleotide sequence set forth in SEQ ID NO: 231, and b) nucleotide sequences derived from SEQ ID NO: 231 by 1 to 5, such as 1 to 2, nucleotide substitutions, provided that said nucleotide substitutions are not at position 36 of said derived sequence.

According to further other more particular embodiments, the rainbow trout or progeny thereof, such as an isolated rainbow trout or progeny thereof, comprises within its genome (e.g., on chromosome 1 of its genome) at least one nucleotide sequence selected from the group consisting of a) the nucleotide sequence set forth in SEQ ID NO: 232, and b) nucleotide sequences derived from SEQ ID NO: 232 by 1 to 5, such as 1 to 2, nucleotide substitutions, provided that said nucleotide substitutions are not at position 36 of said derived sequence According to certain embodiments, the rainbow trout is a female.

According to certain other embodiments, the rainbow trout is a male.

According to certain embodiments, the rainbow trout or progeny thereof is obtained by a method according to the present invention.

In one further aspect of the present invention, a rainbow trout or progeny thereof comprises in its genome at least one allele conferring IPN resistance obtainable by a process comprising the steps of:
a) genotyping the trout,
b) selecting individuals having at least one allele preferably two alleles conferring IPN resistance ("IPN resistance allele"); and
c) mating individuals in such a way that at least one individual within each mated pair has two alleles conferring IPN resistance According to certain embodiments the mating in c) may also be conducted in such a way that the mated pair each has two alleles conferring IPN resistance, or that each mated pair has one allele conferring IPN resistance.

According to certain embodiments the rainbow trout or progeny thereof obtained by the process, the at least one IPN resistance allele may be an allele of at least one single nucleotide polymorphism (SNP).

According to further certain embodiments the rainbow trout or progeny thereof obtained by the process, the at least one SNP may be selected from the SNPs listed in Table 1.

According to more certain embodiments the rainbow trout or progeny thereof obtained by the process, comprises within its genome at least one nucleotide sequence selected from the group consisting of a) the nucleotide sequences set forth in SEQ ID NOs: 79 to 156 and 230 to 299 and b) nucleotide sequences derived from any one of SEQ ID NOs: 79 to 156 and 230 to 299 by 1 to 5, such as 1 to 2, nucleotide substitutions, provide that said nucleotide substitutions are not at position 36 of said derived sequence.

According to certain embodiments, the rainbow trout is a female.

According to certain other embodiments, the rainbow trout is a male.

The present invention provides in a further aspect a population of rainbow trouts, such as an isolated population, each individual within the population having increased resistance to infectious pancreatic necrosis. Particularly, the present invention provides a population of rainbow trouts, each individual within the population comprising within its genome at least one allele conferring IPN resistance ("IPN resistance allele").

According to certain embodiments, the at least one IPN resistance allele is an allele of at least one polymorphism, such as at least one single nucleotide polymorphism (SNP).

According to certain embodiments, the at least one SNP is selected from the SNPs listed in Table 1.

According to certain embodiments, the at least one SNP is selected from the group consisting of: AX-89929954, AX-89918280, AX-89938309, AX-89960828, AX-89930342, AX-89928530, AX-89949788, AX-89928131, AX-89949832, AX-89916790, AX-89973719, AX-89962023, AX-89921280, AX-89931666, AX-89921585, AX-89953905, AX-89952945, AX-89934682, AX-89951942, AX-89937020, AX-89924837, AX-89958601, AX-89923477, AX-89959350, AX-89929482, AX-89937712, AX-89949602, AX-89925103, AX-89938051, AX-89924174, AX-89936461, AX-89916703, AX-89935317, AX-89966423, AX-89933348, AX-89969315, AX-89919958, AX-89968417, AX-89946851, AX-89976917, AX-89945446, AX-89919457, AX-89973597, AX-89938138, AX-89971866, AX-89958882, AX-89961273, AX-89944901, AX-89919465, AX-89959425, AX-89917102, AX-89959281, AX-89916766, AX-89920507, AX-89957370, AX-89934009, AX-89929663, AX-89952300, AX-89916572, AX-89946911, AX-89974593, AX-89927158, AX-89970383, AX-89965404, AX-89955634, AX-89932926, AX-89941493, AX-89943031, AX-89957682, AX-89960611, AX-89950199, AX-89928407, AX-89962035, AX-89931951, AX-89976536, AX-89916801, AX-89929085, AX-89925267, chr1_7515539, chr1_7108873, chr1_6864558, chr1_7186663, chr1_6730531, chr1_27891953, AX-89953259, chr1_6740481, chr1_6770611, chr1_7412807, chr1_7360179, chr1_7411803, chr1_7431445, chr1_7433199, chr1_7441254, chr1_7441877, chr1_7533570, chr1_6834898, chr1_6730142, chr1_6746052, chr1_6794061, chr1_7399212, chr1_7442637, chr1_7358019, chr1_7709828, chr1_7598090, chr1_7626471, chr1_7598743, chr1_7670293, chr1_7670561, chr1_7647634, chr1_7356089, chr1_8109044, chr1_10439048, chr1_8142346, chr1_8092208, chr1_8138683, chr1_8139206, chr1_8139744, chr1_8140789, chr1_8141687, chr1_8154917, chr1_7454708, chr1_7504847, chr1_7505686, chr1_7505817, chr1_8202031, chr1_8228173, chr1_8309469, chr1_8163977, chr1_27786931, chr1_8194629, chr1_7505259, chr1_8474659, chr1_8282602, chr1_8306806, chr1_8341618, chr1_8343786, chr1_8345836, chr1_8350569, chr1_8402403, AX-89962103, chr1_8279302, chr1_8334901, chr1_7561600, AX-89956272, chr1_7938827, chr1_10810229, chr1_11007071 and chr1_10884171.

According to particular embodiments, the at least one SNP is selected from the group consisting of: AX-89929954, AX-89918280, AX-89938309, AX-89960828, AX-89930342, AX-89928530, AX-89949788, AX-89928131, AX-89949832, AX-89916790, AX-89973719, AX-89962023, AX-89921280, AX-89931666, AX-89921585, AX-89953905, AX-89952945, AX-89934682, AX-89951942, AX-89937020, AX-89924837, AX-89958601, AX-89923477, AX-89959350, AX-89929482, AX-89937712, AX-89949602, AX-89925103, AX-89938051, AX-89924174, AX-89936461, AX-89916703, AX-89935317 and AX-89966423.

According to other particular embodiments, the at least one SNP is selected from the group consisting of: AX-89929954, AX-89918280, AX-89938309, AX-89960828, AX-89930342, AX-89928530, AX-89949788, AX-89928131, AX-89949832, AX-89916790, AX-89973719, AX-89962023, AX-89921280, AX-89931666, AX-89921585, AX-89953905, AX-89952945 and AX-89934682.

According to more particular embodiments, the at least one SNP is AX-89929954 or AX-89918280.

According to other more particular embodiments, the at least one SNP is AX-89929954.

According to other more particular embodiments, the at least one SNP is AX-89918280.

According to further particular embodiments, the at least one SNP is selected from the group chr1_7515539, chr1_7108873, chr1_6864558, chr1_7186663, chr1_6730531, chr1_27891953, AX-89953259, chr1_6740481, chr1_6770611, chr1_7412807, chr1_7360179, chr1_7411803, chr1_7431445, chr1_7433199, chr1_7441254, chr1_7441877, chr1_7533570, chr1_6834898, chr1_6730142, chr1_6746052, chr1_6794061, chr1_7399212, chr1_7442637, chr1_7358019, chr1_7709828, chr1_7598090, chr1_7626471, chr1_7598743, chr1_7670293, chr1_7670561, chr1_7647634, chr1_7356089, chr1_8109044, and chr1 10439048

According to further more particular embodiments, the at least one SNP is chr1 7515539, chr1_7108873 and chr1_6864558.

According to certain embodiments, the population of rainbow trout, such as an isolated population of rainbow trout, is a population wherein each individual within the population comprises within its genome (e.g., on chromosome 1 of its genome) at least one nucleotide sequence selected from the group consisting of a) the nucleotide sequences set forth in SEQ ID NOs: 79 to 156, and 230 to 299 and b) nucleotide sequences derived from any one of SEQ ID NOs: 79 to 156 and 230 to 299 by 1 to 5, such as 1 to 2, nucleotide substitutions, provide that said nucleotide substitutions are not at position 36 of said derived sequence.

According to particular embodiments, the population of rainbow trout, such as an isolated population of rainbow trout, is a population wherein each individual within the population comprises within its genome (e.g., on chromosome 1 of its genome) at least one nucleotide sequence selected from the group consisting of a) the nucleotide sequences set forth in SEQ ID NOs: 79 to 112, and b) nucleotide sequences derived from any one of SEQ ID NOs: 81 to 112 by 1 to 5, such as 1 to 2, nucleotide substitutions, provide that said nucleotide substitutions are not at position 36 of said derived sequence.

According to other particular embodiments, the population of rainbow trout, such as an isolated population of rainbow trout, is a population wherein each individual within the population comprises within its genome (e.g., on chromosome 1 of its genome) at least one nucleotide sequence selected from the group consisting of a) the nucleotide sequences set forth in SEQ ID NOs: 79 to 96, and b) nucleotide sequences derived from any one of SEQ ID NOs: 79 to 96 by 1 to 5, such as 1 to 2, nucleotide substitutions, provide that said nucleotide substitutions are not at position 36 of said derived sequence.

According to more particular embodiments, the population of rainbow trout, such as an isolated population of rainbow trout, is a population wherein each individual within the population comprises within its genome (e.g., on chromosome 1 of its genome) at least one nucleotide sequence selected from the group consisting of a) the nucleotide sequences set forth in SEQ ID NO: 79 and SEQ ID NO: 80, and b) nucleotide sequences derived from any one of SEQ ID NO: 79 and SEQ ID NO: 80 by 1 to 5, such as 1 to 2, nucleotide substitutions, provided that said nucleotide substitutions are not at position 36 of said derived sequence.

According to more particular embodiments, the population of rainbow trout, such as an isolated population of rainbow trout, is a population wherein each individual within the population comprises within its genome (e.g., on chromosome 1 of its genome) at least one nucleotide sequence selected from the group consisting of a) the nucleotide sequence set forth in SEQ ID NO: 79, and b) nucleotide sequences derived from SEQ ID NO: 79 by 1 to 5, such as 1 to 2, nucleotide substitutions, provided that said nucleotide substitutions are not at position 36 of said derived sequence.

According to more particular embodiments, the population of rainbow trout, such as an isolated population of rainbow trout, is a population wherein each individual within the population comprises within its genome (e.g., on chromosome 1 of its genome) at least one nucleotide sequence selected from the group consisting of a) the nucleotide sequence set forth in SEQ ID NO: 80, and b) nucleotide sequences derived from SEQ ID NO: 80 by 1 to 5, such as 1 to 2, nucleotide substitutions, provided that said nucleotide substitutions are not at position 36 of said derived sequence.

According to further particular embodiments, the population of rainbow trout, such as an isolated population of rainbow trout, is a population wherein each individual within the population comprises within its genome (e.g., on chromosome 1 of its genome) at least one nucleotide sequence selected from the group consisting of a) the nucleotide sequences set forth in SEQ ID NOs: 230 to 263, and b) nucleotide sequences derived from any one of SEQ ID NOs: 230 to 263 to 5, such as 1 to 2, nucleotide substitutions, provide that said nucleotide substitutions are not at position 36 of said derived sequence.

According to more particular embodiments, the population of rainbow trout, such as an isolated population of rainbow trout, is a population wherein each individual within the population comprises within its genome (e.g., on chromosome 1 of its genome) at least one nucleotide sequence selected from the group consisting of a) the nucleotide sequences set forth in SEQ ID NOs: 230 to 232, and b) nucleotide sequences derived from any one of SEQ ID NOs: 230 to 232 by 1 to 5, such as 1 to 2, nucleotide substitutions, provided that said nucleotide substitutions are not at position 36 of said derived sequence.

According to more particular embodiments, the population of rainbow trout, such as an isolated population of rainbow trout, is a population wherein each individual within the population comprises within its genome (e.g., on chromosome 1 of its genome) at least one nucleotide sequence selected from the group consisting of a) the nucleotide sequence set forth in SEQ ID NO: 230 and b) nucleotide sequences derived from SEQ ID NO: 230 by 1 to 5, such as 1 to 2, nucleotide substitutions, provided that said nucleotide substitutions are not at position 36 of said derived sequence.

According to more particular embodiments, the population of rainbow trout, such as an isolated population of rainbow trout, is a population wherein each individual within the population comprises within its genome (e.g., on chromosome 1 of its genome) at least one nucleotide sequence selected from the group consisting of a) the nucleotide sequence set forth in SEQ ID NO: 231, and b) nucleotide sequences derived from SEQ ID NO: 231 by 1 to 5, such as 1 to 2, nucleotide substitutions, provided that said nucleotide substitutions are not at position 36 of said derived sequence.

According to more particular embodiments, the population of rainbow trout, such as an isolated population of rainbow trout, is a population wherein each individual within the population comprises within its genome (e.g., on chromosome 1 of its genome) at least one nucleotide sequence selected from the group consisting of a) the nucleotide sequence set forth in SEQ ID NO: 232, and b) nucleotide sequences derived from SEQ ID NO: 232 by 1 to 5, such as 1 to 2, nucleotide substitutions, provided that said nucleotide substitutions are not at position 36 of said derived sequence.

According to certain embodiments, the population of rainbow trout is a population of female rainbow trouts.

According to certain embodiments, the population of rainbow trout is a population of male rainbow trouts.

According to certain embodiments, the population of rainbow trout is a population of male and female rainbow trouts.

In one further aspect of the present invention, a population of rainbow trout may comprise in its genome at least one allele conferring IPN resistance obtainable by a process comprising the steps of:
a) genotyping the trout,
b) selecting individuals having at least one allele preferably two alleles conferring IPN resistance ("IPN resistance allele"); and
c) mating individuals in such a way that at least one individual within each mated pair has two alleles conferring IPN resistance According to certain embodiments the mating in c) may also be conducted in such a way that the mated pair each has two alleles conferring IPN resistance, or that each mated pair has one allele conferring IPN resistance.

According to certain embodiments the population of rainbow trout obtained by the process, the at least one IPN resistance allele may be an allele of at least one single nucleotide polymorphism (SNP).

According to further certain embodiments the population of rainbow trout obtained by the process, the at least one SNP is selected from the SNPs listed in Table 1.

According to further more certain embodiments the population obtained by the process, comprises within its genome at least one nucleotide sequence selected from the group consisting of a) the nucleotide sequences set forth in SEQ ID NOs: 79 to 156 and 230 to 299 and b) nucleotide sequences derived from any one of SEQ ID NOs: 79 to 156 and 230 to 299 by 1 to 5, such as 1 to 2, nucleotide substitutions, provide that said nucleotide substitutions are not at position 36 of said derived sequence According to certain embodiments, the population of rainbow trout is a population of female rainbow trouts.

According to certain embodiments, the population of rainbow trout is a population of male rainbow trouts.

According to certain embodiments, the population of rainbow trout is a population of male and female rainbow trouts.

The present invention provides in a further aspect a rainbow trout cell, such as an isolated rainbow trout cell, which comprises within its genome (e.g., on chromosome 1 of its genome) at least one allele conferring IPN resistance ("IPN resistance allele").

According to certain embodiments, the at least one IPN resistance allele is an allele of at least one polymorphism, such as at least one single nucleotide polymorphism (SNP).

According to certain embodiments, the at least one SNP is selected from the SNPs listed in Table 1.

According to certain embodiments, the at least one SNP is selected from the group consisting of: AX-89929954, AX-89918280, AX-89938309, AX-89960828, AX-89930342, AX-89928530, AX-89949788, AX-89928131, AX-89949832, AX-89916790, AX-89973719, AX-89962023, AX-89921280, AX-89931666, AX-89921585, AX-89953905, AX-89952945, AX-89934682, AX-89951942, AX-89937020, AX-89924837, AX-89958601, AX-89923477, AX-89959350, AX-89929482, AX-89937712, AX-89949602, AX-89925103, AX-89938051, AX-89924174, AX-89936461, AX-89916703, AX-89935317, AX-89966423, AX-89933348, AX-89969315, AX-89919958, AX-89968417, AX-89946851, AX-89976917, AX-89945446, AX-89919457, AX-89973597, AX-89938138, AX-89971866, AX-89958882, AX-89961273, AX-89944901, AX-89919465, AX-89959425, AX-89917102, AX-89959281, AX-89916766, AX-89920507, AX-89957370, AX-89934009, AX-89929663, AX-89952300, AX-89916572, AX-89946911, AX-89974593, AX-89927158, AX-89970383, AX-89965404, AX-89955634, AX-89932926, AX-89941493, AX-89943031, AX-89957682, AX-89960611, AX-89950199, AX-89928407, AX-89962035, AX-89931951, AX-89976536, AX-89916801, AX-89929085, AX-89925267, chr1_7515539, chr1_7108873, chr1_6864558, chr1_7186663, chr1_6730531, chr1_27891953, AX-89953259, chr1_6740481, chr1_6770611, chr1_7412807, chr1_7360179, chr1_7411803, chr1_7431445, chr1_7433199, chr1_7441254, chr1_7441877, chr1_7533570, chr1_6834898, chr1_6730142, chr1_6746052, chr1_6794061, chr1_7399212, chr1_7442637, chr1_7358019, chr1_7709828, chr1_7598090, chr1_7626471, chr1_7598743, chr1_7670293, chr1_7670561, chr1_7647634, chr1_7356089, chr1_8109044, chr1_10439048, chr1_8142346, chr1_8092208, chr1_8138683, chr1_8139206, chr1_8139744, chr1_8140789, chr1_8141687, chr1_8154917, chr1_7454708, chr1_7504847, chr1_7505686, chr1_7505817, chr1_8202031, chr1_8228173, chr1_8309469, chr1_8163977, chr1_27786931, chr1_8194629, chr1_7505259, chr1_8474659, chr1_8282602, chr1_8306806, chr1_8341618, chr1_8343786, chr1_8345836, chr1_8350569, chr1_8402403, AX-89962103, chr1_8279302, chr1_8334901, chr1_7561600, AX-89956272, chr1_7938827, chr1_10810229, chr1_11007071 and chr1_10884171.

According to particular embodiments, the at least one SNP is selected from the group consisting of: AX-89929954, AX-89918280, AX-89938309, AX-89960828, AX-89930342, AX-89928530, AX-89949788, AX-89928131, AX-89949832, AX-89916790, AX-89973719, AX-89962023, AX-89921280, AX-89931666, AX-89921585, AX-89953905, AX-89952945, AX-89934682, AX-89951942, AX-89937020, AX-89924837, AX-89958601, AX-89923477, AX-89959350, AX-89929482, AX-89937712, AX-89949602, AX-89925103, AX-89938051, AX-89924174, AX-89936461, AX-89916703, AX-89935317 and AX-89966423.

According to other particular embodiments, the at least one SNP is selected from the group consisting of: AX-89929954, AX-89918280, AX-89938309, AX-89960828, AX-89930342, AX-89928530, AX-89949788, AX-89928131, AX-89949832, AX-89916790, AX-89973719, AX-89962023, AX-89921280, AX-89931666, AX-89921585, AX-89953905, AX-89952945 and AX-89934682.

According to more particular embodiments, the at least one SNP is AX-89929954 or AX-89918280.

According to other more particular embodiments, the at least one SNP is AX-89929954.

According to other more particular embodiments, the at least one SNP is AX-89918280.

According to certain embodiments, the present invention provides a rainbow trout cell, such as an isolated rainbow trout cell, which comprises within its genome (e.g., on chromosome 1 of its genome) at least one nucleotide sequence selected from the group consisting of a) the nucleotide sequences set forth in SEQ ID NOs: 79 to 156, and b) nucleotide sequences derived from any one of SEQ ID NOs: 79 to 156 by 1 to 5, such as 1 to 2, nucleotide substitutions, provide that said nucleotide substitutions are not at position 36 of said derived sequence.

According to particular embodiments, the rainbow trout cell, such as an isolated of rainbow trout cell, comprises within its genome (e.g., on chromosome 1 of its genome) at least one nucleotide sequence selected from the group consisting of a) the nucleotide sequences set forth in SEQ ID NOs: 79 to 112, and b) nucleotide sequences derived from any one of SEQ ID NOs: 79 to 112 by 1 to 5, such as 1 to 2, nucleotide substitutions, provide that said nucleotide substitutions are not at position 36 of said derived sequence.

According to other particular embodiments, the rainbow trout cell, such as an isolated rainbow trout cell, comprises within its genome (e.g., on chromosome 1 of its genome) at least one nucleotide sequence selected from the group consisting of a) the nucleotide sequences set forth in SEQ ID NOs: 79 to 96, and b) nucleotide sequences derived from any one of SEQ ID NOs: 79 to 96 by 1 to 5, such as 1 to 2, nucleotide substitutions, provide that said nucleotide substitutions are not at position 36 of said derived sequence.

According to more particular embodiments, the rainbow trout cell, such as an isolated rainbow trout cell, comprises within its genome (e.g., on chromosome 1 of its genome) at least one nucleotide sequence selected from the group consisting of a) the nucleotide sequences set forth in SEQ ID NO: 79 and SEQ ID NO: 80, and b) nucleotide sequences derived from any one of SEQ ID NO: 79 and SEQ ID NO: 80 by 1 to 5, such as 1 to 2, nucleotide substitutions, provided that said nucleotide substitutions are not at position 36 of said derived sequence.

According to more particular embodiments, the rainbow trout cell, such as an isolated rainbow trout cell, comprises within its genome (e.g., on chromosome 1 of its genome) at least one nucleotide sequence selected from the group consisting of a) the nucleotide sequence set forth in SEQ ID NO: 79, and b) nucleotide sequences derived from SEQ ID NO: 79 by 1 to 5, such as 1 to 2, nucleotide substitutions, provided that said nucleotide substitutions are not at position 36 of said derived sequence.

According to more particular embodiments, the rainbow trout cell, such as an isolated rainbow trout cell, comprises within its genome (e.g., on chromosome 1 of its genome) at least one nucleotide sequence selected from the group consisting of a) the nucleotide sequence set forth in SEQ ID NO: 80, and b) nucleotide sequences derived from SEQ ID NO: 80 by 1 to 5, such as 1 to 2, nucleotide substitutions, provided that said nucleotide substitutions are not at position 36 of said derived sequence.

According to further particular embodiments, the population of rainbow trout, such as an isolated population of rainbow trout, is a population wherein each individual within the population comprises within its genome (e.g., on chromosome 1 of its genome) at least one nucleotide sequence selected from the group consisting of a) the nucleotide sequences set forth in SEQ ID NOs: 230 to 263, and b) nucleotide sequences derived from any one of SEQ ID NOs: 230 to 263 1 to 5, such as 1 to 2, nucleotide substitutions, provide that said nucleotide substitutions are not at position 36 of said derived sequence.

According to more particular embodiments, the population of rainbow trout, such as an isolated population of rainbow trout, is a population wherein each individual within the population comprises within its genome (e.g., on chromosome 1 of its genome) at least one nucleotide sequence selected from the group consisting of a) the nucleotide sequences set forth in SEQ ID NOs: 230 to 232, and b) nucleotide sequences derived from any one of SEQ ID NOs: 230 to 232 by 1 to 5, such as 1 to 2, nucleotide substitutions, provided that said nucleotide substitutions are not at position 36 of said derived sequence.

According to more particular embodiments, the population of rainbow trout, such as an isolated population of rainbow trout, is a population wherein each individual within the population comprises within its genome (e.g., on chromosome 1 of its genome) at least one nucleotide sequence selected from the group consisting of a) the nucleotide sequence set forth in SEQ ID NO: 230, and b) nucleotide sequences derived from SEQ ID NO: 230 by 1 to 5, such as 1 to 2, nucleotide substitutions, provided that said nucleotide substitutions are not at position 36 of said derived sequence.

According to more particular embodiments, the population of rainbow trout, such as an isolated population of rainbow trout, is a population wherein each individual within the population comprises within its genome (e.g., on chromosome 1 of its genome) at least one nucleotide sequence selected from the group consisting of a) the nucleotide sequence set forth in SEQ ID NO: 231, and b) nucleotide sequences derived from SEQ ID NO: 231 by 1 to 5, such as 1 to 2, nucleotide substitutions, provided that said nucleotide substitutions are not at position 36 of said derived sequence.

According to more particular embodiments, the population of rainbow trout, such as an isolated population of rainbow trout, is a population wherein each individual within the population comprises within its genome (e.g., on chromosome 1 of its genome) at least one nucleotide sequence selected from the group consisting of a) the nucleotide sequence set forth in SEQ ID NO: 232, and b) nucleotide sequences derived from SEQ ID NO: 232 by 1 to 5, such as 1 to 2, nucleotide substitutions, provided that said nucleotide substitutions are not at position 36 of said derived sequence.

According to certain embodiments, the rainbow trout cell is a gamete.

According to particular embodiments, the rainbow trout cell is an egg, such as an eyed egg.

According to more particular embodiments, the egg is unfertilized.

According to other more particular embodiments, the egg is fertilized.

According to particular embodiments, the rainbow trout cell is a sperm cell.

According to certain other embodiments, the rainbow trout cell is a somatic cell.

According to certain embodiments, the rainbow trout cell has been isolated from a rainbow trout of the invention.

According to particular embodiments, the rainbow trout cell has been isolated from a female rainbow trout of the invention.

According to particular embodiments, the rainbow trout cell has been isolated from a male rainbow trout of the invention.

The present invention provides in a further aspect a population of rainbow trout cells, such as an isolated population of rainbow trout cells, each individual cell within the population comprising within its genome (e.g., on chromosome 1 of its genome) at least one allele conferring IPN resistance ("IPN resistance allele").

According to certain embodiments, the at least one IPN resistance allele is an allele of at least one polymorphism, such as at least one single nucleotide polymorphism (SNP).

According to certain embodiments, the at least one SNP is selected from the SNPs listed in Table 1.

According to certain embodiments, the at least one SNP is selected from the group consisting of: AX-89929954, AX-89918280, AX-89938309, AX-89960828, AX-89930342, AX-89928530, AX-89949788, AX-89928131, AX-89949832, AX-89916790, AX-89973719, AX-89962023, AX-89921280, AX-89931666, AX-89921585, AX-89953905, AX-89952945, AX-89934682, AX-89951942, AX-89937020, AX-89924837, AX-89958601, AX-89923477, AX-89959350, AX-89929482, AX-89937712, AX-89949602, AX-89925103, AX-89938051, AX-89924174, AX-89936461, AX-89916703, AX-89935317, AX-89966423, AX-89933348, AX-89969315, AX-89919958, AX-89968417, AX-89946851, AX-89976917, AX-89945446, AX-89919457, AX-89973597, AX-89938138, AX-89971866, AX-89958882, AX-89961273, AX-89944901, AX-89919465, AX-89959425, AX-89917102, AX-89959281, AX-89916766, AX-89920507, AX-89957370, AX-89934009, AX-89929663, AX-89952300, AX-89916572, AX-89946911, AX-89974593, AX-89927158, AX-89970383, AX-89965404, AX-89955634, AX-89932926, AX-89941493, AX-89943031, AX-89957682, AX-89960611, AX-89950199, AX-89928407, AX-89962035, AX-89931951, AX-89976536, AX-89916801, AX-89929085, AX-89925267, chr1_7515539, chr1_7108873, chr1_6864558, chr1_7186663, chr1_6730531, chr1_27891953, AX-89953259, chr1_6740481, chr1_6770611, chr1_7412807, chr1_7360179, chr1_7411803, chr1_7431445, chr1_7433199, chr1_7441254, chr1_7441877, chr1_7533570, chr1_6834898, chr1_6730142, chr1_6746052, chr1_6794061, chr1_7399212, chr1_7442637, chr1_7358019, chr1_7709828, chr1_7598090, chr1_7626471, chr1_7598743, chr1_7670293, chr1_7670561, chr1_7647634, chr1_7356089, chr1_8109044, chr1_10439048, chr1_8142346, chr1_8092208, chr1_8138683, chr1_8139206, chr1_8139744, chr1_8140789, chr1_8141687, chr1_8154917, chr1_7454708, chr1_7504847, chr1_7505686, chr1_7505817, chr1_8202031, chr1_8228173, chr1_8309469, chr1_8163977, chr1_27786931, chr1_8194629, chr1_7505259, chr1_8474659, chr1_8282602, chr1_8306806, chr1_8341618, chr1_8343786, chr1_8345836, chr1_8350569, chr1_8402403, AX-89962103, chr1_8279302, chr1_8334901, chr1_7561600, AX-89956272, chr1_7938827, chr1_10810229, chr1_11007071 and chr1_10884171.

According to particular embodiments, the at least one SNP is selected from the group consisting of: AX-89929954, AX-89918280, AX-89938309, AX-89960828, AX-89930342, AX-89928530, AX-89949788, AX-89928131, AX-89949832, AX-89916790, AX-89973719, AX-89962023, AX-89921280, AX-89931666, AX-89921585, AX-89953905, AX-89952945, AX-89934682, AX-89951942, AX-89937020, AX-89924837, AX-89958601, AX-89923477, AX-89959350, AX-89929482, AX-89937712, AX-89949602, AX-89925103, AX-89938051, AX-89924174, AX-89936461, AX-89916703, AX-89935317 and AX-89966423.

According to other particular embodiments, the at least one SNP is selected from the group consisting of: AX-89929954, AX-89918280, AX-89938309, AX-89960828, AX-89930342, AX-89928530, AX-89949788, AX-89928131, AX-89949832, AX-89916790, AX-89973719, AX-89962023, AX-89921280, AX-89931666, AX-89921585, AX-89953905, AX-89952945 and AX-89934682.

According to more particular embodiments, the at least one SNP is AX-89929954 or AX-89918280.

According to other more particular embodiments, the at least one SNP is AX-89929954.

According to other more particular embodiments, the at least one SNP is AX-89918280.

According to further particular embodiments, the at least one SNP is selected from the group: chr1_7515539, chr1_7108873, chr1_6864558, chr1_7186663, chr1_6730531, chr1_27891953, AX-89953259, chr1_6740481, chr1_6770611, chr1_7412807, chr1_7360179, chr1_7411803, chr1_7431445, chr1_7433199, chr1_7441254, chr1_7441877, chr1_7533570, chr1_6834898, chr1_6730142, chr1_6746052, chr1_6794061, chr1_7399212, chr1_7442637, chr1_7358019, chr1_7709828, chr1_7598090, chr1_7626471, chr1_7598743, chr1_7670293, chr1_7670561, chr1_7647634, chr1_7356089, chr1_8109044, and chr1_10439048

According to further more particular embodiments, the at least one SNP is chr1_7515539, chr1_7108873 and chr1_6864558.

According to other more particular embodiments, the at least one SNP is chr1_7515539, According to other more particular embodiments, the at least one SNP is chr1_7108873.

According to other more particular embodiments, the at least one SNP is chr1_6864558.

According to certain embodiments, the present invention provides a population of rainbow trout cells, such as an isolated population of rainbow trout cells, each individual cell within the population comprising within its genome (e.g., on chromosome 1 of its genome) at least one nucleotide sequence selected from the group consisting of a) the nucleotide sequences set forth in SEQ ID NOs: 79 to 156, and 230 to 299 and b) nucleotide sequences derived from any one of SEQ ID NOs: 79 to 156 and 230 to 299 by 1 to 5, such as 1 to 2, nucleotide substitutions, provide that said nucleotide substitutions are not at position 36 of said derived sequence.

According to particular embodiments, the population of rainbow trout cells, such as an isolated population of rainbow trout cells, is a population wherein each individual cell within the population comprises within its genome (e.g., on chromosome 1 of its genome) at least one nucleotide sequence selected from the group consisting of a) the nucleotide sequences set forth in SEQ ID NOs: 79 to 112, and b) nucleotide sequences derived from any one of SEQ ID NOs: 79 to 112 by 1 to 5, such as 1 to 2, nucleotide substitutions, provide that said nucleotide substitutions are not at position 36 of said derived sequence.

According to other particular embodiments, the population of rainbow trout cells, such as an isolated population of rainbow trout cells, is a population wherein each individual cell within the population comprises within its genome (e.g., on chromosome 1 of its genome) at least one nucleotide sequence selected from the group consisting of a) the nucleotide sequences set forth in SEQ ID NOs: 79 to 96, and b) nucleotide sequences derived from any one of SEQ ID NOs: 79 to 96 by 1 to 5, such as 1 to 2, nucleotide substitutions, provide that said nucleotide substitutions are not at position 36 of said derived sequence.

According to more particular embodiments, the population of rainbow trout cells, such as an isolated population of rainbow trout cells, is a population wherein each individual cell within the population comprises within its genome (e.g., on chromosome 1 of its genome) at least one nucleotide sequence selected from the group consisting of a) the nucleotide sequences set forth in SEQ ID NO: 79 and SEQ ID NO: 80, and b) nucleotide sequences derived from any one of SEQ ID NO: 79 and SEQ ID NO: 80 by 1 to 5, such as 1 to 2, nucleotide substitutions, provided that said nucleotide substitutions are not at position 36 of said derived sequence.

According to more particular embodiments, the population of rainbow trout cells, such as an isolated population of rainbow trout cells, is a population wherein each individual cell within the population comprises within its genome (e.g., on chromosome 1 of its genome) at least one nucleotide sequence selected from the group consisting of a) the nucleotide sequence set forth in SEQ ID NO: 79, and b) nucleotide sequences derived from SEQ ID NO: 79 by 1 to 5, such as 1 to 2, nucleotide substitutions, provided that said nucleotide substitutions are not at position 36 of said derived sequence.

According to more particular embodiments, the population of rainbow trout cells, such as an isolated population of rainbow trout cells, is a population wherein each individual cell within the population comprises within its genome (e.g., on chromosome 1 of its genome) at least one nucleotide sequence selected from the group consisting of a) the nucleotide sequence set forth in SEQ ID NO: 80, and b) nucleotide sequences derived from SEQ ID NO: 80 by 1 to 5, such as 1 to 2, nucleotide substitutions, provided that said nucleotide substitutions are not at position 36 of said derived sequence.

According to further particular embodiments, the population of rainbow trout, such as an isolated population of rainbow trout, is a population wherein each individual within the population comprises within its genome (e.g., on chromosome 1 of its genome) at least one nucleotide sequence selected from the group consisting of a) the nucleotide sequences set forth in SEQ ID NOs: 230 to 263, and b) nucleotide sequences derived from any one of SEQ ID NOs: 230 to 263 by 1 to 5, such as 1 to 2, nucleotide substitutions, provide that said nucleotide substitutions are not at position 36 of said derived sequence.

According to more particular embodiments, the population of rainbow trout, such as an isolated population of rainbow trout, is a population wherein each individual within the population comprises within its genome (e.g., on chromosome 1 of its genome) at least one nucleotide sequence selected from the group consisting of a) the nucleotide sequences set forth in SEQ ID NOs: 230 to 232, and b) nucleotide sequences derived from any one of SEQ ID NOs: 230 to 232 by 1 to 5, such as 1 to 2, nucleotide substitutions, provided that said nucleotide substitutions are not at position 36 of said derived sequence.

According to more particular embodiments, the population of rainbow trout, such as an isolated population of rainbow trout, is a population wherein each individual within the population comprises within its genome (e.g., on chromosome 1 of its genome) at least one nucleotide sequence selected from the group consisting of a) the nucleotide sequence set forth in SEQ ID NO: 230, and b) nucleotide sequences derived from SEQ ID NO: 230 by 1 to 5, such as 1 to 2, nucleotide substitutions, provided that said nucleotide substitutions are not at position 36 of said derived sequence.

According to more particular embodiments, the population of rainbow trout, such as an isolated population of rainbow trout, is a population wherein each individual within the population comprises within its genome (e.g., on chromosome 1 of its genome) at least one nucleotide sequence selected from the group consisting of a) the nucleotide sequence set forth in SEQ ID NO: 231, and b) nucleotide sequences derived from SEQ ID NO: 231 by 1 to 5, such as 1 to 2, nucleotide substitutions, provided that said nucleotide substitutions are not at position 36 of said derived sequence.

According to more particular embodiments, the population of rainbow trout, such as an isolated population of rainbow trout, is a population wherein each individual within the population comprises within its genome (e.g., on chromosome 1 of its genome) at least one nucleotide sequence selected from the group consisting of a) the nucleotide sequence set forth in SEQ ID NO: 232 and b) nucleotide sequences derived from SEQ ID NO: 232 by 1 to 5, such as 1 to 2, nucleotide substitutions, provided that said nucleotide substitutions are not at position 36 of said derived sequence.

According to certain embodiments, the cells of said population are gametes.

According to particular embodiments, the cells of said population are eggs, such as eyed eggs.

According to more particular embodiments, the eggs are unfertilized.

According to other more particular embodiments, the eggs are fertilized.

According to other more particular embodiments, the population of rainbow trout cells is a mixed population of fertilized and unfertilized eggs.

According to other particular embodiments the cells of said population are sperm cells.

According to certain other embodiments, the cells of said population are somatic cells.

According to certain embodiments, the population of rainbow trout cells has been isolated from a rainbow trout of the invention.

According to particular embodiments, the population of rainbow trout cells has been isolated from a female rainbow trout of the invention.

According to particular embodiments, the population of rainbow trout cells has been isolated from a male rainbow trout of the invention.

The present invention provides in a particular aspect a rainbow trout egg, such as an isolated rainbow trout egg, which comprises within its genome (e.g., on chromosome 1 of its genome) at least one allele conferring IPN resistance ("IPN resistance allele").

According to certain embodiments, the at least one IPN resistance allele is an allele of at least one polymorphism, such as at least one single nucleotide polymorphism (SNP).

According to certain embodiments, the at least one SNP is selected from the SNPs listed in Table 1.

According to particular embodiments, the at least one SNP is AX-89929954 or AX-89918280.

According to certain embodiments, the present invention provides a rainbow trout egg, such as an isolated rainbow trout egg, which comprises within its genome (e.g., on chromosome 1 of its genome) at least one nucleotide sequence selected from the group consisting of a) the nucleotide sequences set forth in SEQ ID NOs: 79 to 156 and 230 to 299, and b) nucleotide sequences derived from any one of SEQ ID NOs: 79 to 156 and 230 to 299 by 1 to 5, such as 1 to 2, nucleotide substitutions, provide that said nucleotide substitutions are not at position 36 of said derived sequence.

According to particular embodiments, the present invention provides a rainbow trout egg, such as an isolated rainbow trout egg, which comprises within its genome (e.g., on chromosome 1 of its genome) at least one nucleotide sequence selected from the group consisting of a) the nucleotide sequences set forth in SEQ ID NO: 79 and SEQ ID NO: 80, and b) nucleotide sequences derived from any one of SEQ ID NO: 79 and SEQ ID NO: 80 by 1 to 5, such as 1 to 2, nucleotide substitutions, provided that said nucleotide substitutions are not at position 36 of said derived sequence.

According to further other more particular embodiments, the at least one SNP is chr1_7515539, chr1_7108873 or chr1_6864558.

According to particular embodiments, the present invention provides a rainbow trout egg, such as an isolated rainbow trout egg, which comprises within its genome (e.g., on chromosome 1 of its genome) at least one nucleotide sequence selected from the group consisting of a) the nucleotide sequences set forth in SEQ ID NOs: 230 to 232 and b) nucleotide sequences derived from any one of SEQ ID NOs: 230 to 232 by 1 to 5, such as 1 to 2, nucleotide substitutions, provided that said nucleotide substitutions are not at position 36 of said derived sequence.

According to certain embodiments, the rainbow trout egg is unfertilized.

According to certain other embodiments, the rainbow trout egg is fertilized.

According to particular embodiments, the rainbow trout egg is an eyed egg.

According to certain embodiments, the rainbow trout egg has been isolated from a female rainbow trout of the invention.

The present invention provides in a further aspect a population of rainbow trout eggs, such as an isolated population of rainbow trout eggs, each individual egg of the population comprising within its genome (e.g., on chromosome 1 of its genome) at least one allele conferring IPN resistance ("IPN resistance allele").

According to certain embodiments, the at least one IPN resistance allele is an allele of at least one polymorphism, such as at least one single nucleotide polymorphism (SNP).

According to certain embodiments, the at least one SNP is selected from the SNPs listed in Table 1.

According to particular embodiments, the at least one SNP is AX-89929954 or AX-89918280.

According to further embodiments, the at least one SNP is chr1_7515539, chr1_7108873 or chr1_6864558.

According to certain embodiments, the present invention provides a population of rainbow trout eggs, such as an isolated population of rainbow trout eggs, which comprises within its genome (e.g., on chromosome 1 of its genome) at least one nucleotide sequence selected from the group consisting of a) the nucleotide sequences set forth in SEQ ID NOs: 79 to 156, and 230 to 299 and b) nucleotide sequences derived from any one of SEQ ID NOs: 79 to 156 and 230 to 299 by 1 to 5, such as 1 to 2, nucleotide substitutions, provide that said nucleotide substitutions are not at position 36 of said derived sequence.

According to particular embodiments, the present invention provides a population of rainbow trout eggs, such as an isolated population of rainbow trout eggs, each individual egg within the population comprising within its genome (e.g., on chromosome 1 of its genome) at least one nucleotide sequence selected from the group consisting of a) the nucleotide sequences set forth in SEQ ID NO: 79 and SEQ ID NO: 80, and b) nucleotide sequences derived from any one of SEQ ID NO: 79 and SEQ ID NO: 80 by 1 to 5, such as 1 to 2, nucleotide substitutions, provided that said nucleotide substitutions are not at position 36 of said derived sequence.

According to particular embodiments, the present invention provides a population of rainbow trout eggs, such as an isolated population of rainbow trout eggs, each individual egg within the population comprising within its genome (e.g., on chromosome 1 of its genome) at least one nucleotide sequence selected from the group consisting of a) the nucleotide sequences set forth in SEQ ID NOs: 230 to 232, and b) nucleotide sequences derived from any one of SEQ ID NO: 230 to 232 by 1 to 5, such as 1 to 2, nucleotide substitutions, provided that said nucleotide substitutions are not at position 36 of said derived sequence.

According to certain embodiments, the population of rainbow trout eggs is unfertilized.

According to certain other embodiments, the population of rainbow trout eggs is fertilized.

According to certain other embodiments, the population of rainbow trout eggs is a population of eyed eggs.

According to certain embodiments, the population of rainbow trout eggs has been isolated from a female rainbow trout of the invention.

Nucleic Acid Molecules of the Invention

The present invention provides in a further aspect a nucleic acid molecule, such as an isolated nucleic acid molecule. More particularly, the present invention provides a nucleic acid, such as an isolated nucleic acid comprising at least one nucleotide sequence selected from the group consisting of a) the nucleotide sequences set forth in SEQ ID NO: 79 to 156 and 230 to 299, b) nucleotide sequences derived from any one of SEQ ID NOs: 79 to 156 and 230 to 299 by 1 to 5, such as 1 to 2, nucleotide substitutions, provided that said nucleotide substitutions are not at position 36 of said derived sequence, and c) complements of a) and b).

According to certain embodiments, the nucleic acid molecule, such as an isolated nucleic acid molecule, comprises at least one nucleotide sequence selected from the group consisting of a) the nucleotide sequences set forth in SEQ ID NO: 79 to 112, b) nucleotide sequences derived from any one of SEQ ID NOs: 79 to 112 by 1 to 5, such as 1 to 2, nucleotide substitutions, provided that said nucleotide substitutions are not at position 36 of said derived sequence, and c) complements of a) and b).

According to certain other embodiments, the nucleic acid molecule, such as an isolated nucleic acid molecule, comprises at least one nucleotide sequence selected from the group consisting of a) the nucleotide sequences set forth in SEQ ID NO: 79 to 96, b) nucleotide sequences derived from any one of SEQ ID NOs: 79 to 96 by 1 to 5, such as 1 to 2, nucleotide substitutions, provided that said nucleotide substitutions are not at position 36 of said derived sequence, and c) complements of a) and b).

According to particular embodiments, the nucleic acid molecule, such as an isolated nucleic acid molecule, comprises at least one nucleotide sequence selected from the group consisting of a) the nucleotide sequences set forth in SEQ ID NO: 79 and SEQ ID NO: 80, b) nucleotide sequences derived from any one of SEQ ID NO: 79 and SEQ ID NO: 80 by 1 to 5, such as 1 to 2, nucleotide substitutions, provided that said nucleotide substitutions are not at position 36 of said derived sequence, and c) complements of a) and b).

According to more particular embodiments, the nucleic acid molecule, such as an isolated nucleic acid molecule, comprises the nucleotide sequence set forth in SEQ ID NO: 79, or a nucleotide sequence derived from SEQ ID NO: 79 by 1 to 5, such as 1 to 2, nucleotide substitutions, provided that said nucleotide substitutions are not at position 36 of said derived sequence, or a complement thereof.

According to more particular embodiments, the nucleic acid molecule, such as an isolated nucleic acid molecule, comprises the nucleotide sequence set forth in SEQ ID NO: 80, or a nucleotide sequence derived from SEQ ID NO: 80 by 1 to 5, such as 1 to 2, nucleotide substitutions, provided that said nucleotide substitutions are not at position 36 of said derived sequence, or a complement thereof.

According to certain embodiments, the nucleic acid molecule, such as an isolated nucleic acid molecule, comprises at least one nucleotide sequence selected from the group consisting of a) the nucleotide sequences set forth in SEQ ID NO: 230 to 263, b) nucleotide sequences derived from any one of SEQ ID NOs: 230 to 263 by 1 to 5, such as 1 to 2, nucleotide substitutions, provided that said nucleotide substitutions are not at position 36 of said derived sequence, and c) complements of a) and b).

According to particular embodiments, the nucleic acid molecule, such as an isolated nucleic acid molecule, comprises at least one nucleotide sequence selected from the group consisting of a) the nucleotide sequences set forth in SEQ ID NOs: 230 to 232, and b) nucleotide sequences derived from any one of SEQ ID NOs: 230 to 232 by 1 to 5, such as 1 to 2, nucleotide substitutions, provided that said nucleotide substitutions are not at position 36 of said derived sequence, and c) complements of a) and b).

According to more particular embodiments, the nucleic acid molecule, such as an isolated nucleic acid molecule, comprises the nucleotide sequence set forth in SEQ ID NO: 230, or a nucleotide sequence derived from SEQ ID NO: 230 by 1 to 5, such as 1 to 2, nucleotide substitutions, provided that said nucleotide substitutions are not at position 36 of said derived sequence, or a complement thereof.

According to more particular embodiments, the nucleic acid molecule, such as an isolated nucleic acid molecule, comprises the nucleotide sequence set forth in SEQ ID NOs: 231 or a nucleotide sequence derived from SEQ ID NO: 231 by 1 to 5, such as 1 to 2, nucleotide substitutions, provided that said nucleotide substitutions are not at position 36 of said derived sequence, or a complement thereof.

According to more particular embodiments, the nucleic acid molecule, such as an isolated nucleic acid molecule, comprises the nucleotide sequence set forth in SEQ ID NOs: 232 or a nucleotide sequence derived from SEQ ID NO: 232 by 1 to 5, such as 1 to 2, nucleotide substitutions, provided that said nucleotide substitutions are not at position 36 of said derived sequence, or a complement thereof.

The nucleic acid molecule may have a length of at least 71 nucleotides, such as at least 75 nucleotides or at least 100 nucleotides.

According to certain embodiments, the nucleic acid has a length from 71 nucleotides to 400 nucleotides, such as from 71 nucleotides to 200 nucleotides or from 71 to 100 nucleotides.

The present invention provides in a further aspect an oligonucleotide, such as an isolated oligonucleotide. More particular, the present invention provides an oligonucleotide, such as an isolated oligonucleotide, comprising at least 10 contiguous nucleotides, such as at least 16 contiguous nucleotides, of a nucleotide sequence selected from the group consisting of a) the nucleotide sequences set forth in SEQ ID NOs: 79 to 156 and 230 to 299 and b) nucleotide sequences derived from any one of SEQ ID NOs: 79 and 156 and 230 to 299 by 1 to 5, such as 1 to 2, nucleotide substitutions, provided that said nucleotide substitutions are not at position 36 of said derived sequence; wherein said at least 10 contiguous nucleotides include the nucleotide at position 36 of a) or b); or a complement of said oligonucleotide.

According to certain embodiments, the oligonucleotide comprises at least 10 contiguous nucleotides, such as at least 16 contiguous nucleotides, of a nucleotide sequence selected from the group consisting of a) the nucleotide sequences set forth in SEQ ID NOs: 79 to 112, and b) nucleotide sequences derived from any one of SEQ ID NO: 79 and 112 by 1 to 5, such as 1 to 2, nucleotide substitutions, provided that said nucleotide substitutions are not at position 36 of said derived sequence; wherein said at least 10 contiguous nucleotides include the nucleotide at position 36 of a) or b); or a complement of said oligonucleotide.

According to certain embodiments, the oligonucleotide comprises at least 10 contiguous nucleotides, such as at least 16 contiguous nucleotides, of a nucleotide sequence selected from the group consisting of a) the nucleotide sequences set forth in SEQ ID NOs: 79 to 96, and b) nucleotide sequences derived from any one of SEQ ID NO: 79 to 96 by 1 to 5, such as 1 to 2, nucleotide substitutions, provided that said nucleotide substitutions are not at position 36 of said derived sequence; wherein said at least 10 contiguous nucleotides include the nucleotide at position 36 of a) or b); or a complement of said oligonucleotide.

According to particular embodiments, the oligonucleotide comprises at least 10 contiguous nucleotides, such as at least 16 contiguous nucleotides, of a nucleotide sequence selected from the group consisting of a) the nucleotide sequences set forth in SEQ ID NOs: 79 and 80, and b) nucleotide sequences derived from any one of SEQ ID NO: 79 and 80 by 1 to 5, such as 1 to 2, nucleotide substitutions, provided that said nucleotide substitutions are not at position 36 of said derived sequence; wherein said at least 10 contiguous nucleotides include the nucleotide at position 36 of a) or b); or a complement of said oligonucleotide.

According to more particular embodiments, the oligonucleotide comprises at least 10 contiguous nucleotides, such as at least 16 contiguous nucleotides, of a nucleotide sequence selected from the group consisting of a) the nucleotide sequence set forth in SEQ ID NOs: 79, and b) nucleotide sequences derived from SEQ ID NO: 79 by 1 to 5, such as 1 to 2, nucleotide substitutions, provided that said nucleotide substitutions are not at position 36 of said derived sequence; wherein said at least 10 contiguous nucleotides include the nucleotide at position 36 of a) or b); or a complement of said oligonucleotide.

According to other more particular embodiments, the oligonucleotide comprises at least 10 contiguous nucleotides, such as at least 16 contiguous nucleotides, of a nucleotide sequence selected from the group consisting of a) the nucleotide sequence set forth in SEQ ID NOs: 80, and b) nucleotide sequences derived from SEQ ID NO: 80 by 1 to 5, such as 1 to 2, nucleotide substitutions, provided that said nucleotide substitutions are not at position 36 of said derived sequence; wherein said at least 10 contiguous nucleotides include the nucleotide at position 36 of a) or b); or a complement of said oligonucleotide.

According to certain embodiments, the oligonucleotide comprises at least 10 contiguous nucleotides, such as at least 16 contiguous nucleotides, of a nucleotide sequence selected from the group consisting of a) the nucleotide sequences set forth in SEQ ID NOs: 230 to 263, and b) nucleotide sequences derived from any one of SEQ ID NO: 230 and 263 by 1 to 5, such as 1 to 2, nucleotide substitutions, provided that said nucleotide substitutions are not at position 36 of said derived sequence; wherein said at least 10 contiguous nucleotides include the nucleotide at position 36 of a) or b); or a complement of said oligonucleotide.

According to particular embodiments, the oligonucleotide comprises at least 10 contiguous nucleotides, such as at least 16 contiguous nucleotides, of a nucleotide sequence selected from the group consisting of a) the nucleotide sequences set forth in SEQ ID NOs: 230 to 232 and b) nucleotide sequences derived from any one of SEQ ID NO: 230 to 232 by 1 to 5, such as 1 to 2, nucleotide substitutions, provided that said nucleotide substitutions are not at position 36 of said derived sequence; wherein said at least 10 contiguous nucleotides include the nucleotide at position 36 of a) or b); or a complement of said oligonucleotide.

According to more particular embodiments, the oligonucleotide comprises at least 10 contiguous nucleotides, such as at least 16 contiguous nucleotides, of a nucleotide sequence selected from the group consisting of a) the nucleotide sequence set forth in SEQ ID NOs: 230, and b) nucleotide sequences derived from SEQ ID NO: 230 by 1 to 5, such as 1 to 2, nucleotide substitutions, provided that said nucleotide substitutions are not at position 36 of said derived sequence; wherein said at least 10 contiguous nucleotides include the nucleotide at position 36 of a) or b); or a complement of said oligonucleotide.

According to other more particular embodiments, the oligonucleotide comprises at least 10 contiguous nucleotides, such as at least 16 contiguous nucleotides, of a nucleotide sequence selected from the group consisting of a) the nucleotide sequence set forth in SEQ ID NOs: 80, and b) nucleotide sequences derived from SEQ ID NO: 231 by 1 to 5, such as 1 to 2, nucleotide substitutions, provided that said nucleotide substitutions are not at position 36 of said derived sequence; wherein said at least 10 contiguous nucleotides include the nucleotide at position 36 of a) or b); or a complement of said oligonucleotide.

According to other more particular embodiments, the oligonucleotide comprises at least 10 contiguous nucleotides, such as at least 16 contiguous nucleotides, of a nucleotide sequence selected from the group consisting of a) the nucleotide sequence set forth in SEQ ID NOs: 80, and b) nucleotide sequences derived from SEQ ID NO: 232 by 1 to 5, such as 1 to 2, nucleotide substitutions, provided that said nucleotide substitutions are not at position 36 of said derived sequence; wherein said at least 10 contiguous nucleotides include the nucleotide at position 36 of a) or b); or a complement of said oligonucleotide.

According to certain embodiments, the oligonucleotide or complement thereof has a length of at least 10 nucleotides, such as at least 16 nucleotides.

According to certain embodiments, the oligonucleotide or complement thereof has a length of at least 16 nucleotides, such as at least 20 nucleotides.

According to certain embodiments, the oligonucleotide or complement thereof has a length of at least 20 nucleotides, such as at least 25 nucleotides.

According to certain embodiments, the oligonucleotide or complement thereof has a length of 10 to 200 nucleotides, such as 10 to 150 nucleotides.

According to certain embodiments, the oligonucleotide or complement thereof has a length of 10 to 100 nucleotides, such as 10 to 70 nucleotides.

According to certain embodiments, the oligonucleotide or complement thereof has a length of 16 to 100 nucleotides, such as 16 to 70 nucleotides.

According to certain embodiments, the oligonucleotide or complement thereof has a length of 10 to 50 nucleotides, such as 10 to 40 nucleotides.

According to certain embodiments, the oligonucleotide or complement thereof has a length of 16 to 50 nucleotides, such as 16 to 40 nucleotides.

According to certain embodiments, the oligonucleotide or complement thereof has a length of 10 to 30 nucleotides, such as 8 to 25 nucleotides.

According to certain embodiments, the oligonucleotide or complement thereof has a length of 16 to 30 nucleotides, such as 16 to 25 nucleotides.

According to certain embodiments, the oligonucleotide or complement thereof is a primer, such as a PCR primer.

According to certain embodiments, the oligonucleotide or complement thereof is a probe, such as a hybridization probe.

According to certain embodiments, the present invention provides a complement to the oligonucleotide specified above. Such complement may be used as a probe, such as a hybridization probe.

A probe or primer according to the present invention may have attached to it a detectable label or reporter molecule. Typical labels include radioactive isotopes, enzyme substrates, co-factors, ligands, chemiluminescent or fluorescent agents, haptens, and enzymes. Methods for labelling and guidance in the choice of labels appropriate for various purposes are discussed, for example, in Sambrook et al. (In Molecular Cloning, A Laboratory Manual, CSHL, New York, 1989) and Ausubel et al. (In Current Protocols in Molecular Biology, John Wiley & Sons, New York, 1998). As a particular example, a probe or primer may include one fluorophor, such as an acceptor fluorophore or donor fluorophor. Such fluorophore may be attached at the 5'- or 3' end of the probe/primer.

Probes are generally at least 15 nucleotides in length, such as at least 16, at least 17, at least 18, at least 19, at least 20, at least 25, at least 30, at least 35, at least 40, at least 45, at least 50, at least 55, at least 60, at least 65, at least 70, or more contiguous nucleotides complementary to the target nucleic acid molecule, such as 20 to 70 nucleotides, 20 to 60 nucleotides, 20 to 50 nucleotides, 20 to 40 nucleotides, or 20 to 30 nucleotides.

Primers are shorter in length. An oligonucleotide used as primer may be at least 10 nucleotides in length. The specificity of a primer increases with its length. Thus, for example, a primer that includes 30 consecutive nucleotides will anneal to a target sequence with a higher specificity that a corresponding primer of only 15 nucleotides. Thus, to obtain greater specificity, primers of the invention are at least 15 nucleotides in length, such as at least 16, at least 17, at least 18, at least 19, at least 20, at least 25, at least 30, at least 35, at least 40, at least 45, at least 50, at least 55, at least 60, at least 65, at least 70, or more contiguous nucleotides complementary to the target nucleic acid molecule, such as 15 to 70 nucleotides, 15 to 60 nucleotides, 15 to 50 nucleotides, 15 to 40 nucleotides, or 15 to 30 nucleotides. Primer pairs can be used for amplification of nucleic acid sequences, for example, by PCT, real-time-PCR, or other nucleic-acid amplification methods known in the art.

Validation of the Results Underlying the Present Invention

Two challenge tests were carried out, in order to validate the association between IPN resistance and alleles at four of the polymorphisms of the invention. The tests were carried out in two 100 liter tanks, and in each tank a group of rainbow trout individuals was tested for resistance against one of two strains of the IPN virus. The two strains were 1) a strain (AGT11-2) of serotype Sp isolated from Norwegian sea-water-reared rainbow trout; the same strain that was used when the Inventions were first made, and 2) a strain of serotype Wb isolated from an outbreak in rainbow trout in Chile. The validation experiment confirmed that a statistically significant association exists between IPN resistance and alleles at all four investigated polymorphisms. Furthermore, the association was valid also when the IPN virus strain used in the initial discovery of the Invention (a strain of serotype Sp) was replaced with a different strain (of serotype Wb, West Buxon). It follows that the association between DNA polymorphisms and IPN resistance is reproducible and independent of virus strain.

The four polymorphisms tested in the validation experiment were representatives of all polymorphisms of the Invention. The remaining polymorphisms of the Invention were not tested directly. However, since all polymorphisms of the Inventions are markers of one and the same quantitative trait locus (QTL), it is reasonable to conclude that any other polymorphisms of the Invention would have passed the validation test.

It is a natural and necessary consequence of these findings that the DNA polymorphisms of the present invention may be used in order to create rainbow trout with increased resistance to IPN. The results from this validation study is presented in Examples 2 and 3.

Certain Definitions

As used herein, "increased resistance" to infectious pancreatic necrosis means that an individual having increased resistance has a higher probability of surviving an IPN outbreak than a random individual (from the same outbreak) with whom it is comparable. Two individuals are comparable if they are, with regards to all discriminating factors except the genotype at the SNP which is used for predicting IPN-resistance, random representatives of one and the same population of rainbow trout. An IPN outbreak is a condition in which live rainbow trout are exposed to the IPN virus in such a way that some individuals get infected and spread the virus (leading to a spread of the disease). An outbreak can be, for example, an unintended outbreak of the virus in a tank or pond of freshwater reared rainbow trout, an unintended outbreak in a net-pen of seawater reared trouts, or a controlled outbreak induced as part of a laboratory experiment. The IPN challenge-test described here (challenge tests 1, 2, 3 and 4) are examples of laboratory experiments that measure survival rates during IPN outbreaks.

As used herein, an "IPN resistance allele" is an allele conferring increased resistance to infectious pancreatic necrosis. This means that a rainbow trout having such allele at the position of a polymorphism detailed herein shows increased resistance to IPN. The "IPN resistance allele" may identify a single nucleotide polymorphism that can be used to detect or determine the degree of resistance to IPN.

As used herein, a "polymorphism" is a variation in a genomic sequence. In particular, a polymorphism is a position on the genome where different allelic variants are generally found between individuals of a population, or between individuals from different populations. The polymorphism may be a single nucleotide difference present at a locus, or may be an insertion or deletion of one or a few nucleotides at a position of a gene.

As used herein, a "single nucleotide polymorphism" or "SNP" refers to a single base (nucleotide) polymorphism in a DNA sequence among individuals in a population. As such, a single nucleotide polymorphism is characterized by the presence in a population of one or two, three or four different nucleotides (i.e. adenine, cytosine, guanine or thymine), typically less than all four nucleotides, at a particular locus in a genome, such as the genome of rainbow trout.

As used herein, "polymorphic sequence" refers to a nucleotide sequence including a polymorphic site at which a SNP or another type of polymorphism occurs.

As used herein, a "polymorphic site" is the locus or position within a given sequence at which divergence occurs. Preferred polymorphic sites have at least two alleles, each occurring at frequency greater than 1%, and more preferably greater than 10%. Those skilled in the art will recognize that nucleic acid molecules may be double-stranded molecules and that reference to a particular site on one strand refers, as well, to the corresponding site on a complementary strand. In defining a polymorphic site or allele reference to an adenine, a thymine, a cytosine, or a guanine at a particular site on one strand of a nucleic acid molecule also defines the thymine, adenine, guanine, or cytosine (respectively) at the corresponding site on a complementary strand of the nucleic acid.

Herein, when a polymorphism is specified as having a particular allele, then it is understood that that particular allele goes together with the sequence given for the polymorphism. For example, when it is said that guanine is the resistance-allele of SNP AX-89929954 (SNP #1), then it is understood that the resistance allele of AX-89929954 harbours a guanine nucleotide in the polymorphic site, defined in Table 2, when the DNA is read in the direction defined in Table 2. In other words, as stated in Table 2, the resistance form of the DNA sequence of AX-89929954 (with flanking sequence) is GAAAGAAACAGTGATAGGCTTTTAGT-GAGCACATACATTTGACACACAGTTGTGTGAAAA CAAAGCATGTG (polymorphic site underlined) when read in the direction defined in Table 2. When read in the opposite direction, the sequence of AX-89929954 (with flanking sequence) is CACATGCTTTGTTTT-CACACAACTGTGTGTCAAATGTATGTGCT-CACTAAAAGCCTATCAC TGTTTCTTTC (polymorphic site underline). Although only one direction is used when IPN resistance alleles and non-IPN resistance alleles are defined herein, the two read directions are equivalent.

As used herein, a "sample", such as a biological sample that includes nucleic acid molecules, is a sample obtained from a rainbow trout, including, but not limited to, cells, tissue, and bodily fluids.

As used herein, an "oligonucleotide" is a plurality of joined nucleotides joined by native phosphodiester bonds, typically from 8 to 300 nucleotides in length.

As used herein, "probes" and "primer" are isolated oligonucleotides of at least 8 nucleotides, such as at least 10 nucleotides, capable of hybridizing to a target nucleic acid.

As used herein, "isolated" means that an organism or a biological component, such as a cell, population of cells or a nucleic acid molecule, has been separated from its natural environment.

As used herein, "genetic linkage" refers to the tendency of polymorphisms that are located close to each other on a chromosome to be inherited together during meiosis. Thus, polymorphisms located close to each other on the same chromosome are said to be genetically linked. Alleles at two such genetically linked loci are co-inherited (from parents to offspring) more often than they are not. Assume, for example, two polymorphisms; polymorphism A having alleles A1 and A2, and polymorphism B having alleles B1 and B2. Assume further that a given rainbow trout carries all of the alleles A1, A2, B1, and B2 (in other words, this rainbow trout is heterozygous at both marker and marker B). If alleles A1 and B1 are, in this particular rainbow trout, located on the same chromosome copy, then alleles A1 and B1 are co-inherited, to the offspring of the rainbow trout, more often than not.

As used herein, "genetic linkage analysis" refers to a statistical procedure where genotype data, coming from sets of animals comprising parents and their offspring, are investigated in order to test for the presence of genetic linkage between polymorphisms. Genetic linkage analysis can be used in order to assign polymorphisms to chromosomes, provided that the analysis incorporates polymorphisms that have already been assigned to chromosome using, for example, Fluorescence In Situ Hybridisation.

As used herein "Fluorescence In Situ Hybridisation" or "FISH" refers to a technique that detect the presence or absence of specific DNA sequences on chromosomes. FISH can be used in order to assign known DNA polymorphisms to chromosomes.

"Centi-Morgen" is a unit of measurement, used to describe genetic distances, where genetic distance is a measure of the extent to which two polymorphisms are genetically linked.

Linkage disequilibrium (LD) or, more precisely, gametic phase linkage disequilibrium, is used in order to describe the co-inheritance of alleles at genetically linked polymorphisms, at the population level. Assume, for example, two polymorphisms located on the same chromosome; polymorphism A having alleles A1 and A2, and polymorphism B having alleles B1 and B2. All copies of the chromosome in question will harbour a combination of alleles at the two loci (i.e. a haplotype), and there are four possible haplotypes: A1-B1, A1-B2, A2-B1, and A2-B2. The two loci are in said to be LD with each other if the number of A1-B1 and A2-B2 haplotypes within the population are significantly larger or significantly smaller than the number of A1-B2 and A2-B1 haplotypes.

Where a numerical limit or range is stated herein, the endpoints are included. Also, all values and sub ranges within a numerical limit or range are specifically included as if explicitly written out.

Having generally described this invention, a further understanding can be obtained by reference to certain specific examples, which are provided herein for purposes of illustration only, and are not intended to be limiting unless otherwise specified.

EXAMPLES

Example 1: Identification of Single Nucleotide Polymorphisms Predictive for IPN

Two challenge tests were performed, testing the resistance of rainbow trout fry to IPN. Production of and raising of family groups as well as preparation for challenge was performed as previously described in Wetten et al., 2011.

The first test (Challenge 1) was performed with the aim of finding the optimal virus isolate for IPN challenge in rainbow trout. Two separate virus strains were tested; the V-1244 strain which is virulent to Atlantic salmon, and another strain isolated from sea water reared rainbow trout in Norway (Sp-serotype, AGTT11-2). Both strains were tested in triplicate tanks, each containing 100 fish derived from ten separate families of trout. Deceased or moribound individuals were sampled daily. The test was terminated 38 days after initiation of the test. The salmon strain caused 20% overall mortality, whereas the rainbow trout strain was far more virulent, causing 85% overall mortality.

The virus strain isolated from rainbow trout (AGTT11-2) was used in the second challenge (Challenge 2). The aim of this study was to identify SNPs that are diagnostic of the level of IPN resistance in individual rainbow trout. i.e. SNPs associated with IPN-resistance. Fifty different rainbow trout families were included in the test, each represented with a separate tank of 200 fry (mean weight of fry=0.2 grams). All families were bath-challenged by addition of a volume of virus supernatant corresponding to a final virus concentration of approximately $10^6$ TCID$_{50}$/ml water. Deceased or moribound individuals were sampled daily. All fish dying during the trial as well as all survivors collected at termination 40 days post challenge were frozen at $-18°$ C. to enable DNA analysis. The test was terminated 48 days after initiation of the test.

From Challenge 2, 8683 animals were included in the analysis; these animals comprising 46 full-sibling groups originating from 29 male parents and 25 female parents. The number of full-sibling groups per male parent ranged from 1 to 3, as did the number of full-sibling groups per female parent.

The overall mortality rate in Challenge test 2 was 93%. Within full-sibling groups, the mortality rate varied from 67.8% to 99.5%. Of the 8683 challenge-tested individuals, 1723 were genotypet. These 1723 animals comprised (on average) 19 early mortalities and 19 survivors or late mortalities from each of the 46 full-sibling groups. Here, the early mortalities were the first fish to die within their respective full-sibling group, excluding individuals that died prior to day 13 of challenge test 1 (the few deaths occurring before day 13 were assumed not to be due to IPN). The late mortalities were the individuals that died, or were the last to die, within their respective full-sibling groups. Deceased individuals that displayed signs of having been unable to sustain themselves on solid feedstuff were not genotyped; these were identified on the basis of their small size and the lack of red pigments (coming from the feedstuff) in their fins.

DNA was extracted from the tail fin of the to-be-genotyped animals, using a standard method (the DNAeasy 96 kit from QIAGEN (Venlo, the Netherlands)).

The 1723 animals were genotypet using the Axiom Trout genotyping Array, a SNP-chip harbouring 57,501 single nucleotide polymorphisms (SNPs) in 96-well format. This SNP-chip was developed by AquaGen in collaboration with the United Stated Department of Agriculture (USDA) and Affymetrix, and is commercially available from Affymetrix (San Diego, USA). Genotyping was performed using Affymetrix' proprietary Axiom platform, following the Axiom® 2.0 Assay Automated Workflow User Guide (http://media.affymetrix.com/support/downloads/manuals/axiom_2_assay_auto_workflow_user_guide.pdf).

Based on the raw data provided by the Axiom machinery, genotypes were called using the Affymetrix PowerTools software (http://www.affymetrix.com/estore/partners_programs/programs/developer/tools/powertools.aff x).

The analysis and interpretation of the raw data was done according to the Best Practices Workflow provided by Affymetrix (http://www.affymetrix.com/estore/partners_programs/programs/developer/tools/powertools.aff x). SNPs and animals having quality parameters below the default thresholds, provided in the Best Practices Workflow, were not considered for further analyses.

The SNPs were tested individually for association to IPN-resistance, defined as time to death (or end of test for survivors) under challenge-testing. Testing was done through likelihood ratio testing comparing a linear mixed model including random effect of family (including polygenic effects) and a given SNP with a basis model ignoring the SNP effect:

$$H_0: y=1\mu+Zu+e$$

$$H_1: y=1\mu+Zu+Mg+e$$

where y is a vector of time-to-death phenotypes of individuals with known genotypes for a given SNP locus, $\mu$ is the fixed effect of the overall mean, $u \sim N(0, I\sigma_u^2)$ is a vector of random effects of families, Z is an incidence matrix linking individuals to families, $g \sim N(0, \sigma_{SNP}^2)$ is the allele substitution effect of a specific SNP, M is a genotype matrix (with genotypes coded 0, 1 and 2 for the first homozygote, heterozygote and the other homozygote) and $e \sim N(0, I\sigma_e^2)$ is a vector of random residuals. The associated variance components, and the likelihood ratio of the two models were estimated with the DMU software (Madsen & Jensen, 2013), using restricted maximum likelihood (REML) methodology. REML likelihoods for nested models are only comparable when the fixed parts of the two models are identical, and the SNP substitution effect was therefore defined as random.

The likelihood ratio test was performed as follows:

$$D=2lnL_1-2lnL_0 \sim X_1^2$$

where $lnL_0$ and $lnL_0$ are the REML log likelihoods of the $H_0$ and $H_1$ models, respectively. The likelihood ratio testing was done locus by locus, utilizing parallel computing procedures.

In order to correct for multiple testing in a very strict manner, the threshold for declaring significance in the test for association between SNP genotypes and IPN-resistance was divided by 50,000 (the approximated number of high-quality, polymorphic SNPs), i.e. a Bonferroni correction was applied. Thus, an experiment-wide p-value threshold for 0.05 was translated to a p-value threshold of $10^{-6}$ for each individual SNP. In other words, the null hypothesis (H0) stated that no QTL for IPN-resistance was to be found in the investigated material, the alternative hypothesis stated that at least one QTL for IPN-resistance existed in the investigated material, the probability of observing at least one QTL was 0.05 only (5%) if the null hypothesis was true, and an individual SNP needed a p-value below $10^{-6}$ in order to be declared experiment-wide significant.

Linkage maps were produced using the software Lep-MAP (Rastas et. al. 2013). Initially, SNPs were placed into linkage groups through twopoint analysis using the module 'SeparateChromosomes', specifying a LOD threshold of 110 (lodLimit=110), together with the parameters missing Limit=5, achiasmaticMeiosis=0, dataZTolerance=2, malePrior=0.1, femalePrior=0.1 dataTolerance=0.05 sizeLimit=20 (see program options for full description of parameters for this and following steps). Subsequently, unlinked SNPs were added to each group using the module 'JoinSingles', specifying a LOD threshold of 30 (lodLimit=30) and requiring a minimum LOD difference of 10 between candidate linkage group placements (lodDifference=10), together with the parameters achiasmaticMeiosis=0, dataZTolerance=2, malePrior=0.1, femalePrior=0.1, dataTolerance=0.05. Ordering of SNPs in each group was initially performed using the module 'OrderMarkers2' (four iterations), with the parameters missingLimit=5, achiasmaticMeiosis=0, nonNearIdenticalLimit=2 0.01, missingClusteringLimit=0.01, hammingClusteringLimit=0.001, filterIdenticalSubset=25 2, dataZTolerance=2, initError=0.005, initRecombination=0.0001 0.001, alpha=1, MAFLimit=0.05, informativeFamilyLimit=3. Following initial ordering, markers with error rates greater than 0.01 were removed. A final evaluation of this corrected SNP order was carried out using OrderMarkers2' (four iterations) and specifying 'improveOrder=1' in addition to the same parameters used for initial ordering. Chromosome numbers were assigned to the resulting linkage groups according to Phillips et al. (2006). Male and female linkage maps were produced, based on recombination events observed in males and females, respectively.

The SNP sequences, i.e. 71 bp DNA sequences centered on the SNPs, were aligned against a reference sequence for the rainbow trout genome (Berthelot et al. 2014; GenBank reference id of sequence: CCAF010000000). For this, BLAST+ (Altschul et al. 1990, Camacho et al. 2008) was used, with parameters expect=0.1, match score=1, mismatch score=−2, gap-open penalty=0, gap-extend penalty=0. Two input sequences were used for each 71 bp sequence, one for each variant (allele) of the SNP. The CCAF010000000 sub-sequence having the highest BLAST score was accepted as the sub-sequence harbouring the SNP, provided that there were no more than two mismatches between the sub-sequence and the best-fitting of the two 71 bp sequences corresponding to each SNP.

Results

Figure 2:
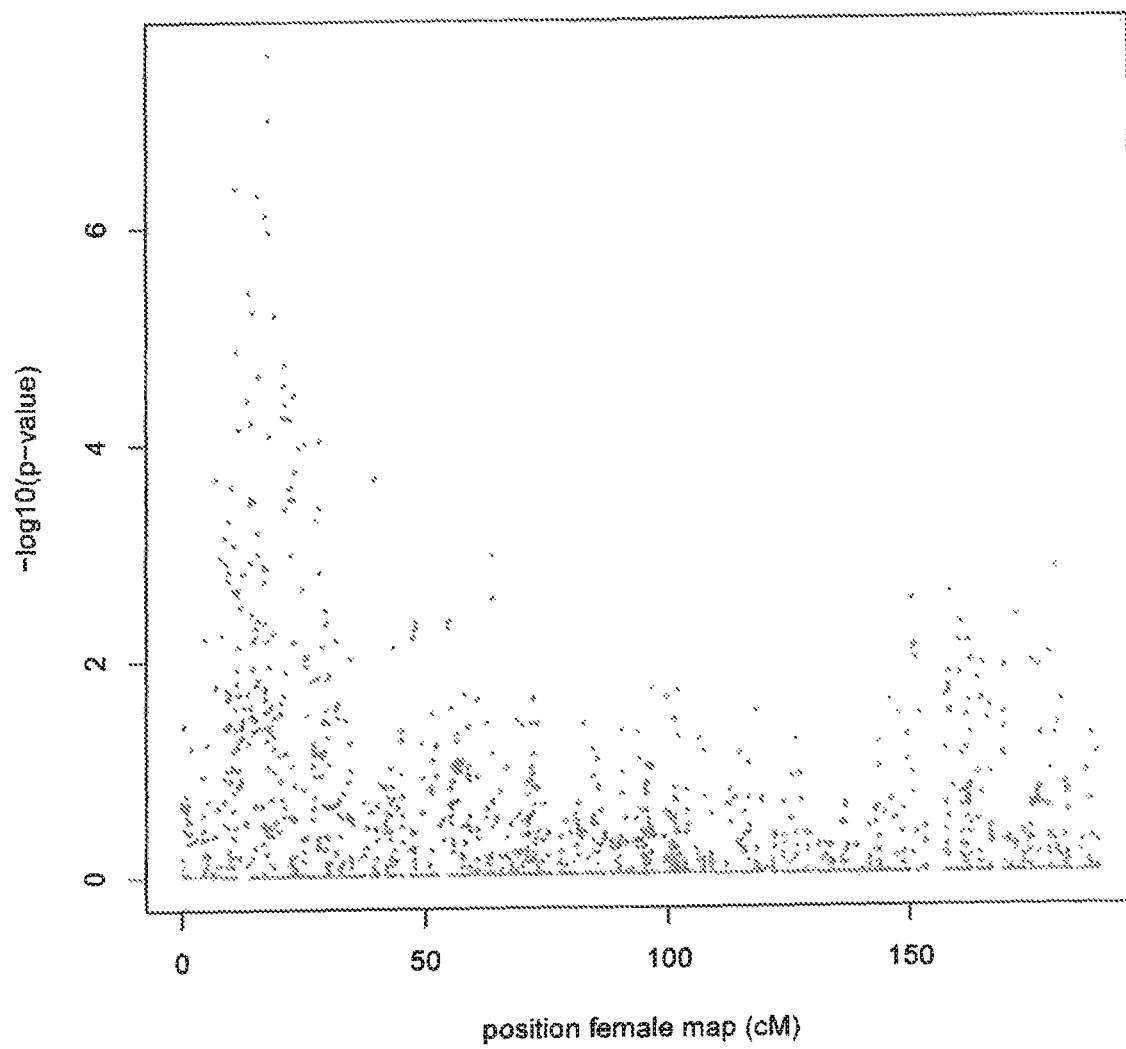
FIG. 2. Significance levels of SNPs, located on rainbow trout chromosome 1, tested for their association to IPN resistance. The SNPs have been ordered according to their position on a genetic map (more precisely, a genetic map based on recombinations occurring in female rainbow trout). cM=centi-Morgan, the standard measure of genetic distance; $-\log 10$(p-value)=the negative of the base-10 logarithms of the SNPs' p-values.

Among the 57,501 SNPs tested for association to IPN-resistance, five SNPs fulfilled the requirement of having p-values below $10^{-6}$, the requirement needed in order to declare experiment-wise statistical significance. As can be seen from FIG. 1, all of these five SNPs are located on one and the same chromosome, namely chromosome 1 following the nomenclature of Palti et al. (2011). Furthermore, as can be seen in FIG. 1, chromosome 1 harboured a large fraction of the SNPs that were individually, but not experiment-wise significant (here, defined as SNPs having p-values below 0.01). As can be seen from FIG. 2, the SNPs on chromosome 1 most strongly associated with IPN-resistance were localised to a sub-region of the chromosome, centred on the most significant SNP. The clustering of significant SNPs within a relatively narrow region of the chromosome indicates strongly that the significantly IPN-associated SNPs are markers for one and the same QTL. Eighty-two SNPs were individually or experiment-wise significant in the test for association with IPN-resistance, while also being located on chromosome 1. Alignment of the DNA sequences pertaining to these SNPs against the rainbow trout genome sequence available in GenBank (Bertheloet et al. 2014; GenBank reference id of sequence: CCAF010000000) revealed that the SNPs resided within a limited number of genome contigs or scaffolds (Table 1).

At any of the significant SNPs, rainbow trout having different SNP genotypes are expected to differ from each other in terms of resistance to IPN. For example, at the most significant SNP, the SNP having Affymetrix SNP identifier AX-89929954 (SNP #1, Table 1), groups of trout homozygous for the allele conferring relative resistance to IPN are expected to have mean survival rates of 45% under conditions similar to the conditions of challenge test 1 (considering only the individuals that were genotyped). In contrast, groups of trout homozygous for the allele not conferring relative resistance to IPN are expected to have mean survival rates of 17% under similar conditions (considering only the individuals that were genotyped), whereas groups of individuals heterozygous at the SNP are expected to have mean survival rates of 36% under similar conditions (considering only the individuals that were genotyped) (see Table 3). Thus, the SNP AX-89929954 can be used as a tool for predicting the level of resistance to IPN of any individual. Here, level of resistance is defined as the level of relative resistance, meaning that an individual will be more resistant to IPN the more copies of the IPN-resistance allele the individual carries at AX-89929954. More precisely, an individual carrying one copy of the IPN-resistance allele (which is cytosine) is expected to be more resistant to IPN than an individual carrying no alleles of the IPN-resistance allele at AX-89929954, given that other determinants of the individuals' resistance to IPN are similar in the two individuals. Similarly, an individual carrying two copies of the IPN-resistance allele at AX-89929954 are expected to be more resistant to IPN than an individual that carries one copy of the IPN-resistance allele at AX-89929954, given that other determinants of the individuals' resistance to IPN are similar in the two individuals. Thus, genotypes at AX-89929954 can be used in order to predict the IPN-resistance of an isolated rainbow trout and in a population of rainbow trouts. Also, since an individual is more likely to pass on (to its offspring) a copy of the IPN-resistance allele at AX-89929954 the more copies of the IPN-resistance allele it carries, genotypes at AX-89929954 can also be used in order to predict the level of IPN-resistance in offspring of an individual. By selecting animals that carry one or two copies of the IPN-resistance allele at AX-89929954 as parents, one may select for higher degrees of IPN resistance in the next generation.

The other SNPs that are individually or experiment-wise significant SNPs, detailed in Table 1, share with AX-89929954 the ability to predict levels of IPN resistance, as can be seen in Table 1 and in Table 3. Furthermore, these SNPs can be used in combination, for example in combinations of two SNPs, in order to form even more powerful predictive tools.

TABLE 3

Survival rates within groups of fish from among the genotyped fish from challenge test 2. Each group consists of all genotyped fish having the genotype in question at the SNP in question. R = IPN resistance allele; A = non-IPN resistance allele; AA, AR, and RR = the three possible genotypes at any particular SNP; NA = not applicable (because no individuals had the genotype in question at the SNP in question). The survival rates are the mean survival rates (±standard error) within the group of animals having the genotype in question at the SNP in question.

| SNP # | Name - Affymetrix ID | p-value | Mean AA +/− SE | Mean AR +/− SE | Mean RR +/− SE |
|---|---|---|---|---|---|
| 1 | AX-89929954 | 2.50E−08 | 0.17 ± 0.01 | 0.36 ± 0.01 | 0.45 ± 0.07 |
| 2 | AX-89918280 | 1.02E−07 | 0.17 ± 0.01 | 0.36 ± 0.01 | 0.38 ± 0.05 |
| 3 | AX-89938309 | 5.10E−07 | 0.1 ± 0.01 | 0.29 ± 0.01 | 0.34 ± 0.02 |
| 4 | AX-89960828 | 7.92E−07 | 0.17 ± 0.01 | 0.32 ± 0.01 | 0.32 ± 0.04 |
| 5 | AX-89930342 | 3.97E−06 | 0.13 ± 0.01 | 0.28 ± 0.01 | 0.34 ± 0.02 |
| 6 | AX-89928530 | 6.06E−06 | 0.13 ± 0.01 | 0.28 ± 0.01 | 0.33 ± 0.02 |
| 7 | AX-89949788 | 6.53E−06 | 0.18 ± 0.01 | 0.35 ± 0.01 | 0.4 ± 0.04 |
| 8 | AX-89928131 | 1.90E−05 | 0.21 ± 0.01 | 0.34 ± 0.01 | 0.36 ± 0.05 |
| 9 | AX-89949832 | 2.89E−05 | 0.18 ± 0.01 | 0.34 ± 0.01 | 0.37 ± 0.03 |
| 10 | AX-89916790 | 4.02E−05 | 0.08 ± 0.02 | 0.24 ± 0.01 | 0.32 ± 0.01 |
| 11 | AX-89973719 | 5.66E−05 | 0.18 ± 0.01 | 0.32 ± 0.01 | 0.35 ± 0.04 |
| 12 | AX-89962023 | 5.70E−05 | 0.2 ± 0.01 | 0.34 ± 0.01 | 0.37 ± 0.06 |
| 13 | AX-89921280 | 5.95E−05 | 0.21 ± 0.01 | 0.34 ± 0.01 | 0.37 ± 0.06 |
| 14 | AX-89931666 | 6.36E−05 | 0.12 ± 0.01 | 0.3 ± 0.01 | 0.26 ± 0.02 |
| 15 | AX-89921585 | 7.21E−05 | 0.04 ± 0.02 | 0.21 ± 0.01 | 0.31 ± 0.01 |
| 16 | AX-89953905 | 8.37E−05 | 0.17 ± 0.01 | 0.32 ± 0.01 | 0.43 ± 0.03 |
| 17 | AX-89952945 | 9.47E−05 | 0.19 ± 0.01 | 0.36 ± 0.01 | 0.28 ± 0.04 |
| 18 | AX-89934682 | 1.00E−04 | 0.19 ± 0.01 | 0.36 ± 0.01 | 0.28 ± 0.05 |
| 19 | AX-89951942 | 0.00010856 | 0.21 ± 0.01 | 0.34 ± 0.01 | 0.38 ± 0.06 |
| 20 | AX-89937020 | 0.00017884 | 0.16 ± 0.01 | 0.3 ± 0.01 | 0.37 ± 0.03 |
| 21 | AX-89924837 | 0.00021198 | 0.21 ± 0.01 | 0.36 ± 0.01 | 0.3 ± 0.12 |
| 22 | AX-89958601 | 0.00025353 | 0.17 ± 0.01 | 0.3 ± 0.01 | 0.37 ± 0.03 |
| 23 | AX-89923477 | 0.00031093 | 0.07 ± 0.03 | 0.22 ± 0.01 | 0.3 ± 0.01 |
| 24 | AX-89959350 | 0.00031728 | 0.07 ± 0.03 | 0.22 ± 0.01 | 0.3 ± 0.01 |
| 25 | AX-89929482 | 0.00032841 | 0.11 ± 0.02 | 0.23 ± 0.01 | 0.31 ± 0.01 |
| 26 | AX-89937712 | 0.00033084 | 0.2 ± 0.01 | 0.33 ± 0.01 | 0.4 ± 0.04 |
| 27 | AX-89949602 | 0.0003479 | 0.08 ± 0.01 | 0.27 ± 0.01 | 0.33 ± 0.02 |
| 28 | AX-89925103 | 0.00038971 | 0.21 ± 0.01 | 0.32 ± 0.01 | 0.41 ± 0.04 |
| 29 | AX-89938051 | 0.00041583 | 0.21 ± 0.01 | 0.35 ± 0.01 | 0.32 ± 0.06 |
| 30 | AX-89924174 | 0.00050314 | 0.21 ± 0.01 | 0.35 ± 0.01 | 0.31 ± 0.06 |
| 31 | AX-89936461 | 0.0005141 | 0.18 ± 0.01 | 0.33 ± 0.01 | 0.26 ± 0.03 |
| 32 | AX-89916703 | 0.00067347 | 0.11 ± 0.01 | 0.27 ± 0.01 | 0.32 ± 0.01 |
| 33 | AX-89935317 | 0.00074987 | 0.1 ± 0.02 | 0.25 ± 0.01 | 0.32 ± 0.01 |
| 34 | AX-89966423 | 0.00085343 | 0.1 ± 0.01 | 0.3 ± 0.01 | 0.28 ± 0.02 |
| 35 | AX-89933348 | 0.00106426 | 0.16 ± 0.02 | 0.26 ± 0.01 | 0.3 ± 0.01 |
| 36 | AX-89969315 | 0.00107414 | 0.18 ± 0.01 | 0.26 ± 0.01 | 0.38 ± 0.02 |
| 37 | AX-89919958 | 0.00113481 | 0.07 ± 0.02 | 0.25 ± 0.01 | 0.31 ± 0.01 |
| 38 | AX-89968417 | 0.00123226 | 0.02 ± 0.02 | 0.2 ± 0.01 | 0.3 ± 0.01 |
| 39 | AX-89946851 | 0.00135127 | 0.18 ± 0.01 | 0.31 ± 0.01 | 0.34 ± 0.03 |
| 40 | AX-89976917 | 0.00143634 | 0.18 ± 0.01 | 0.26 ± 0.01 | 0.37 ± 0.02 |
| 41 | AX-89945446 | 0.00154415 | 0.1 ± 0.02 | 0.25 ± 0.01 | 0.32 ± 0.01 |
| 42 | AX-89919457 | 0.00154766 | 0.21 ± 0.01 | 0.36 ± 0.02 | 0.31 ± 0.04 |
| 43 | AX-89973597 | 0.00155033 | 0.2 ± 0.01 | 0.28 ± 0.01 | 0.37 ± 0.03 |
| 44 | AX-89938138 | 0.00159849 | 0.12 ± 0.03 | 0.21 ± 0.01 | 0.3 ± 0.01 |
| 45 | AX-89971866 | 0.00223949 | 0.02 ± 0.02 | 0.21 ± 0.01 | 0.29 ± 0.01 |
| 46 | AX-89958882 | 0.00228346 | 0.18 ± 0.01 | 0.3 ± 0.01 | 0.31 ± 0.02 |
| 47 | AX-89961273 | 0.00249722 | 0.02 ± 0.02 | 0.21 ± 0.01 | 0.29 ± 0.01 |
| 48 | AX-89944901 | 0.00262016 | 0.18 ± 0.01 | 0.34 ± 0.01 | 0.35 ± 0.03 |
| 49 | AX-89919465 | 0.00282048 | NA | 0.41 ± 0.02 | 0.23 ± 0.01 |
| 50 | AX-89959425 | 0.00298056 | 0.14 ± 0.01 | 0.3 ± 0.01 | 0.37 ± 0.02 |
| 51 | AX-89917102 | 0.00323292 | 0.15 ± 0.02 | 0.26 ± 0.01 | 0.3 ± 0.01 |
| 52 | AX-89959281 | 0.00425635 | 0.23 ± 0.01 | 0.4 ± 0.02 | 0.5 ± 0.2 |
| 53 | AX-89916766 | 0.00451942 | NA | 0.41 ± 0.02 | 0.23 ± 0.01 |
| 54 | AX-89920507 | 0.00457228 | NA | 0.41 ± 0.02 | 0.23 ± 0.01 |
| 55 | AX-89957370 | 0.00460351 | 0.2 ± 0.01 | 0.3 ± 0.01 | 0.26 ± 0.02 |
| 56 | AX-89934009 | 0.00463068 | 0.13 ± 0.01 | 0.27 ± 0.01 | 0.33 ± 0.02 |
| 57 | AX-89929663 | 0.00493969 | 0.14 ± 0.01 | 0.31 ± 0.01 | 0.32 ± 0.02 |
| 58 | AX-89952300 | 0.0052556 | NA | 0.41 ± 0.02 | 0.23 ± 0.01 |
| 59 | AX-89916572 | 0.00571541 | 0.2 ± 0.01 | 0.29 ± 0.01 | 0.37 ± 0.03 |
| 60 | AX-89946911 | 0.00574551 | 0.13 ± 0.02 | 0.24 ± 0.01 | 0.32 ± 0.01 |
| 61 | AX-89974593 | 0.00611967 | 0.12 ± 0.03 | 0.23 ± 0.01 | 0.29 ± 0.01 |
| 62 | AX-89927158 | 0.00627456 | NA | 0.38 ± 0.02 | 0.23 ± 0.01 |
| 63 | AX-89970383 | 0.00628358 | 0.24 ± 0.01 | 0.37 ± 0.02 | 0.64 ± 0.12 |
| 64 | AX-89965404 | 0.00638481 | NA | 0.41 ± 0.02 | 0.23 ± 0.01 |
| 65 | AX-89955634 | 0.00639828 | NA | 0.41 ± 0.02 | 0.23 ± 0.01 |
| 66 | AX-89932926 | 0.00657013 | 0.13 ± 0.02 | 0.25 ± 0.01 | 0.31 ± 0.01 |
| 67 | AX-89941493 | 0.00675854 | 0.19 ± 0.01 | 0.27 ± 0.01 | 0.3 ± 0.02 |
| 68 | AX-89943031 | 0.0067705 | 0.12 ± 0.03 | 0.21 ± 0.01 | 0.31 ± 0.01 |

TABLE 3-continued

Survival rates within groups of fish from among the genotyped fish from challenge test 2. Each group consists of all genotyped fish having the genotype in question at the SNP in question. R = IPN resistance allele; A = non-IPN resistance allele; AA, AR, and RR = the three possible genotypes at any particular SNP; NA = not applicable (because no individuals had the genotype in question at the SNP in question). The survival rates are the mean survival rates (±standard error) within the group of animals having the genotype in question at the SNP in question.

| SNP | | | Survival rates in IPN challenge test | | |
|---|---|---|---|---|---|
| # | Name - Affymetrix ID | p-value | Mean AA +/− SE | Mean AR +/− SE | Mean RR +/− SE |
| 69 | AX-89957682 | 0.00689041 | 0.09 ± 0.03 | 0.24 ± 0.01 | 0.29 ± 0.01 |
| 70 | AX-89960611 | 0.00728331 | 0.17 ± 0.01 | 0.33 ± 0.01 | 0.35 ± 0.02 |
| 71 | AX-89950199 | 0.00747825 | 0.19 ± 0.02 | 0.27 ± 0.01 | 0.3 ± 0.02 |
| 72 | AX-89928407 | 0.00764258 | 0.08 ± 0.02 | 0.24 ± 0.01 | 0.3 ± 0.01 |
| 73 | AX-89962035 | 0.00770092 | NA | 0.41 ± 0.02 | 0.23 ± 0.01 |
| 74 | AX-89931951 | 0.00796054 | 0.21 ± 0.01 | 0.36 ± 0.02 | 0.29 ± 0.04 |
| 75 | AX-89976536 | 0.00852971 | 0.21 ± 0.01 | 0.36 ± 0.01 | 0.29 ± 0.04 |
| 76 | AX-89916801 | 0.00898601 | 0.02 ± 0.02 | 0.22 ± 0.01 | 0.28 ± 0.01 |
| 77 | AX-89929085 | 0.0094422 | 0.02 ± 0.02 | 0.22 ± 0.01 | 0.28 ± 0.01 |
| 78 | AX-89925267 | 0.0099745 | 0.2 ± 0.05 | 0.22 ± 0.01 | 0.29 ± 0.01 |
| 160 | chr1__7515539 | 3.10E−07 | 0.18 ± 0.01 | 0.37 ± 0.02 | 0.38 ± 0.05 |
| 161 | chr1__7108873 | 4.56E−07 | 0.18 ± 0.01 | 0.36 ± 0.02 | 0.45 ± 0.08 |
| 162 | chr1__6864558 | 4.56E−07 | 0.18 ± 0.01 | 0.36 ± 0.02 | 0.45 ± 0.08 |
| 163 | chr1__7186663 | 9.66E−07 | 0.18 ± 0.01 | 0.36 ± 0.02 | 0.45 ± 0.08 |
| 164 | chr1__6730531 | 1.26E−06 | 0.18 ± 0.01 | 0.33 ± 0.02 | 0.34 ± 0.04 |
| 165 | chr1__27891953 | 1.38E−06 | 0.22 ± 0.01 | 0.31 ± 0.02 | 0.66 ± 0.06 |
| 166 | AX-89953259 | 1.59E−06 | 0.18 ± 0.01 | 0.33 ± 0.02 | 0.33 ± 0.04 |
| 167 | chr1__6740481 | 1.76E−06 | 0.18 ± 0.01 | 0.33 ± 0.02 | 0.33 ± 0.04 |
| 168 | chr1__6770611 | 1.76E−06 | 0.18 ± 0.01 | 0.33 ± 0.02 | 0.33 ± 0.04 |
| 169 | chr1__7412807 | 2.16E−06 | 0.18 ± 0.01 | 0.36 ± 0.02 | 0.38 ± 0.05 |
| 170 | chr1__7360179 | 2.18E−06 | 0.18 ± 0.01 | 0.36 ± 0.02 | 0.38 ± 0.05 |
| 171 | chr1__7411803 | 2.18E−06 | 0.18 ± 0.01 | 0.36 ± 0.02 | 0.38 ± 0.05 |
| 172 | chr1__7431445 | 2.18E−06 | 0.18 ± 0.01 | 0.36 ± 0.02 | 0.38 ± 0.05 |
| 173 | chr1__7433199 | 2.18E−06 | 0.18 ± 0.01 | 0.36 ± 0.02 | 0.38 ± 0.05 |
| 174 | chr1__7441254 | 2.18E−06 | 0.18 ± 0.01 | 0.36 ± 0.02 | 0.38 ± 0.05 |
| 175 | chr1__7441877 | 2.18E−06 | 0.18 ± 0.01 | 0.36 ± 0.02 | 0.38 ± 0.05 |
| 176 | chr1__7533570 | 2.18E−06 | 0.18 ± 0.01 | 0.36 ± 0.02 | 0.38 ± 0.05 |
| 177 | chr1__6834898 | 2.19E−06 | 0.18 ± 0.01 | 0.32 ± 0.02 | 0.33 ± 0.04 |
| 178 | chr1__6730142 | 2.23E−06 | 0.18 ± 0.01 | 0.33 ± 0.02 | 0.33 ± 0.04 |
| 179 | chr1__6746052 | 2.23E−06 | 0.18 ± 0.01 | 0.33 ± 0.02 | 0.33 ± 0.04 |
| 180 | chr1__6794061 | 2.23E−06 | 0.18 ± 0.01 | 0.33 ± 0.02 | 0.33 ± 0.04 |
| 181 | chr1__7399212 | 2.95E−06 | 0.18 ± 0.01 | 0.36 ± 0.02 | 0.38 ± 0.05 |
| 182 | chr1__7442637 | 3.02E−06 | 0.18 ± 0.01 | 0.36 ± 0.02 | 0.38 ± 0.05 |
| 183 | chr1__7358019 | 3.11E−06 | 0.18 ± 0.01 | 0.36 ± 0.02 | 0.38 ± 0.05 |
| 184 | chr1__7709828 | 3.45E−06 | 0.2 ± 0.01 | 0.3 ± 0.01 | 0.77 ± 0.07 |
| 185 | chr1__7598090 | 5.65E−06 | 0.19 ± 0.01 | 0.36 ± 0.02 | 0.38 ± 0.05 |
| 186 | chr1__7626471 | 7.50E−06 | 0.19 ± 0.01 | 0.37 ± 0.02 | 0.38 ± 0.05 |
| 187 | chr1__7598743 | 7.56E−06 | 0.19 ± 0.01 | 0.36 ± 0.02 | 0.38 ± 0.05 |
| 188 | chr1__7670293 | 9.90E−06 | 0.19 ± 0.01 | 0.36 ± 0.02 | 0.38 ± 0.05 |
| 189 | chr1__7670561 | 9.90E−06 | 0.19 ± 0.01 | 0.36 ± 0.02 | 0.38 ± 0.05 |
| 190 | chr1__7647634 | 1.22E−05 | 0.19 ± 0.01 | 0.36 ± 0.02 | 0.38 ± 0.05 |
| 191 | chr1__7356089 | 2.28E−05 | 0.18 ± 0.01 | 0.36 ± 0.02 | 0.39 ± 0.04 |
| 192 | chr1__8109044 | 3.84E−05 | 0.18 ± 0.01 | 0.35 ± 0.02 | 0.4 ± 0.04 |
| 193 | chr1__10439048 | 4.96E−05 | 0.21 ± 0.01 | 0.35 ± 0.02 | 0.37 ± 0.08 |
| 194 | chr1__8142346 | 5.19E−05 | 0.19 ± 0.01 | 0.36 ± 0.02 | 0.4 ± 0.04 |
| 195 | chr1__8092208 | 8.17E−05 | 0.19 ± 0.01 | 0.35 ± 0.02 | 0.4 ± 0.04 |
| 196 | chr1__8138683 | 8.17E−05 | 0.19 ± 0.01 | 0.35 ± 0.02 | 0.4 ± 0.04 |
| 197 | chr1__8139206 | 8.17E−05 | 0.19 ± 0.01 | 0.35 ± 0.02 | 0.4 ± 0.04 |
| 198 | chr1__8139744 | 8.17E−05 | 0.19 ± 0.01 | 0.35 ± 0.02 | 0.4 ± 0.04 |
| 199 | chr1__8140789 | 8.17E−05 | 0.19 ± 0.01 | 0.35 ± 0.02 | 0.4 ± 0.04 |
| 200 | chr1__8141687 | 8.17E−05 | 0.19 ± 0.01 | 0.35 ± 0.02 | 0.4 ± 0.04 |
| 201 | chr1__8154917 | 8.17E−05 | 0.19 ± 0.01 | 0.35 ± 0.02 | 0.4 ± 0.04 |
| 202 | chr1__7454708 | 8.74E−05 | 0.18 ± 0.01 | 0.33 ± 0.02 | 0.42 ± 0.04 |
| 203 | chr1__7504847 | 8.74E−05 | 0.18 ± 0.01 | 0.33 ± 0.02 | 0.42 ± 0.04 |
| 204 | chr1__7505686 | 8.74E−05 | 0.18 ± 0.01 | 0.33 ± 0.02 | 0.42 ± 0.04 |
| 205 | chr1__7505817 | 8.74E−05 | 0.18 ± 0.01 | 0.33 ± 0.02 | 0.42 ± 0.04 |
| 206 | chr1__8202031 | 8.96E−05 | 0.19 ± 0.01 | 0.36 ± 0.02 | 0.4 ± 0.04 |
| 207 | chr1__8228173 | 8.96E−05 | 0.19 ± 0.01 | 0.36 ± 0.02 | 0.4 ± 0.04 |
| 208 | chr1__8309469 | 8.96E−05 | 0.19 ± 0.01 | 0.36 ± 0.02 | 0.4 ± 0.04 |
| 209 | chr1__8163977 | 8.96E−05 | 0.19 ± 0.01 | 0.36 ± 0.02 | 0.4 ± 0.04 |
| 210 | chr1__27786931 | 9.68E−05 | 0.22 ± 0.01 | 0.3 ± 0.02 | 0.61 ± 0.06 |
| 211 | chr1__8194629 | 0.00010535 | 0.19 ± 0.01 | 0.35 ± 0.02 | 0.4 ± 0.04 |
| 212 | chr1__7505259 | 0.00010824 | 0.18 ± 0.01 | 0.33 ± 0.02 | 0.42 ± 0.04 |
| 213 | chr1__8474659 | 0.00014238 | 0.19 ± 0.01 | 0.35 ± 0.02 | 0.39 ± 0.04 |
| 214 | chr1__8282602 | 0.00014575 | 0.19 ± 0.01 | 0.35 ± 0.02 | 0.4 ± 0.04 |
| 215 | chr1__8306806 | 0.00014575 | 0.19 ± 0.01 | 0.35 ± 0.02 | 0.4 ± 0.04 |
| 216 | chr1__8341618 | 0.00014575 | 0.19 ± 0.01 | 0.35 ± 0.02 | 0.4 ± 0.04 |
| 217 | chr1__8343786 | 0.00014575 | 0.19 ± 0.01 | 0.35 ± 0.02 | 0.4 ± 0.04 |

TABLE 3-continued

Survival rates within groups of fish from among the genotyped fish from challenge test 2. Each group consists of all genotyped fish having the genotype in question at the SNP in question. R = IPN resistance allele; A = non-IPN resistance allele; AA, AR, and RR = the three possible genotypes at any particular SNP; NA = not applicable (because no individuals had the genotype in question at the SNP in question). The survival rates are the mean survival rates (±standard error) within the group of animals having the genotype in question at the SNP in question.

| SNP | | | Survival rates in IPN challenge test | | |
|---|---|---|---|---|---|
| # | Name - Affymetrix ID | p-value | Mean AA +/− SE | Mean AR +/− SE | Mean RR +/− SE |
| 218 | chr1__8345836 | 0.00014575 | 0.19 ± 0.01 | 0.35 ± 0.02 | 0.4 ± 0.04 |
| 219 | chr1__8350569 | 0.00014575 | 0.19 ± 0.01 | 0.35 ± 0.02 | 0.4 ± 0.04 |
| 220 | chr1__8402403 | 0.00014575 | 0.19 ± 0.01 | 0.35 ± 0.02 | 0.4 ± 0.04 |
| 221 | AX-89962103 | 0.00016979 | 0.35 ± 0.02 | 0.26 ± 0.02 | 0.13 ± 0.02 |
| 222 | chr1__8279302 | 0.00018144 | 0.19 ± 0.01 | 0.35 ± 0.02 | 0.4 ± 0.04 |
| 223 | chr1__8334901 | 0.00020083 | 0.19 ± 0.01 | 0.35 ± 0.02 | 0.4 ± 0.04 |
| 224 | chr1__7561600 | 0.00023783 | 0.19 ± 0.01 | 0.32 ± 0.02 | 0.42 ± 0.04 |
| 225 | AX-89956272 | 0.00026395 | 0.31 ± 0.01 | 0.22 ± 0.02 | 0.07 ± 0.03 |
| 226 | chr1__7938827 | 0.00026777 | 0.2 ± 0.01 | 0.3 ± 0.02 | 0.44 ± 0.05 |
| 227 | chr1__10810229 | 0.00029614 | 0.19 ± 0.01 | 0.37 ± 0.02 | 0.29 ± 0.05 |
| 228 | chr1__11007071 | 0.00029787 | 0.19 ± 0.01 | 0.37 ± 0.02 | 0.29 ± 0.05 |
| 229 | chr1__10884171 | 0.00029812 | 0.19 ± 0.01 | 0.37 ± 0.02 | 0.29 ± 0.05 |

Example 2: Creating Rainbow Trout with Increased Resistance to IPN

A tissue sample is taken from each potential parent, i.e. from each rainbow trout that is a candidate parent for the creation of the said trout with increased resistance to IPN. The tissue sample may be taken using any of several available techniques for non-invasive sampling from live trout. For example, the sample may be a piece of the trout's adipose fin, cut using scissors or a scalpel, or it may be a biopsy of muscle tissue, taken using a biopsy punch such as the 3.0 mm Biopsy Punch with Plunger (BPP-30F) from Brymill (Basingstoke, UK). The sample can also be a few scales collected using a forceps. Following sampling, the tissue samples should be frozen down immediately, and kept in a frozen state until DNA extraction, or alternatively placed in ethanol for long term storage in the freezer. Scale samples may be dried on a piece of paper before storage. At the time of sampling, the potential parents must be physically tagged, using for example Passive Integrated Transponder (PIT) tags. Physical tagging will facilitate the later retrieval of the individuals selected using the method.

DNA is extracted from the tissue sample, using any of several available methods for extracting high-quality DNA from trout samples. For example, DNA may be extracted using the DNAeasy kit from QIAGEN (Venlo, the Netherlands), following the protocol supplied with that kit.

The extracted DNA is genotyped for at least one of the single nucleotide polymorphisms (SNPs) specified in Table 1. For example, the extracted DNA may be genotyped using the SNP AX-89929954 (SNP #1). Genotyping may be performed using any well-established method for genotyping SNPs. For example, genotyping may be performed using the iPlex® protocol on the MassARRAY® system from Sequenom (San Diego, USA). For genotyping of SNP AX-89929954 using the iPlex protocol, these primers can be used:

Forward PCR primer:
(SEQ ID NO: 157)
ACGTTGGATGTCCACAGTCCACATGCTTTG,

Reverse PCR primer:
(SEQ ID NO: 158)
ACGTTGGATGGGAAAGAAACAGTGATAGGC,

Extension primer:
(SEQ ID NO: 159)
CACACAACTGTGTGTCAAAT

All other experimental parameters are according to the iPlex protocol. The iPlex protocol may be applied on a multiplex of several SNPs, in which case experimental parameters, including the primer sequences, may have to be adjusted according to the properties other SNPs within the multiplex. These adjustments are made using the Assay Design Suite software from Sequenom (https://ww.mysequenom.com/Tools).

The raw data from iPlex genotyping is processed using the Typer software from Sequenom. The genotyped samples will cluster into three distinct and well-defined clusters corresponding to the three genotypes, provided that all three genotypes are represented within the genotyped samples.

Applying the steps laid out above, some of the genotyped trout may be found to have two copies of the cytosine (C) allele, while other may have two copies of the adenine (A) allele. Yet other may have one copy of each allele (AC). The parents having two copies of C (i.e. having genotype CC) will be selected as parents. The offspring of these parents will all be homozygous for allele C at SNP AX-89929954, meaning that they will all be homozygous (CC) for the allele associated with increased resistance to IPN. Under conditions similar to the conditions used in the experiment for challenge test 2 described in Example 1 above, such (CC) animals are expected to have a survival rate of 45%, while animals originating from randomly selected parents will have an expected survival rate of 26%.

If no individuals are found to have genotype CC, individuals with genotype AC may be selected as parents. If the parental candidates (i.e. the genotyped animals) were a random subset of the population from which they originated, using these AC animals as parents is also expected to produce offspring with increased resistance to IPN.

The method may be applied using any of the SNPs listed in Table 1. The method may also be applied using a combination of two or more SNPs. For example, one may genotype SNPs AX-89929954 and AX-89918280 (SNP #2), and use as parents the individuals having genotype CC at AX-89929954 and genotype GG at AX-89918280.

Following the identification of parents using the method, these parents are retrieved by sorting them out from the tank wherein they are located (usually done while moving each fish over to another tank). Offspring are produced, and fertilised eggs are raised, using standard aquaculture methods.

Example 3: Validation Experiments of the Results Underlying the Invention

Two additional challenge tests (Challenge test 3 and 4) were carried out, in order to validate the association between IPN resistance and alleles at the DNA-polymorphisms of the invention. The tests were carried out in two 100 liter tanks, and in each tank a group of rainbow trout individuals was tested for resistance against one of two strains of the IPN virus. The two strains were 1) a strain (AGT11-2) of serotype Sp isolated from Norwegian sea-water-reared rainbow trout; the same strain that was used in Example 1, and 2) a strain of serotype Wb isolated from an IPN outbreak in rainbow trout in Chile. Each tank contained approx. 12 rainbow trout fry from each of 133 full-siblings groups. The same set of full-sibling groups were used in both tests. The test was carried out 1 week after first feeding (i.e. after transition to solid feed). The fish were acclimatised and start-fed at the test site. At the commencement of the tests, the water volume was reduced to ½ the original volume, whereupon 100 ml of the respective virus isolate was added to each tank, in order to obtain a final concentration equal to a $TCID_{50}$ of $10^5$ virus particles per ml of water. Three hours after addition of virus, the water volume was returned to the pre-challenge level (aeration of the water was maintained during these three hours). Mortalities were sampled and recorded two times a day throughout the test period. DNA was extracted from sampled test fish, using a standard protocol. Both tests were terminated 28 days after test start. At that time, the daily mortality rates were 0.9% (Sp) and 0.19% (Wb), and decreasing. In contrast, at the peak of the mortality curve, daily mortalities had been 10.1% (Sp) and 1.56% (Wb). In other words, at the termination of the tests, the survival curve had flattened out, and it is reasonable to assume that most of the fish that survived the test period would have survived also if the test period had been prolonged. The accumulated mortalities were 70.0% (Sp) and 9.38% (Wb). All animals from the Sp test (1603 animals) and all mortalities from the Wb test (174 animals) were sampled and genotyped for four of the DNA polymorphisms of the Invention. Genotyping was performed using the iPLEX genotyping system from Agena Bioscience (San Diego, USA) (the iPLEX system was formerly owned by Sequenom, San Diego, USA). PCR- and extension primers for iPLEX genotyping were designed using the Assay Design Suite v2.0 (available at www.mysequenom.com/Tools), using default settings and all four DNA polymorphisms were genotyped in one and the same multiplex reaction. As can be seen in Table 4, frequencies of the alleles designates as IPN-resistance alleles were significantly higher in the survivors from the Sp test than in mortalities from the Sp test, for all four polymorphisms. Similarly, frequencies of the alleles designated as IPN-resistance alleles were significantly higher in the survivors from the Wb test than in the mortalities from the Wb test. Here, statistical significance was tested by applying a logistic regression of the number of IPN-resistance alleles on the binary survival/non-survival, for each polymorphism. Table 4 contains the p-values from this test, for all four polymorphisms. For the Wb test, where only mortalities were recorded, genotype counts among the 1416 survivors were estimated by assuming that overall allele frequencies were the same in the Wb test as in the Sp test (a reasonable assumption, given that the two challenge tests contained animals from the same families, in the same proportions), and by further assuming that each polymorphism was in Hardy-Weinberg equilibrium.

The validation experiment confirmed that a statistically significant association exists between IPN resistance and alleles at all four investigated polymorphisms. Furthermore, the association was valid also when the IPN virus strain used in the initial discovery of the Invention (a strain of serotype Sp) was replaced with a different strain (of serotype Wb, West Buxon). It follows that the association between DNA polymorphisms and IPN resistance is reproducible and independent of virus strain.

It is a natural and necessary consequence of these findings that the DNA polymorphisms of the Invention may be used in order to create rainbow trout with increased resistance to IPN. For example, one may use DNA polymorphism AX-89929954 in order to screen a number of rainbow trout individuals. Having identified one male one female which are both homozygous for the IPN-resistance allele (i.e. they both have genotype CC), these two animals may be mated, and all offspring coming from that mating will have genotype CC according to the rules of Mendel. These individuals will be expected to be more resistant to IPN than random (but otherwise comparable) individuals coming from the same population of rainbow trout, provided that the mortality allele (A in the case of AX-89929954) also exists in the population.

TABLE 4

Results from experiment validating the association between IPN-resistance and the polymorphisms of the Invention. For each of four polymorphisms, the table contains: 1) the identity of the resistance- and mortality alleles (as defined in Table 1 and in Table 2), 2) counts of animals having either of the three possible genotypes, within the subgroups of Sp survivors (SP_SURV), So mortalities (SP_MORT), and Wb mortalities (WB_MORT), 3) p-values from the regression of number of IPN-resistance alleles on the binary trait survival/non-survival.

| | SP_SURV | SP_MORT | WB_SURV* | WB_MORT |
|---|---|---|---|---|
| AX-89929954 IPN-resistance-/non_IPN resistance alleles: C/A | | | | |
| CC | 139 | 249 | 262 | 31 |
| AC | 187 | 370 | 694 | 52 |
| AA | 99 | 472 | 460 | 81 |

TABLE 4-continued

Results from experiment validating the association between IPN-resistance and the polymorphisms of the Invention. For each of four polymorphisms, the table contains: 1) the identity of the resistance- and mortality alleles (as defined in Table 1 and in Table 2), 2) counts of animals having either of the three possible genotypes, within the subgroups of Sp survivors (SP_SURV), So mortalities (SP_MORT), and Wb mortalities (WB_MORT), 3) p-values from the regression of number of IPN-resistance alleles on the binary trait survival/non-survival.

|  | SP_SURV | SP_MORT | WB_SURV* | WB_MORT |
|---|---|---|---|---|
| Sp-test | p-value |  | $5.1*10^{-11}$ |  |
| Wb-test | p-value |  | $5.0*10^{-3}$ |  |
| AX-89960828 |  |  |  |  |
| IPN-resistance-/non_IPN |  |  |  |  |
| resistance alleles: |  |  |  |  |
| T/C |  |  |  |  |
| TT | 92 | 158 | 216 | 13 |
| CT | 235 | 466 | 674 | 70 |
| CC | 116 | 517 | 527 | 87 |
| Sp-test | p-value |  | $7.6*10^{-11}$ |  |
| Wb-test | p-value |  | $1.3*10^{-4}$ |  |
| AX-89918280 |  |  |  |  |
| IPN-resistance-/non_IPN |  |  |  |  |
| resistance alleles: |  |  |  |  |
| G/A |  |  |  |  |
| GG | 126 | 214 | 316 | 20 |
| AG | 244 | 536 | 706 | 82 |
| AA | 73 | 383 | 394 | 69 |
| Sp-test | p-value |  | $2.1*10^{-11}$ |  |
| Wb-test | p-value |  | $5.9*10^{-5}$ |  |
| AX-89938309 |  |  |  |  |
| resistance-/mortality- |  |  |  |  |
| alleles: |  |  |  |  |
| T/G |  |  |  |  |
| TT | 112 | 171 | 230 | 14 |
| GT | 228 | 428 | 681 | 53 |
| GG | 102 | 505 | 505 | 103 |
| Sp-test | p-value |  | $6.8*10^{-15}$ |  |
| Wb-test | p-value |  | $1.2*10^{-8}$ |  |

*The counts for WB_SURV were estimated as described above.

Figure 3:
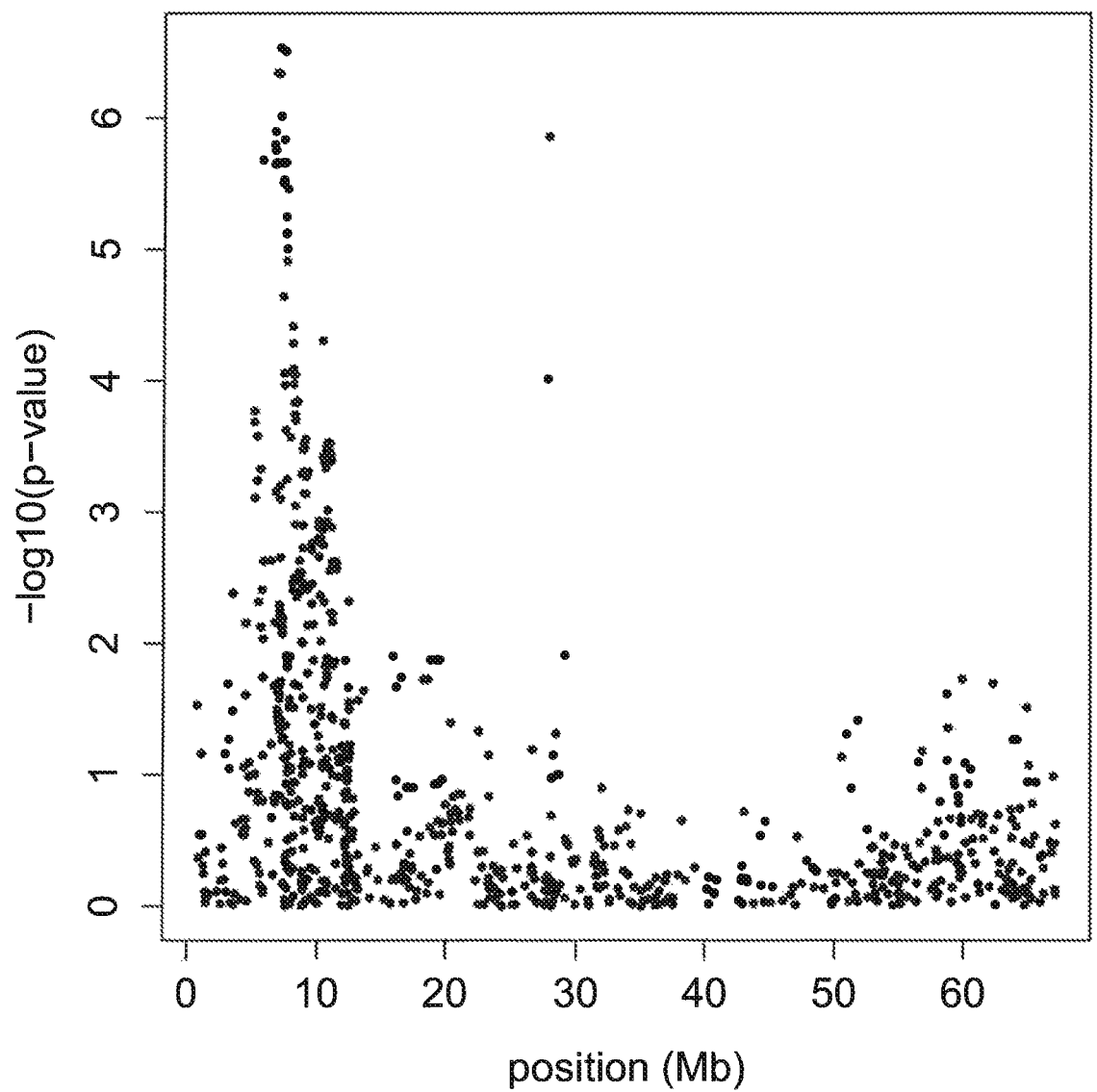
FIG. 3. Significance levels of SNPs, obtained from a study identifying additional SNPs associated with IPN-resistance (Example 3). Novel and already known SNPs on chromosome 1 were tested for their association to IPN-resistance. Values on the x-axis are positions, in basepairs, of SNPs along a DNA reference sequence of rainbow trout chromosome 1, values on the y-axis are the negative of the base-10 logarithm of p-values.

Example 4: Identification and Testing of Additional SNPs Associated with IPN Resistance Twelve individual rainbow trout from AquaGen's population of rainbow trout were whole-genome sequenced using HiSeq2000 from Illumina (San Diego, USA); see Palti et al. (2015). Sequence reads originating from these 12 animals were aligned to the publicly available reference genome sequence for rainbow trout (Berthelot et al. 2014), using bowtie2 (Langmead and Salzberg, 2012). Prior to alignment of the Illumina sequence reads, the sub-sequences (scaffolds and contigs) of the reference sequence were merged and ordered by the co-alignment of sub-sequences to Atlantic salmon chromosome sequences (submitted to GenBank); the two species are closely related and display a large degree of synteny. From the aligned sequence reads, SNPs were identified using freebayes (Garrion and Marth, 2012). The set of (putative) SNPs was filtered in freebayes using the following parameter string: "--no-indels --no-mnps --no-complex --min-mapping-quality 30--read-mismatch-limit 2--read-indel-limit 1". For each filtered SNP, genotypes in the 12 sequenced animals were deduced using freebayes. The genotypes were compared to genotypes at one of the original SNPs of the Invention (AX-89929954), calculating for each filtered SNP the square of the correlation coefficient between that SNP and AX-89929954. The square of the correlation coefficient ($r^2$) between two DNA polymorphisms is a measure of the amount of linkage disequilibrium between the DNA polymorphisms; the higher $r^2$, the more correlated genotypes at the two DNA polymorphisms are. Noting that high levels of $r^2$ was predominantly observed for DNA polymorphisms that was no more than 3 million base pairs (3 Mb) distant from AX-89929954, most SNPs that were more than 3 Mb from AX-89929954 was removed, as were all SNPs having an $r^2$ value lower than 0.2. Furthermore, SNPs having $r^2$ values above 0.5 were prioritized, as were SNPs no more than 500 bp from a gene region (a gene region was defined as a region containing a BLASTN hit, when BLASTN was run against the most recent version of the RefSeq-RNA database, with default BLASTN parameter values). In the end, a subset of 500 SNPs was selected, and genotyped using KASP chemistry, implemented through the SNPline system from LGC Genomics (http://www.lgc-group.com/products/genotyping-instruments/snpline/#.VkNMKLcvdhE). Genotyping was done on the same genetic material as described in Example 1 (1723 animals from an IPN challenge test), and associations between genotypes and IPN resistance were tested for in the same manner as described in Example 1. Individual SNPs displaying chi-square-distributed test statistics larger than 13.0 were defined as being so strongly associated to IPN, they could be used as tools for selecting IPN resistant animals. In FIG. 3, the negative of the logarithm of p-values (H0: genotypes are not associated with IPN resistance, H1: genotypes are associated with IPN resistance) are plotted against positions on the "physically ordered" rainbow trout reference genome, for all DNA polymorphisms tested either as part of the experiment described in Example 1 or as part of the validation study described here. The figure illustrates that the polymorphisms most strongly associated to IPN resistance are all located within a narrow region, meaning that the most likely position of the causative DNA polymorphisms underlying the QTL is relatively well defined, and that any other DNA polymorphisms located within the QTL region (the "peak region" of the graph), if associated with IPN, are likely to be markers for one and the same underlying causative mutation.

CERTAIN REFERENCES CITED IN THE APPLICATION

Altschul S F, Gish W, Miller W, Myers E W, and Lipman D J (1990) Basic local alignment search tool. J. Mol. Biol. 215:403-410.

Berthelot C, Brunet F, Chalopin D, Juanchich A, Bernard M et al. (2014) The rainbow trout genome provides novel insights into evolution after whole-genome duplication in vertebrates. Nature Communications 5: 3657.

Camacho C, Coulouris G, Avagyan V, Ma N, Papadopoulos J et al. (2008) BLAST+: architecture and applications. BMC Bioinformatics 10:421.

Garrison E, Marth G. Haplotype-based variant detection from short-read sequencing (2012) arXiv preprint arXiv: 1207.3907 [q-bio. GN]

Langmead B, Salzberg S L (2012) Fast gapped-read alignment with Bowtie 2. Nature Methods 9:357-359.

Madsen P, Su G, Labouriau R, and Christensen O F (2010) DMU—A package for analysing multivariate mixed models. Proceedings from the 9th World Congress on Genetics Applied to Livestock Production (WCGALP); http://www.kongressband.de/wcgalp2010/assets/pdf/0732.pdf Palti Y, Genet C, Luo M C, Charlet A, Gao G et al. (2011) A first generation integrated map of the rainbow trout genome. BMC Genomics 12:180.

Palti Y, Gao G, Liu S, Kent M P, Lien S, Miller M R, Rexroad C E III, Moen T (2015) The development and characterization of a 57K single nucleotide polymorphism array for rainbow trout. Molecular Ecology Resources 15: 662-672.

Phillips R B, Nichols K M, Dekoning J H, Morasch M R, Keatley K A et al. (2006) Assignment of rainbow trout linkage groups to specific chromosomes. Genetics 174: 1661-1670.

Rastas P, Paulin L, Hanski I, Lehtonen R, and Auvinen P (2013) Lep-MAP: fast and accurate linkage map construction for large SNP datasets. Bioinformatics 29: 3128-34.

Wetten M, Kjøglum S, Fjalestad K T, Skjærvik O, Storset A. (2011) Genetic variation in resistance to infectious pancreatic necrosis in rainbow trout (*Onchorhynchus mykiss*) after a challenge test. Aquaculture Research 1-7.

The invention claimed is:

1. A method for obtaining rainbow trout having increased resistance to infectious pancreatic necrosis (IPN), said method comprising:
   a) providing an initial population of rainbow trout;
   b) obtaining a nucleic acid sample from at least one individual rainbow trout within said initial population;
   c) detecting in each of said nucleic acid samples the presence of at least one allele conferring IPN resistance ("IPN resistance allele") within the genome of said rainbow trout, wherein the at least one IPN resistance allele is an allele of at least one single nucleotide polymorphism (SNP) selected from the SNPs listed in the following table:

| SNP # | Name Affymetrix ID | SEQ ID NO: | GenBank Contig | Position in GenBank Contig | dbSNP ss-No (SS#) | IPN resistance allele | Non-IPN resistance allele |
|---|---|---|---|---|---|---|---|
| 1 | AX-89929954 | 1 | FR904293.1 | 1651243 | 1398298005 | C | A |
| 2 | AX-89918280 | 2 | FR904293.1 | 1353665 | 1399389616 | G | A |
| 4 | AX-89960828 | 4 | FR932837.1 | 3160 | 1399779599 | T | C ; | d) selecting a rainbow trout from said initial population based on the presence of the at least one IPN resistance allele in the nucleic acid samples; and
   e) mating said selected rainbow trout with a second rainbow trout to produce progeny rainbow trout comprising increased resistance to IPN.

2. The method according to claim 1, said method comprising:
   obtaining a nucleic acid sample from at least two individual rainbow trout within said initial population,
   detecting the presence of at least one IPN resistance allele within the genome of said at least two rainbow trout,
   selecting a mating pair of rainbow trout from said initial population based on the presence of the at least one IPN resistance allele in the nucleic acid samples of both rainbow trout within said mating pair; and
   mating said selected mating pair of rainbow trout to produce progeny rainbow trout comprising increased resistance to IPN.

3. The method according to claim 2, wherein at least one rainbow trout within said mating pair is homozygous for the IPN resistance allele.

4. The method according to claim 3, wherein each rainbow trout within said mating pair is homozygous for the IPN resistance allele.

5. A method for obtaining gametes from rainbow trout having increased resistance to infectious pancreatic necrosis (IPN), said method comprising:
   a) providing an initial population of rainbow trout;
   b) obtaining a nucleic acid sample from at least one individual rainbow trout within said initial population;
   c) detecting in each of said nucleic acid samples the presence of at least one allele conferring IPN resistance ("IPN resistance allele") within the genome of said rainbow trout, wherein the at least one IPN resistance allele is an allele of at least one single nucleotide polymorphism (SNP) selected from the SNPs listed in the following table:

| SNP # | Name Affymetrix ID | SEQ ID NO: | GenBank Contig | Position in GenBank Contig | dbSNP ss-No (SS#) | IPN resistance allele | Non-IPN resistance allele |
|---|---|---|---|---|---|---|---|
| 1 | AX-89929954 | 1 | FR904293.1 | 1651243 | 1398298005 | C | A |
| 2 | AX-89918280 | 2 | FR904293.1 | 1353665 | 1399389616 | G | A |
| 4 | AX-89960828 | 4 | FR932837.1 | 3160 | 1399779599 | T | C ; | d) selecting a rainbow trout from said initial population based on the presence of the at least one IPN resistance allele in the nucleic acid samples; and
  e) isolating gametes from said selected trout.

6. The method according to claim 5, wherein said gametes are eggs.

7. The method according to claim 5, wherein said gametes are spermatozoa.

8. A method for obtaining rainbow trout having increased resistance to infectious pancreatic necrosis (IPN), said method comprising:
  a) providing an initial population of rainbow trout;
  b) obtaining a nucleic acid sample from at least one individual rainbow trout within said initial population;
  c) detecting in each of said nucleic acid samples the presence of at least one allele conferring IPN resistance ("IPN resistance allele") within the genome of said rainbow trout, wherein the at least one IPN resistance allele is an allele of at least one single nucleotide polymorphism (SNP) selected from the SNPs listed in the following table:

| SNP # | Name Affymetrix ID | SEQ ID NO: | GenBank Contig | Position in GenBank Contig | dbSNP ss-No (SS#) | IPN resistance allele | Non-IPN resistance allele |
|---|---|---|---|---|---|---|---|
| 1 | AX-89929954 | 1 | FR904293.1 | 1651243 | 1398298005 | C | A |
| 2 | AX-89918280 | 2 | FR904293.1 | 1353665 | 1399389616 | G | A |
| 4 | AX-89960828 | 4 | FR932837.1 | 3160 | 1399779599 | T | C ; | d) selecting a rainbow trout from said initial population based on the presence of the at least one IPN resistance allele in the nucleic acid samples;
  e) isolating gametes from said selected trout; and
  f) utilizing said isolated gametes to produce progeny rainbow trout comprising increased resistance to IPN.

9. The method according to claim 8, wherein said gametes are eggs.

10. The method according to claim 8, wherein said gametes are spermatozoa.

* * * * *

SEQUENCE LISTING

```
<160> NUMBER OF SEQ ID NOS: 299

<210> SEQ ID NO 1
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: C or A

<400> SEQUENCE: 1
gaaagaaaca gtgataggct tttagtgagc acatanattt gacacacagt tgtgtgaaaa    60
caaagcatgt g                                                         71

<210> SEQ ID NO 2
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 2
aatatatgcc ttatatcagg atcgctaacc acagancagg attacaattt aatacttgca    60
caatatacat a                                                         71

<210> SEQ ID NO 3
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or G
```

<400> SEQUENCE: 3
tccttgtatc gcagaactt taaatgtttg aatccntctt gatgttatgt gattggtgga    60
ttcaaataag t                                                       71

<210> SEQ ID NO 4
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 4
gatgcagggt tgcacagaac gttgatgcca gtagtnatgg catggctctc agtacaaact    60
catactgagt g                                                       71

<210> SEQ ID NO 5
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or T

<400> SEQUENCE: 5
gaatggcaat taatttcatg ctgaactaac tgaatnaaga aggaaatga ccccaaccct    60 ggttgcatac t                                                       71

<210> SEQ ID NO 6
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 6
ctcacattct tcaccttatt ggaatgcatg gaaagncgcc atgggaagct cactgcggtt    60
tcgaacctac g                                                       71

<210> SEQ ID NO 7
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 7
agtcaaaacc atgaaaaagc tgattttaga atgacntttg taacactctc catgatgacg    60
gttaatagaa g                                                       71

<210> SEQ ID NO 8
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or G

<400> SEQUENCE: 8
cgtgtcaata ttggaacgac taaatacgtg aatctntcag gacgggtgaa ctgagcacaa    60
atctagatca t                                                        71

<210> SEQ ID NO 9
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or C

<400> SEQUENCE: 9
agtccctccc ttagtggtat caaaccataa ctaatnattt cttcacaaat tatggaacaa    60
aaataaatcc c                                                        71

<210> SEQ ID NO 10
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 10
aaacggagtg ccgaagactc tgaactcaca gactcnctgc cgaaaaaaac gaaagtaatg    60
tcctcaactc t                                                        71

<210> SEQ ID NO 11
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or G

<400> SEQUENCE: 11
tgtaaattca taagtaaaga gaacacctgt ttaagnagag cacattatgc aaaacctcat    60
atggaaaacg t                                                        71

<210> SEQ ID NO 12
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or G

<400> SEQUENCE: 12
gcgtggacac atgagggacg ctgtgctccc tgtgtnctcc cagcaacacg aggtaattct    60
gcagaacaac c                                                        71

<210> SEQ ID NO 13
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)

<223> OTHER INFORMATION: A or G

<400> SEQUENCE: 13
aaaggaagaa gaatggtcag gagaggtaag gttggnagga attatgcttt tcaatgatct    60
ggtcctgcaa g    71

<210> SEQ ID NO 14
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or G

<400> SEQUENCE: 14
gcaataataa ccattgaaaa atatgctttg ggaatntctc cattctttcc ctagtccaat    60
atgtgttctt t    71

<210> SEQ ID NO 15
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or G

<400> SEQUENCE: 15
aggggcggtt agacacatgg gtgtggctag aaatgngggt tggtgacacc cactccttgg    60
cactcgatga t    71

<210> SEQ ID NO 16
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 16
cagccagctt tcgagtagca gggagaggac agtaantatt gacacagtgt aagcactagg    60
cagcactagg c    71

<210> SEQ ID NO 17
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 17
caatacaatg aggtgtaaat ggttgaattc actgtnggat aaagactgca ggacaggcca    60
gtaaaacatt t    71

<210> SEQ ID NO 18
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or G

<400> SEQUENCE: 18
gtcctctatg cctcctatga gttcttcgag gccatntgca gcgtgagtag ctgcctggac    60
cccatgctgt a                                                         71

<210> SEQ ID NO 19
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 19
attacttttg aatcacagct tcagcatata gccctngcta tagatacaat tcatacatca    60
agataatgac t                                                         71

<210> SEQ ID NO 20
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or C

<400> SEQUENCE: 20
tatagtagat aattgattca aatggcagtt gtattncact tttgtttttc tttacagtgg    60
tcagtgctat t                                                         71

<210> SEQ ID NO 21
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or C

<400> SEQUENCE: 21
cacacaaggt agatacacct gcagagcatg tttcgnaaat taataaggta agtctgaata    60
ccaaatactg a                                                         71

<210> SEQ ID NO 22
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 22
ctgttgttgg ccagattacc atcagtgcag ttgganttca ggccttatct ctgcctcaca    60
caacatcatc t                                                         71

<210> SEQ ID NO 23
<211> LENGTH: 71
<212> TYPE: DNA
<213> ORGANISM: Oncorhynchus mykiss
<220> FEATURE:

```
<221> NAME/KEY: misc_feature
<222> LOCATION: (36)..(36)
<223> OTHER INFORMATION: A or C

<400> SEQUENCE: 23
atgggtcgtg ttcatcaggc agaaaaatga cgtatnatgc cctaatgaac atgaccctgg    60
cattacctag a                                                         71

<210> SEQ ID NO 24
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or G

<400> SEQUENCE: 24 gaaccctag gctagatgtt caacctggcc tcaggncaat tctgaagatt tggtacgcaa     60
atatgttcgc c                                                         71

<210> SEQ ID NO 25
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or G

<400> SEQUENCE: 25
ctgttcattc tgtctgtttc agttggtgct ctgganagga gaaagccca cctgctgtga     60 gcccttatt g                                                          71

<210> SEQ ID NO 26
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or G

<400> SEQUENCE: 26
tcagcgtcct acagctaaac catacgatga aattanaaca ataaattcag tgtgatatcc    60
gttatggacc a                                                         71

<210> SEQ ID NO 27
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 27
aggtggcagg aaaagaata cctccagcca atcgcntgac atctgtccat tcaagctgca     60
gcgaatctga c                                                         71

<210> SEQ ID NO 28
<211> LENGTH: 71
<212> TYPE: DNA
<213> ORGANISM: Oncorhynchus mykiss
```

```
<220> FEATURE:
<221> NAME/KEY: misc_feature
<222> LOCATION: (36)..(36)
<223> OTHER INFORMATION: A or G

<400> SEQUENCE: 28
cacgtctctc caaaacgttt ccacttactt tcccangaag cctttcccgt tgggctgctc    60
cttcagccac t                                                        71

<210> SEQ ID NO 29
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 29
tccatagtgg ctaccagccc acatacgcac tgacanaatc acagacagac tgacagacag    60
cagcttgatc a                                                        71

<210> SEQ ID NO 30
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or G

<400> SEQUENCE: 30
atttgagaat cagatgcaga agagcaaggt tttccnagcc tgtggctatc ctccatacga    60
ttcaaccacc t                                                        71

<210> SEQ ID NO 31
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 31
taccgtacag ccctgctaaa ggaggaaaac aagggncatg atggtatgtc ttggggcttc    60
ctcagggccc a                                                        71

<210> SEQ ID NO 32
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or G

<400> SEQUENCE: 32
aaacaactct tcaagatgat gagtaacaac caaagncaga aattcccctt aaaataactg    60
aaaggaaaaa g                                                        71

<210> SEQ ID NO 33
<211> LENGTH: 71
<212> TYPE: DNA
```

```
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 33
gtgtttgtaa actggtaatt gaaattgtac tgatancaga tgatgtagaa ataaatgtgt    60
tttgatgtag g                                                        71

<210> SEQ ID NO 34
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: C or T

<400> SEQUENCE: 34
tacagaggag ctatgggctt catcctcatg tacganatct gcaatgaaga gtccttcaac    60
gctgtgcagg a                                                        71

<210> SEQ ID NO 35
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 35
ggccccatta ttttggcttc ttgtgtagca gacttngtag tgtgtaagga agccttgctg    60
gtcttgcaca g                                                        71

<210> SEQ ID NO 36
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 36
tctgctgagc tcccctgaaa gactgtgagt cacaanggtc atttatttac cttctctgct    60
tcactcaaca c                                                        71

<210> SEQ ID NO 37
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 37
actattcctc acatgctaca gaatagctag ggtaanagga tagtaacatt aaccataaca    60
ccaaagctaa t                                                        71

<210> SEQ ID NO 38
<211> LENGTH: 71
```

```
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or G

<400> SEQUENCE: 38
tccagtccca ctagtttggc tttgaagtcg cggatngtag actcgctctt gtatctcttc    60
tcagtcaggt c                                                         71

<210> SEQ ID NO 39
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 39
gtaaaggcta gcagaccctg ggaacattcc cctgcnctca gcctctctgc catggaggaa    60
atgctaaaag t                                                         71

<210> SEQ ID NO 40
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: C or T

<400> SEQUENCE: 40
ttttgaacag cacttatctc ttctctccag aggggnatat cacagagcat gaccaaaaag    60
ttagccagct a                                                         71

<210> SEQ ID NO 41
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 41
aagttgacct cttatgattt tattattggt ttgtgntgca agatgttctg tccaggtttc    60
aacttatagc c                                                         71

<210> SEQ ID NO 42
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or T

<400> SEQUENCE: 42
accaccacac ctgcctgagt catgtaagaa gattangcat ggtggatgga ggtgggaaga    60
caattaatgg t                                                         71

<210> SEQ ID NO 43
```

```
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 43
tggtcgtctg agccctatgt agtgaattca aacttncttg tctaagccaa gtatcaacct    60
gcaaacccaa g                                                        71

<210> SEQ ID NO 44
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 44
tccccttctg tgtgctcaag gtgtgaatat tttatngtta acttacttca ctcgtgtcct    60
gcagttagat g                                                        71

<210> SEQ ID NO 45
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 45
agcaggcagg ttgagacaag cctgcagggc caatanctgt cactatcata actcaagcca    60 acaataccca а                                                        71

<210> SEQ ID NO 46
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: C or A

<400> SEQUENCE: 46
cttgcttgcc atcacccgtc tggtccaagg gactanggtc aatataacct ccaatcttag    60
taacctacct c                                                        71

<210> SEQ ID NO 47
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 47
gcagacaccc tgggcagcgt tggagtgatc atctcngcca tcctgatgca gaagtatgac    60
ctgatgatcg c                                                        71
```

<210> SEQ ID NO 48
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or G

<400> SEQUENCE: 48
aactgggcta aaacgatggg acggtgtgcg aaaacnaact aaccctaacc agaaaattgt    60
atgctttgtt t                                                        71

<210> SEQ ID NO 49
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or T

<400> SEQUENCE: 49
accaccttca cattaacctt ctccatgaca aaacancccc aagcctgaac agccccctagc   60 cccttccact a                                                        71

<210> SEQ ID NO 50
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 50
gaagacacaa actcaacaag agcacaacaa cacagnctta aggtactgca attcctgctt    60
attttcataa a                                                        71

<210> SEQ ID NO 51
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 51
aaatgaaaag cgagaaagga cggaggtatt ttaaanatat ttaccatagt actcaccgaa    60
ggctgcagcc a                                                        71

<210> SEQ ID NO 52
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 52
gaaattgccc cttgattttg tcagtttagc gatcantata cacaaaataa ttaactaaag    60
gaacaaccat a                                                        71

<210> SEQ ID NO 53
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or T

<400> SEQUENCE: 53
aaaccacatg gtcttcctgc aactttgtgc caaatnagta gtttcacaat gaacgttgtg    60
aggtctgcag c    71

<210> SEQ ID NO 54
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or A

<400> SEQUENCE: 54
agacacacag cagactagac tgaggatgtg aaccantcct ccacttaatg caaatgcagg    60
gacacattca g    71

<210> SEQ ID NO 55
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or C

<400> SEQUENCE: 55
ctattcctgc ttaccgtagt tgaactggct gttggntttc tcacagttga tgatgttgaa    60
gcgatagggc a    71

<210> SEQ ID NO 56
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 56
ggtgtaagta cagactcttt gaaagcatgc aaatanaagt aaagacactg tcattccttt    60
aaatgttctt g    71

<210> SEQ ID NO 57
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: C or A

<400> SEQUENCE: 57
cttctttatt tgctatgatt attacttaat agtgcngatt gtatttgtca tccgtattga    60
ctgcagaact a    71

```
<210> SEQ ID NO 58
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or T

<400> SEQUENCE: 58
attgttcaag gacattatgc ttgtcctaca tattgncaat tgatgtcgt tctttaacat    60 ttataattga t                                                        71

<210> SEQ ID NO 59
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or G

<400> SEQUENCE: 59
aaaacttctt aagggacaag aaggaagttg aagttngggg tgggctagga agataaagag    60
ttgggggtgt g                                                        71

<210> SEQ ID NO 60
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 60
accaacacag agatgagacg tgccgagcgc aaggcnacca agaagaagct cccgctgaaa    60
cgagagatgg a                                                        71

<210> SEQ ID NO 61
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: C or A

<400> SEQUENCE: 61
ttaatctaac tcactctcca taacatcaca gaagtngatg tattcgatta taacaagctc    60
agggctgtca t                                                        71

<210> SEQ ID NO 62
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or C

<400> SEQUENCE: 62
ccctttacct agaatggtct gcagcgtgat gtcaangtgg ttattttgtc cattgttgcc    60
```
agtgataagc c                                                          71

<210> SEQ ID NO 63
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 63
tgcagaatgg acaactgaag agagatatgt cgcacntgag ggaaacaact ccgtgtctag      60
gccttctgaa g                                                          71

<210> SEQ ID NO 64
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: C or T

<400> SEQUENCE: 64
gttagtgaaa gccatttcag ggtaaaccct ccaggncgtc caatgtacca tagaagcaaa      60
acaatgataa t                                                          71

<210> SEQ ID NO 65
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 65
cccatctgtc agaaccttgc ccacagctgt ttcccnactc aatgaaaaca agctaacatc      60
ctgcaggttg a                                                          71

<210> SEQ ID NO 66
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or T

<400> SEQUENCE: 66
ggaatattcg aacggcttgt tgtccaatga gtcggnggcc ttaccaccac aaacccaag       60 gcctgaggca g                                                          71

<210> SEQ ID NO 67
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or G

<400> SEQUENCE: 67
ttaagagagt cacaaacatg aaaaactgtg atagtncaaa gaagatgaac gataggcttg      60
tggatagatt a                                                          71

<210> SEQ ID NO 68
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: C or T

<400> SEQUENCE: 68
tttatttcag catttagccc aatcctgcta agaacngtca gttaatcact aattaggaga     60
atatcaataa a                                                          71

<210> SEQ ID NO 69
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or G

<400> SEQUENCE: 69
ctcgaagtaa gaaatgaagc tgcaggtctg caggcngagt gctgtcagtg gaatataata     60
cccttaatag a                                                          71

<210> SEQ ID NO 70
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 70
gataaggatg caacagattt attttagttt tagatnatgc tttcagactg atttcggctc     60
ttaaaaagat a                                                          71

<210> SEQ ID NO 71
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 71
tctctgttca atatttagaa taaaaagctg acaaangtca cgtaatggac tggaaacagc     60
agacacatgg c                                                          71

<210> SEQ ID NO 72
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 72

```
ctataggtgg atgatatgat atggttgcag ctaganagtg acagctgcct accttgtaag    60
taccacctcg a                                                         71

<210> SEQ ID NO 73
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: C or T

<400> SEQUENCE: 73
gcgtttccag taaaacgacg tccccttcg ccctanattt aatgagcacg tagtctagat     60
ttttgtttaa c                                                         71

<210> SEQ ID NO 74
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or C

<400> SEQUENCE: 74
gcaggttttt gcagaaatca gttgctaata aagttnttct gtaaccattg tataagcagg    60
gtcaccatga c                                                         71

<210> SEQ ID NO 75
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or G

<400> SEQUENCE: 75
tttctcttaa tgcatcatcc ttgtgcgaaa tcatgntaag tacacaccgt taaagttagg    60
tgctttgtta c                                                         71

<210> SEQ ID NO 76
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 76
aaactaatga aaaacacaag agtgcctgca gtaacnctgt actaacgctg tactaacagt    60
acactctcag g                                                         71

<210> SEQ ID NO 77
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 77
```
ctgcagcaga tggaactata tctctagtgg ctgtgngtgg aggaggagat gtggtgaaga    60
ctgagcagac a                                                         71

<210> SEQ ID NO 78
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or T

<400> SEQUENCE: 78
cagaaaggaa aaatgtgtca aagttctaga tagtgngtgg aaagactcaa acaatgcagt    60
ttggaatgaa g                                                         71

<210> SEQ ID NO 79
<211> LENGTH: 71
<212> TYPE: DNA
<213> ORGANISM: Oncorhynchus mykiss

<400> SEQUENCE: 79
gaaagaaaca gtgataggct tttagtgagc acatacattt gacacacagt tgtgtgaaaa    60
caaagcatgt g                                                         71

<210> SEQ ID NO 80
<211> LENGTH: 71
<212> TYPE: DNA
<213> ORGANISM: Oncorhynchus mykiss

<400> SEQUENCE: 80
aatatatgcc ttatatcagg atcgctaacc acagagcagg attacaattt aatacttgca    60
caatatacat a                                                         71

<210> SEQ ID NO 81
<211> LENGTH: 71
<212> TYPE: DNA
<213> ORGANISM: Oncorhynchus mykiss

<400> SEQUENCE: 81
tccttgtatc gcagaacttt taaatgtttg aatccttctt gatgttatgt gattggtgga    60
ttcaaataag t                                                         71

<210> SEQ ID NO 82
<211> LENGTH: 71
<212> TYPE: DNA
<213> ORGANISM: Oncorhynchus mykiss

<400> SEQUENCE: 82
gatgcagggt tgcacagaac gttgatgcca gtagttatgg catggctctc agtacaaact    60
catactgagt g                                                         71

<210> SEQ ID NO 83
<211> LENGTH: 71
<212> TYPE: DNA
<213> ORGANISM: Oncorhynchus mykiss

<400> SEQUENCE: 83
gaatggcaat taatttcatg ctgaactaac tgaatgaaga aaggaaatga ccccaaccct    60

```
ggttgcatac t                                                           71

<210> SEQ ID NO 84
<211> LENGTH: 71
<212> TYPE: DNA
<213> ORGANISM: Oncorhynchus mykiss

<400> SEQUENCE: 84
ctcacattct tcaccttatt ggaatgcatg gaaaggcgcc atgggaagct cactgcggtt      60
tcgaacctac g                                                           71

<210> SEQ ID NO 85
<211> LENGTH: 71
<212> TYPE: DNA
<213> ORGANISM: Oncorhynchus mykiss

<400> SEQUENCE: 85
agtcaaaacc atgaaaaagc tgattttaga atgacgtttg taacactctc catgatgacg      60
gttaatagaa g                                                           71

<210> SEQ ID NO 86
<211> LENGTH: 71
<212> TYPE: DNA
<213> ORGANISM: Oncorhynchus mykiss

<400> SEQUENCE: 86
cgtgtcaata ttggaacgac taaatacgtg aatctatcag gacgggtgaa ctgagcacaa      60
atctagatca t                                                           71

<210> SEQ ID NO 87
<211> LENGTH: 71
<212> TYPE: DNA
<213> ORGANISM: Oncorhynchus mykiss

<400> SEQUENCE: 87
agtccctccc ttagtggtat caaaccataa ctaataattt cttcacaaat tatggaacaa      60
aaataaatcc c                                                           71

<210> SEQ ID NO 88
<211> LENGTH: 71
<212> TYPE: DNA
<213> ORGANISM: Oncorhynchus mykiss

<400> SEQUENCE: 88
aaacggagtg ccgaagactc tgaactcaca gactctctgc cgaaaaaaac gaaagtaatg      60
tcctcaactc t                                                           71

<210> SEQ ID NO 89
<211> LENGTH: 71
<212> TYPE: DNA
<213> ORGANISM: Oncorhynchus mykiss

<400> SEQUENCE: 89
tgtaaattca taagtaaaga gaacacctgt ttaagaagag cacattatgc aaaacctcat      60
atggaaaacg t                                                           71

<210> SEQ ID NO 90
<211> LENGTH: 71
<212> TYPE: DNA
<213> ORGANISM: Oncorhynchus mykiss
```

```
<400> SEQUENCE: 90
gcgtggacac atgagggacg ctgtgctccc tgtgttctcc cagcaacacg aggtaattct    60
gcagaacaac c                                                        71

<210> SEQ ID NO 91
<211> LENGTH: 71
<212> TYPE: DNA
<213> ORGANISM: Oncorhynchus mykiss

<400> SEQUENCE: 91
aaaggaagaa gaatggtcag gagaggtaag gttggaagga attatgcttt tcaatgatct    60
ggtcctgcaa g                                                        71

<210> SEQ ID NO 92
<211> LENGTH: 71
<212> TYPE: DNA
<213> ORGANISM: Oncorhynchus mykiss

<400> SEQUENCE: 92
gcaataataa ccattgaaaa atatgctttg ggaatatctc cattctttcc ctagtccaat    60
atgtgttctt t                                                        71

<210> SEQ ID NO 93
<211> LENGTH: 71
<212> TYPE: DNA
<213> ORGANISM: Oncorhynchus mykiss

<400> SEQUENCE: 93
aggggcggtt agacacatgg gtgtggctag aaatgagggt tggtgacacc cactccttgg    60
cactcgatga t                                                        71

<210> SEQ ID NO 94
<211> LENGTH: 71
<212> TYPE: DNA
<213> ORGANISM: Oncorhynchus mykiss

<400> SEQUENCE: 94
cagccagctt tcgagtagca gggagaggac agtaagtatt gacacagtgt aagcactagg    60
cagcactagg c                                                        71

<210> SEQ ID NO 95
<211> LENGTH: 71
<212> TYPE: DNA
<213> ORGANISM: Oncorhynchus mykiss

<400> SEQUENCE: 95
caatacaatg aggtgtaaat ggttgaattc actgttggat aaagactgca ggacaggcca    60
gtaaaacatt t                                                        71

<210> SEQ ID NO 96
<211> LENGTH: 71
<212> TYPE: DNA
<213> ORGANISM: Oncorhynchus mykiss

<400> SEQUENCE: 96
gtcctctatg cctcctatga gttcttcgag gccatttgca gcgtgagtag ctgcctggac    60
cccatgctgt a                                                        71
```

<210> SEQ ID NO 97
<211> LENGTH: 71
<212> TYPE: DNA
<213> ORGANISM: Oncorhynchus mykiss

<400> SEQUENCE: 97 attactttg aatcacagct tcagcatata gcccttgcta tagatacaat tcatacatca     60
agataatgac t                                                         71

<210> SEQ ID NO 98
<211> LENGTH: 71
<212> TYPE: DNA
<213> ORGANISM: Oncorhynchus mykiss

<400> SEQUENCE: 98
tatagtagat aattgattca aatggcagtt gtattacact tttgtttttc tttacagtgg     60
tcagtgctat t                                                         71

<210> SEQ ID NO 99
<211> LENGTH: 71
<212> TYPE: DNA
<213> ORGANISM: Oncorhynchus mykiss

<400> SEQUENCE: 99
cacacaaggt agatacacct gcagagcatg tttcgaaaat taataaggta agtctgaata     60
ccaaatactg a                                                         71

<210> SEQ ID NO 100
<211> LENGTH: 71
<212> TYPE: DNA
<213> ORGANISM: Oncorhynchus mykiss

<400> SEQUENCE: 100
ctgttgttgg ccagattacc atcagtgcag ttggagttca ggccttatct ctgcctcaca     60
caacatcatc t                                                         71

<210> SEQ ID NO 101
<211> LENGTH: 71
<212> TYPE: DNA
<213> ORGANISM: Oncorhynchus mykiss

<400> SEQUENCE: 101
atgggtcgtg ttcatcaggc agaaaaatga cgtataatgc cctaatgaac atgaccctgg     60
cattacctag a                                                         71

<210> SEQ ID NO 102
<211> LENGTH: 71
<212> TYPE: DNA
<213> ORGANISM: Oncorhynchus mykiss

<400> SEQUENCE: 102
gaacccctag gctagatgtt caacctggcc tcaggtcaat tctgaagatt tggtacgcaa     60
atatgttcgc c                                                         71

<210> SEQ ID NO 103
<211> LENGTH: 71
<212> TYPE: DNA
<213> ORGANISM: Oncorhynchus mykiss

<400> SEQUENCE: 103

```
ctgttcattc tgtctgtttc agttggtgct ctggatagga gaaaagccca cctgctgtga    60 gcccttatt g                                                          71

<210> SEQ ID NO 104
<211> LENGTH: 71
<212> TYPE: DNA
<213> ORGANISM: Oncorhynchus mykiss

<400> SEQUENCE: 104
tcagcgtcct acagctaaac catacgatga aattaaaaca ataaattcag tgtgatatcc    60
gttatggacc a                                                         71

<210> SEQ ID NO 105
<211> LENGTH: 71
<212> TYPE: DNA
<213> ORGANISM: Oncorhynchus mykiss

<400> SEQUENCE: 105
aggtggcagg aaaaagaata cctccagcca atcgcgtgac atctgtccat tcaagctgca    60
gcgaatctga c                                                         71

<210> SEQ ID NO 106
<211> LENGTH: 71
<212> TYPE: DNA
<213> ORGANISM: Oncorhynchus mykiss

<400> SEQUENCE: 106
cacgtctctc caaaacgttt ccacttactt tcccaagaag cctttcccgt tgggctgctc    60
cttcagccac t                                                         71

<210> SEQ ID NO 107
<211> LENGTH: 71
<212> TYPE: DNA
<213> ORGANISM: Oncorhynchus mykiss

<400> SEQUENCE: 107
tccatagtgg ctaccagccc acatacgcac tgacataatc acagacagac tgacagacag    60
cagcttgatc a                                                         71

<210> SEQ ID NO 108
<211> LENGTH: 71
<212> TYPE: DNA
<213> ORGANISM: Oncorhynchus mykiss

<400> SEQUENCE: 108
atttgagaat cagatgcaga agagcaaggt tttccaagcc tgtggctatc ctccatacga    60
ttcaaccacc t                                                         71

<210> SEQ ID NO 109
<211> LENGTH: 71
<212> TYPE: DNA
<213> ORGANISM: Oncorhynchus mykiss

<400> SEQUENCE: 109
taccgtacag ccctgctaaa ggaggaaaac aaggggcatg atggtatgtc ttgggcttc     60 ctcagggccc a                                                         71

<210> SEQ ID NO 110
```

-continued

```
<211> LENGTH: 71
<212> TYPE: DNA
<213> ORGANISM: Oncorhynchus mykiss

<400> SEQUENCE: 110
aaacaactct tcaagatgat gagtaacaac caaagtcaga aattccccctt aaaataactg      60 aaaggaaaaa g                                                          71

<210> SEQ ID NO 111
<211> LENGTH: 71
<212> TYPE: DNA
<213> ORGANISM: Oncorhynchus mykiss

<400> SEQUENCE: 111
gtgtttgtaa actggtaatt gaaattgtac tgatatcaga tgatgtagaa ataaatgtgt      60
tttgatgtag g                                                          71

<210> SEQ ID NO 112
<211> LENGTH: 71
<212> TYPE: DNA
<213> ORGANISM: Oncorhynchus mykiss

<400> SEQUENCE: 112
tacagaggag ctatgggctt catcctcatg tacgacatct gcaatgaaga gtccttcaac      60
gctgtgcagg a                                                          71

<210> SEQ ID NO 113
<211> LENGTH: 71
<212> TYPE: DNA
<213> ORGANISM: Oncorhynchus mykiss

<400> SEQUENCE: 113
ggccccatta ttttggcttc ttgtgtagca gactttgtag tgtgtaagga agccttgctg      60
gtcttgcaca g                                                          71

<210> SEQ ID NO 114
<211> LENGTH: 71
<212> TYPE: DNA
<213> ORGANISM: Oncorhynchus mykiss

<400> SEQUENCE: 114
tctgctgagc tccctgaaa gactgtgagt cacaatggtc atttatttac cttctctgct      60
tcactcaaca c                                                          71

<210> SEQ ID NO 115
<211> LENGTH: 71
<212> TYPE: DNA
<213> ORGANISM: Oncorhynchus mykiss

<400> SEQUENCE: 115
actattcctc acatgctaca gaatagctag ggtaagagga tagtaacatt aaccataaca      60
ccaaagctaa t                                                          71

<210> SEQ ID NO 116
<211> LENGTH: 71
<212> TYPE: DNA
<213> ORGANISM: Oncorhynchus mykiss

<400> SEQUENCE: 116
tccagtccca ctagtttggc tttgaagtcg cggatagtag actcgctctt gtatctcttc      60
```
tcagtcaggt c                                                          71

<210> SEQ ID NO 117
<211> LENGTH: 71
<212> TYPE: DNA
<213> ORGANISM: Oncorhynchus mykiss

<400> SEQUENCE: 117
gtaaaggcta gcagaccctg ggaacattcc cctgcgctca gcctctctgc catggaggaa     60
atgctaaaag t                                                          71

<210> SEQ ID NO 118
<211> LENGTH: 71
<212> TYPE: DNA
<213> ORGANISM: Oncorhynchus mykiss

<400> SEQUENCE: 118
ttttgaacag cacttatctc ttctctccag aggggcatat cacagagcat gaccaaaaag     60
ttagccagct a                                                          71

<210> SEQ ID NO 119
<211> LENGTH: 71
<212> TYPE: DNA
<213> ORGANISM: Oncorhynchus mykiss

<400> SEQUENCE: 119
aagttgacct cttatgattt tattattggt ttgtggtgca agatgttctg tccaggtttc     60
aacttatagc c                                                          71

<210> SEQ ID NO 120
<211> LENGTH: 71
<212> TYPE: DNA
<213> ORGANISM: Oncorhynchus mykiss

<400> SEQUENCE: 120
accaccacac ctgcctgagt catgtaagaa gattaggcat ggtggatgga ggtgggaaga     60
caattaatgg t                                                          71

<210> SEQ ID NO 121
<211> LENGTH: 71
<212> TYPE: DNA
<213> ORGANISM: Oncorhynchus mykiss

<400> SEQUENCE: 121
tggtcgtctg agccctatgt agtgaattca aactttcttg tctaagccaa gtatcaacct     60
gcaaacccaa g                                                          71

<210> SEQ ID NO 122
<211> LENGTH: 71
<212> TYPE: DNA
<213> ORGANISM: Oncorhynchus mykiss

<400> SEQUENCE: 122
tccccttctg tgtgctcaag gtgtgaatat tttattgtta acttacttca ctcgtgtcct     60
gcagttagat g                                                          71

<210> SEQ ID NO 123
<211> LENGTH: 71
<212> TYPE: DNA

<213> ORGANISM: Oncorhynchus mykiss

<400> SEQUENCE: 123

| agcaggcagg ttgagacaag cctgcagggc caatatctgt cactatcata actcaagcca | 60 |
| acaatacccc a | 71 |

<210> SEQ ID NO 124
<211> LENGTH: 71
<212> TYPE: DNA
<213> ORGANISM: Oncorhynchus mykiss

<400> SEQUENCE: 124

| cttgcttgcc atcacccgtc tggtccaagg gactacggtc aatataacct ccaatcttag | 60 |
| taacctacct c | 71 |

<210> SEQ ID NO 125
<211> LENGTH: 71
<212> TYPE: DNA
<213> ORGANISM: Oncorhynchus mykiss

<400> SEQUENCE: 125

| gcagacaccc tgggcagcgt tggagtgatc atctcggcca tcctgatgca gaagtatgac | 60 |
| ctgatgatcg c | 71 |

<210> SEQ ID NO 126
<211> LENGTH: 71
<212> TYPE: DNA
<213> ORGANISM: Oncorhynchus mykiss

<400> SEQUENCE: 126

| aactgggcta aaacgatggg acggtgtgcg aaaacaaact aaccctaacc agaaaattgt | 60 |
| atgctttgtt t | 71 |

<210> SEQ ID NO 127
<211> LENGTH: 71
<212> TYPE: DNA
<213> ORGANISM: Oncorhynchus mykiss

<400> SEQUENCE: 127

| accaccttca cattaacctt ctccatgaca aaacagcccc aagcctgaac agccctagc | 60 |
| cccttccact a | 71 |

<210> SEQ ID NO 128
<211> LENGTH: 71
<212> TYPE: DNA
<213> ORGANISM: Oncorhynchus mykiss

<400> SEQUENCE: 128

| gaagacacaa actcaacaag agcacaacaa cacaggctta aggtactgca attcctgctt | 60 |
| attttcataa a | 71 |

<210> SEQ ID NO 129
<211> LENGTH: 71
<212> TYPE: DNA
<213> ORGANISM: Oncorhynchus mykiss

<400> SEQUENCE: 129

| aaatgaaaag cgagaaagga cggaggtatt ttaaatatat ttaccatagt actcaccgaa | 60 |
| ggctgcagcc a | 71 |

<210> SEQ ID NO 130
<211> LENGTH: 71
<212> TYPE: DNA
<213> ORGANISM: Oncorhynchus mykiss

<400> SEQUENCE: 130
gaaattgccc cttgattttg tcagtttagc gatcagtata cacaaaataa ttaactaaag    60
gaacaaccat a                                                         71

<210> SEQ ID NO 131
<211> LENGTH: 71
<212> TYPE: DNA
<213> ORGANISM: Oncorhynchus mykiss

<400> SEQUENCE: 131
aaaccacatg gtcttcctgc aactttgtgc caaatgagta gtttcacaat gaacgttgtg    60
aggtctgcag c                                                         71

<210> SEQ ID NO 132
<211> LENGTH: 71
<212> TYPE: DNA
<213> ORGANISM: Oncorhynchus mykiss

<400> SEQUENCE: 132
agacacacag cagactagac tgaggatgtg aaccattcct ccacttaatg caaatgcagg    60
gacacattca g                                                         71

<210> SEQ ID NO 133
<211> LENGTH: 71
<212> TYPE: DNA
<213> ORGANISM: Oncorhynchus mykiss

<400> SEQUENCE: 133
ctattcctgc ttaccgtagt tgaactggct gttggatttc tcacagttga tgatgttgaa    60
gcgatagggc a                                                         71

<210> SEQ ID NO 134
<211> LENGTH: 71
<212> TYPE: DNA
<213> ORGANISM: Oncorhynchus mykiss

<400> SEQUENCE: 134
ggtgtaagta cagactcttt gaaagcatgc aaatagaagt aaagacactg tcattccttt    60
aaatgttctt g                                                         71

<210> SEQ ID NO 135
<211> LENGTH: 71
<212> TYPE: DNA
<213> ORGANISM: Oncorhynchus mykiss

<400> SEQUENCE: 135
cttctttatt tgctatgatt attacttaat agtgccgatt gtatttgtca tccgtattga    60
ctgcagaact a                                                         71

<210> SEQ ID NO 136
<211> LENGTH: 71
<212> TYPE: DNA
<213> ORGANISM: Oncorhynchus mykiss

<400> SEQUENCE: 136
attgttcaag gacattatgc ttgtcctaca tattggcaat ttgatgtcgt tctttaacat    60
ttataattga t    71

<210> SEQ ID NO 137
<211> LENGTH: 71
<212> TYPE: DNA
<213> ORGANISM: Oncorhynchus mykiss

<400> SEQUENCE: 137
aaaacttctt aagggacaag aaggaagttg aagtttgggg tgggctagga agataaagag    60
ttgggggtgt g    71

<210> SEQ ID NO 138
<211> LENGTH: 71
<212> TYPE: DNA
<213> ORGANISM: Oncorhynchus mykiss

<400> SEQUENCE: 138
accaacacag agatgagacg tgccgagcgc aaggctacca agaagaagct cccgctgaaa    60
cgagagatgg a    71

<210> SEQ ID NO 139
<211> LENGTH: 71
<212> TYPE: DNA
<213> ORGANISM: Oncorhynchus mykiss

<400> SEQUENCE: 139
ttaatctaac tcactctcca taacatcaca gaagtcgatg tattcgatta taacaagctc    60
agggctgtca t    71

<210> SEQ ID NO 140
<211> LENGTH: 71
<212> TYPE: DNA
<213> ORGANISM: Oncorhynchus mykiss

<400> SEQUENCE: 140
ccctttacct agaatggtct gcagcgtgat gtcaaagtgg ttattttgtc cattgttgcc    60
agtgataagc c    71

<210> SEQ ID NO 141
<211> LENGTH: 71
<212> TYPE: DNA
<213> ORGANISM: Oncorhynchus mykiss

<400> SEQUENCE: 141
tgcagaatgg acaactgaag agagatatgt cgcacgtgag ggaaacaact ccgtgtctag    60
gccttctgaa g    71

<210> SEQ ID NO 142
<211> LENGTH: 71
<212> TYPE: DNA
<213> ORGANISM: Oncorhynchus mykiss

<400> SEQUENCE: 142
gttagtgaaa gccatttcag ggtaaaccct ccaggccgtc caatgtacca tagaagcaaa    60
acaatgataa t    71

```
<210> SEQ ID NO 143
<211> LENGTH: 71
<212> TYPE: DNA
<213> ORGANISM: Oncorhynchus mykiss

<400> SEQUENCE: 143
cccatctgtc agaaccttgc ccacagctgt ttccctactc aatgaaaaca agctaacatc    60
ctgcaggttg a                                                         71

<210> SEQ ID NO 144
<211> LENGTH: 71
<212> TYPE: DNA
<213> ORGANISM: Oncorhynchus mykiss

<400> SEQUENCE: 144
ggaatattcg aacggcttgt tgtccaatga gtcggggggcc ttaccaccac aaaccccaag    60
gcctgaggca g                                                         71

<210> SEQ ID NO 145
<211> LENGTH: 71
<212> TYPE: DNA
<213> ORGANISM: Oncorhynchus mykiss

<400> SEQUENCE: 145
ttaagagagt cacaaacatg aaaaactgtg atagtacaaa gaagatgaac gataggcttg    60
tggatagatt a                                                         71

<210> SEQ ID NO 146
<211> LENGTH: 71
<212> TYPE: DNA
<213> ORGANISM: Oncorhynchus mykiss

<400> SEQUENCE: 146
tttatttcag catttagccc aatcctgcta agaaccgtca gttaatcact aattaggaga    60
atatcaataa a                                                         71

<210> SEQ ID NO 147
<211> LENGTH: 71
<212> TYPE: DNA
<213> ORGANISM: Oncorhynchus mykiss

<400> SEQUENCE: 147
ctcgaagtaa gaaatgaagc tgcaggtctg caggcagagt gctgtcagtg gaatataata    60
cccttaatag a                                                         71

<210> SEQ ID NO 148
<211> LENGTH: 71
<212> TYPE: DNA
<213> ORGANISM: Oncorhynchus mykiss

<400> SEQUENCE: 148
gataaggatg caacagattt attttagttt tagattatgc tttcagactg atttcggctc    60
ttaaaaagat a                                                         71

<210> SEQ ID NO 149
<211> LENGTH: 71
<212> TYPE: DNA
<213> ORGANISM: Oncorhynchus mykiss

<400> SEQUENCE: 149
```

```
tctctgttca atatttagaa taaaaagctg acaaatgtca cgtaatggac tggaaacagc    60
agacacatgg c                                                        71

<210> SEQ ID NO 150
<211> LENGTH: 71
<212> TYPE: DNA
<213> ORGANISM: Oncorhynchus mykiss

<400> SEQUENCE: 150
ctataggtgg atgatatgat atggttgcag ctagatagtg acagctgcct accttgtaag    60
taccacctcg a                                                        71

<210> SEQ ID NO 151
<211> LENGTH: 71
<212> TYPE: DNA
<213> ORGANISM: Oncorhynchus mykiss

<400> SEQUENCE: 151
gcgtttccag taaaacgacg tccccttcg ccctacattt aatgagcacg tagtctagat     60
ttttgtttaa c                                                        71

<210> SEQ ID NO 152
<211> LENGTH: 71
<212> TYPE: DNA
<213> ORGANISM: Oncorhynchus mykiss

<400> SEQUENCE: 152
gcaggttttt gcagaaatca gttgctaata aagttattct gtaaccattg tataagcagg    60
gtcaccatga c                                                        71

<210> SEQ ID NO 153
<211> LENGTH: 71
<212> TYPE: DNA
<213> ORGANISM: Oncorhynchus mykiss

<400> SEQUENCE: 153
tttctcttaa tgcatcatcc ttgtgcgaaa tcatgttaag tacacaccgt taaagttagg    60
tgctttgtta c                                                        71

<210> SEQ ID NO 154
<211> LENGTH: 71
<212> TYPE: DNA
<213> ORGANISM: Oncorhynchus mykiss

<400> SEQUENCE: 154
aaactaatga aaaacacaag agtgcctgca gtaacgctgt actaacgctg tactaacagt    60
acactctcag g                                                        71

<210> SEQ ID NO 155
<211> LENGTH: 71
<212> TYPE: DNA
<213> ORGANISM: Oncorhynchus mykiss

<400> SEQUENCE: 155
ctgcagcaga tggaactata tctctagtgg ctgtgggtgg aggaggagat gtggtgaaga    60
ctgagcagac a                                                        71

<210> SEQ ID NO 156
<211> LENGTH: 71
```

```
<212> TYPE: DNA
<213> ORGANISM: Oncorhynchus mykiss

<400> SEQUENCE: 156
cagaaaggaa aaatgtgtca aagttctaga tagtgggtgg aaagactcaa acaatgcagt      60
ttggaatgaa g                                                          71

<210> SEQ ID NO 157
<211> LENGTH: 30
<212> TYPE: DNA
<213> ORGANISM: Artificial Sequence
<220> FEATURE:
<223> OTHER INFORMATION: Forward PCT primer

<400> SEQUENCE: 157
acgttggatg tccacagtcc acatgctttg                                      30

<210> SEQ ID NO 158
<211> LENGTH: 30
<212> TYPE: DNA
<213> ORGANISM: Artificial Sequence
<220> FEATURE:
<223> OTHER INFORMATION: Reverse PCR primer

<400> SEQUENCE: 158
acgttggatg ggaaagaaac agtgataggc                                      30

<210> SEQ ID NO 159
<211> LENGTH: 20
<212> TYPE: DNA
<213> ORGANISM: Artificial Sequence
<220> FEATURE:
<223> OTHER INFORMATION: Extension primer

<400> SEQUENCE: 159
cacacaactg tgtgtcaaat                                                 20

<210> SEQ ID NO 160
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or T

<400> SEQUENCE: 160
ataatttact tttaagattt ctgaccggcc ttgttnttt tgcttatgtg ccattattgc       60
cggctagacc a                                                          71

<210> SEQ ID NO 161
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 161
taaagaacaa gaaaacagta cacatgcatt aactcnccat gttggtgttg gagaactcga     60
tacagagaca g                                                          71

<210> SEQ ID NO 162
```

```
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: C or T

<400> SEQUENCE: 162
ctcatggaga ggcatatctt gtcctatccc cataanggcc acctggtaat gagccgtgaa    60
acactagagc c                                                         71

<210> SEQ ID NO 163
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 163
ccatttagat tattcaacgg tgaaacatac acatcntgta aattactctc aggtaaccgg    60
acttgatttg t                                                         71

<210> SEQ ID NO 164
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or G

<400> SEQUENCE: 164
gtttgtagcc ccatctcact ggcttcttga aagtanaatt tattatgatt gtttaattat    60
aatagtgaat a                                                         71

<210> SEQ ID NO 165
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 165
atttcatgta ttggccaaca aacgaacttg taggcntacg tgccatggtt gtcacatttt    60
aataaaacat g                                                         71

<210> SEQ ID NO 166
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or T

<400> SEQUENCE: 166
cacagttata gcaacactta agtagaatgg aaatgntttc atttaatttt agtcagttgg    60
cattcagttg a                                                         71
```

```
<210> SEQ ID NO 167
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 167
agtctgcaga ccctacccag cctggtctcc caggcngtca cacagcagca cagggacttt      60
ctggatggct t                                                          71

<210> SEQ ID NO 168
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: C or T

<400> SEQUENCE: 168
atttcatgaa cctacacaaa tccagtgtca ggaaancctt ataaacttt gctcatgggt       60 gtggagatgt g                                                          71

<210> SEQ ID NO 169
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or C

<400> SEQUENCE: 169
atagggccaa gacagaagac agacatgaaa gtcctnctga cgggcaaaac atacagaccc      60
cacctggaga a                                                          71

<210> SEQ ID NO 170
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or T

<400> SEQUENCE: 170
ttcagttcag tcaaactggc tgtcgttggc gctgcnggac tagctggcac attcaatggg     60
aatcgtttgt c                                                          71

<210> SEQ ID NO 171
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 171
aaaggtcttg atggatattg tgagttatcg gtgtcntaag aaatcgccac ctcgcaaccc     60
atgcgacccc a                                                          71
```

<210> SEQ ID NO 172
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: C or T

<400> SEQUENCE: 172
actccaaagc caccacagtc tcctccagcc atggtncatc cctccagtag cccaaccaat    60
taccaaacag a                                                        71

<210> SEQ ID NO 173
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: C or A

<400> SEQUENCE: 173
acatgcgaca catggacaga ttaattagat tgggtnacaa cacattgtat tgcaaacatg    60
tgaagctata a                                                        71

<210> SEQ ID NO 174
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or G

<400> SEQUENCE: 174
ctctcattcc tcctattcat atgtatatac actggnctag ttagtgttat ggttgttatt    60
cactggcaat a                                                        71

<210> SEQ ID NO 175
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or C

<400> SEQUENCE: 175
caaacaaccc tggaagtcaa atcaagaggc aaggcnctgt gtttccttga aagccagagc    60
tgtttgtgtc c                                                        71

<210> SEQ ID NO 176
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 176
ggaccagtgt ttcatatcct gtggtgagct tcacangtca aatgtgatta atcataattg    60
aaatcaaatt a                                                        71

<210> SEQ ID NO 177
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 177
aagagaatat ttggaatagc attggcaaat acaccnagtg gggtggagct gcgtcagtag    60
tgcacagcac a                                                        71

<210> SEQ ID NO 178
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 178
gaaaatactg ttactgtaga atataatagt cataancctc tgatccaaat aattatgcat    60
aggtagtgtt c                                                        71

<210> SEQ ID NO 179
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 179
ctcaacataa ttaaatacca acaccaatgt aaatcnttct tcagaaacat tgagtaaata    60
tacctttact a                                                        71

<210> SEQ ID NO 180
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or T

<400> SEQUENCE: 180
agaaagcagg aagttcaggg gtcaactggg caaggncaat aagaggcatt tctaaccgtg    60
atcctgaacc c                                                        71

<210> SEQ ID NO 181
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 181
cgaatcaagc caaataaagc ggccacatct caaatntggt cagcctttgg aggagaacga    60
taaacggact t                                                          71

<210> SEQ ID NO 182
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or G

<400> SEQUENCE: 182
ccgcagatga catcactaca ctgcctgata cagcanagcg tgctttgcgg tgagttaaaa      60
aaataccatg g                                                          71

<210> SEQ ID NO 183
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 183
catgagctca agcacatctg cttctttctt cagggnaaaa aaatacaggg atccccaact      60
gcatttgatt t                                                          71

<210> SEQ ID NO 184
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or C

<400> SEQUENCE: 184
tgtagtctaa taatgagggg attagtgaaa actttnagtc agacctttgt ctttaaaaca      60
atagatttct g                                                          71

<210> SEQ ID NO 185
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 185
atgttggcat tgtaggtgtc atagcaacca ggaccnaatc cctgtaccaa acatgtgatt     60
aaaaacatat a                                                          71

<210> SEQ ID NO 186
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 186
ttacccggct aaggagcgct tcttcgcac ttggantata atgaaacctc aaactgtctc      60
atttaatatg c								71

<210> SEQ ID NO 187
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or G

<400> SEQUENCE: 187
ttgggacagt ttaacgttca cctcaggaat ccacancctt tcattttaag tttatttac		60 ttggcagagc a								71

<210> SEQ ID NO 188
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or T

<400> SEQUENCE: 188
caacaatgca acagaaatta gtgtgtgaca aaaatntgaa cggctgcttt gaaaattatt		60 atcaaggcag t								71

<210> SEQ ID NO 189
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or G

<400> SEQUENCE: 189
gtgcccttat cttaccgctg atcagtggca acccantagt ttttactaac tgaaaacacc		60 attgacattc t								71

<210> SEQ ID NO 190
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or A

<400> SEQUENCE: 190
actgcctggt tatgacacct gaaccctaca gagagngtgg ggctatagtt aaaatttact		60 cccctaaggt t								71

<210> SEQ ID NO 191
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: C or G

<400> SEQUENCE: 191

```
aggatcccat cccataatga atgggtctag ctatanattt atgaccagtt gttttccggg    60
tttatgacct c                                                         71
```

<210> SEQ ID NO 192
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 192

```
taaatagctt tgtggagtag attatgaatt gtattnatgc catatccact gttctgcaat    60
gactctccat a                                                         71
```

<210> SEQ ID NO 193
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or C

<400> SEQUENCE: 193

```
accctttgat gtgatttgct tctgagaaac atcatnattt attgatgctt ccattaaagt    60
agcatagatg t                                                         71
```

<210> SEQ ID NO 194
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 194

```
aaatcacagt gcagttatca caaaacatta tcttcngtgt tgtagcctaa ctagactata    60
cagctgtaaa a                                                         71
```

<210> SEQ ID NO 195
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or G

<400> SEQUENCE: 195

```
aagtttgtac cccaaatttc catttatgga atgganagtt taattgcatt tttggattga    60
tacagtaacc a                                                         71
```

<210> SEQ ID NO 196
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or T

<400> SEQUENCE: 196

```
gggttatgta taaatcgatg taattattat ttttgnttta aaaggtataa tattgtataa      60
cattgtaata a                                                           71

<210> SEQ ID NO 197
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or T

<400> SEQUENCE: 197
gatggcattc actatccttt aacaccacat cgtagntgat gtggcacaaa agcagtgctt      60
aaaaaataaa t                                                           71

<210> SEQ ID NO 198
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or C

<400> SEQUENCE: 198
cacacaaaaa ctattagccc atcgttggta tagtgncaaa atgttttaaa tgtcagcaat      60
caaattcaag a                                                           71

<210> SEQ ID NO 199
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or A

<400> SEQUENCE: 199
tcagtgacgg ctgtgaacat aaagggtata gttgcnttac tggtccacgt tcaaaaacca     60
gagttgagat t                                                           71

<210> SEQ ID NO 200
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or G

<400> SEQUENCE: 200
accaatttta tagtgacaca gaaaaatatc tagatntgat tctcaccaaa gagaccatat     60
tttgaaatag t                                                           71

<210> SEQ ID NO 201
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or T
```

<400> SEQUENCE: 201
ctcgatcttc tcaagtcaag tggccaatta aatatnaatc taaacacaac aatccagttt    60
gactagttgt t                                                          71

<210> SEQ ID NO 202
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 202
aggacacacg ctgggtgagc aacacacatc cccagncccc ctgagaaatc aggcttctta    60
caaggttata a                                                          71

<210> SEQ ID NO 203
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 203
ggggcctttg tcacacagaa agagatgaca tcagtngcaa gagaggccat cagtgtgttc    60
aaggactgga a                                                          71

<210> SEQ ID NO 204
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or A

<400> SEQUENCE: 204
ggaagtctag ggtggaaggg aggacattgt gcgggncgtt ccaccaattg agtaccttt    60 cagcagtcac t                                                          71

<210> SEQ ID NO 205
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or T

<400> SEQUENCE: 205
catctcaaaa ataagttaaa taaataaatt actatngtaa gtgccaaata aagtaacagg    60
gttgaatttt a                                                          71

<210> SEQ ID NO 206
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or G

<400> SEQUENCE: 206
tgtagattaa acaacaaagt cagattatct gagccntgtg tgccccaact tcaacaagga    60
gaccgtattg t                                                         71

<210> SEQ ID NO 207
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or G

<400> SEQUENCE: 207
ttatcaataa ttataatcaa tgactcacat cttgantatc tacagatgta gacttgtgat    60
tgagctactg t                                                         71

<210> SEQ ID NO 208
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 208
aacgacctca tactgggccg gaggatctcc ttctangagc tcaggggga aatagggtgt     60 gggaacttct c                                                         71

<210> SEQ ID NO 209
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or C

<400> SEQUENCE: 209
aacaatacac tcttgtcact tgcctttact gagaangtcg tggtggacac cagattccca    60
tgtgaaggag a                                                         71

<210> SEQ ID NO 210
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: C or G

<400> SEQUENCE: 210
aagtcattga ccttgctgcc ttggtcgtcc ctctcngtgg tggtgaacac gcgcgttttg    60
gactcctctg t                                                         71

<210> SEQ ID NO 211
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)

<223> OTHER INFORMATION: A or G

<400> SEQUENCE: 211
tgctgaagct ggacaaggag aacgccgtcg accgcncaga gcaggctgag accgacaaga    60
aggcagcaga g    71

<210> SEQ ID NO 212
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 212
gatcagctgg agaacatcta caaggacaat cccctngtga atctccatta tgccactttt    60
agccaacaac t    71

<210> SEQ ID NO 213
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: C or T

<400> SEQUENCE: 213
tatgagcagc tgaaaaacaa ttaaaatatt tttttncctg tgtttgagga aggggaagag    60
tggacccagg g    71

<210> SEQ ID NO 214
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or G

<400> SEQUENCE: 214
atatttcctt cctcacatcc ctggcaatta tagtanaatc tgagccataa caacatgacc    60
tggatagatg a    71

<210> SEQ ID NO 215
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or A

<400> SEQUENCE: 215
aaataatggc atgcatttga tattagtgta tgtttnaaaa cattacaggt tacagagaaa    60
ctataaggaa t    71

<210> SEQ ID NO 216
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or G

<400> SEQUENCE: 216
acattcaggt aatggtacat tttgtttaat taaacnactt tccatagttt gtggagaaag    60
ggtgtgtact c                                                         71

<210> SEQ ID NO 217
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: C or T

<400> SEQUENCE: 217
ggttttatgc ttgaacattc attttggaat ttccangact gtctctagct gctttaatct    60
tctttcaagg a                                                         71

<210> SEQ ID NO 218
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 218
tagatgttga gtatatctaa cacttccaga acatcnagtt tagtgctgat gtgtcatttc    60
tgttccaggc a                                                         71

<210> SEQ ID NO 219
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or G

<400> SEQUENCE: 219
caatggaacg cctcctcttt ctaataaccc tagtanagtg ccgtcaaatg tcgttgacag    60
atttgagtct t                                                         71

<210> SEQ ID NO 220
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or A

<400> SEQUENCE: 220
aaaggatata ttgatgaata tgacctatgt actgtnctac ttaaattcag atagctgttt    60
gttcatgtgt g                                                         71

<210> SEQ ID NO 221
<211> LENGTH: 71
<212> TYPE: DNA
<213> ORGANISM: Oncorhynchus mykiss
<220> FEATURE:

<221> NAME/KEY: misc_feature
<222> LOCATION: (36)..(36)
<223> OTHER INFORMATION: A or G

<400> SEQUENCE: 221
gctatattaa ttcagaaatg ccattttctg tcatgnggga aaatatagtt ttacacttat    60
cccagaaaca c    71

<210> SEQ ID NO 222
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or G

<400> SEQUENCE: 222
tgtacattgt aaagatggag aaatattgac aaaaanatgt cgtataggct actgtattac    60
ttgatatgtt t    71

<210> SEQ ID NO 223
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or G

<400> SEQUENCE: 223
tttaacccag cattgtgaca catttttatt aaatcnagga tgtgcagttt gttttatcca    60
cttcattaat a    71

<210> SEQ ID NO 224
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or G

<400> SEQUENCE: 224
aatttgacca atttgtcttc atacatttca gataanctca cgattcttaa gtcatgttgt    60
atttttaccg a    71

<210> SEQ ID NO 225
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 225
cctgactgaa agcagggcac aatatcagga agttgnatta gccaccatca tggcggtgga    60
aaattgtgct t    71

<210> SEQ ID NO 226
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: A or G

<400> SEQUENCE: 226
gttatggtga aagagaagct cagttacgga gcacancagc aaatcctcaa caagccaaac    60
ctgcaagaca a                                                        71

<210> SEQ ID NO 227
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: T or C

<400> SEQUENCE: 227
gacatctgga gagctaagga aacaaccaag cctgtnggaa cttctattgg gtgtctctgc    60
tagcagtcca a                                                        71

<210> SEQ ID NO 228
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: G or T

<400> SEQUENCE: 228
caataactag aaaaatacat ttcctaaaga aaatgngtgt gcttgcttgc ttgtcttaaa    60
gtatttatgt t                                                        71

<210> SEQ ID NO 229
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: C or T

<400> SEQUENCE: 229
tatcaggaca agctggaact agatagctgg ttatgnaacg ttaactattg ggatcagaaa    60
ctgaactagc t                                                        71

<210> SEQ ID NO 230
<211> LENGTH: 71
<212> TYPE: DNA
<213> ORGANISM: Oncorhynchus mykiss

<400> SEQUENCE: 230
ataatttact tttaagattt ctgaccggcc ttgttgtttt tgcttatgtg ccattattgc    60
cggctagacc a                                                        71

<210> SEQ ID NO 231
<211> LENGTH: 71
<212> TYPE: DNA
<213> ORGANISM: Oncorhynchus mykiss

<400> SEQUENCE: 231

```
taaagaacaa gaaacagta cacatgcatt aactcgccat gttggtgttg gagaactcga        60
tacagagaca g                                                           71

<210> SEQ ID NO 232
<211> LENGTH: 71
<212> TYPE: DNA
<213> ORGANISM: Oncorhynchus mykiss

<400> SEQUENCE: 232
ctcatggaga ggcatatctt gtcctatccc cataacggcc acctggtaat gagccgtgaa        60
acactagagc c                                                           71

<210> SEQ ID NO 233
<211> LENGTH: 71
<212> TYPE: DNA
<213> ORGANISM: Oncorhynchus mykiss

<400> SEQUENCE: 233
ccatttagat tattcaacgg tgaaacatac acatcttgta aattactctc aggtaaccgg        60
acttgatttg t                                                           71

<210> SEQ ID NO 234
<211> LENGTH: 71
<212> TYPE: DNA
<213> ORGANISM: Oncorhynchus mykiss

<400> SEQUENCE: 234
gtttgtagcc ccatctcact ggcttcttga agtataatt tattatgatt gtttaattat        60
aatagtgaat a                                                           71

<210> SEQ ID NO 235
<211> LENGTH: 71
<212> TYPE: DNA
<213> ORGANISM: Oncorhynchus mykiss

<400> SEQUENCE: 235
atttcatgta ttggccaaca aacgaacttg taggcttacg tgccatggtt gtcacatttt        60
aataaaacat g                                                           71

<210> SEQ ID NO 236
<211> LENGTH: 71
<212> TYPE: DNA
<213> ORGANISM: Oncorhynchus mykiss

<400> SEQUENCE: 236
cacagttata gcaacactta agtagaatgg aaatggtttc atttaatttt agtcagttgg        60
cattcagttg a                                                           71

<210> SEQ ID NO 237
<211> LENGTH: 71
<212> TYPE: DNA
<213> ORGANISM: Oncorhynchus mykiss

<400> SEQUENCE: 237
agtctgcaga ccctacccag cctggtctcc caggctgtca cacagcagca cagggacttt        60
ctggatggct t                                                           71

<210> SEQ ID NO 238
<211> LENGTH: 71
```

<212> TYPE: DNA
<213> ORGANISM: Oncorhynchus mykiss

<400> SEQUENCE: 238
atttcatgaa cctacacaaa tccagtgtca ggaaaccctt ataaactttt gctcatgggt    60
gtggagatgt g                                                        71

<210> SEQ ID NO 239
<211> LENGTH: 71
<212> TYPE: DNA
<213> ORGANISM: Oncorhynchus mykiss

<400> SEQUENCE: 239
atagggccaa gacagaagac agacatgaaa gtcctgctga cgggcaaaac atacagaccc    60
cacctggaga a                                                        71

<210> SEQ ID NO 240
<211> LENGTH: 71
<212> TYPE: DNA
<213> ORGANISM: Oncorhynchus mykiss

<400> SEQUENCE: 240
ttcagttcag tcaaactggc tgtcgttggc gctgcaggac tagctggcac attcaatggg    60
aatcgtttgt c                                                        71

<210> SEQ ID NO 241
<211> LENGTH: 71
<212> TYPE: DNA
<213> ORGANISM: Oncorhynchus mykiss

<400> SEQUENCE: 241
aaaggtcttg atggatattg tgagttatcg gtgtcgtaag aaatcgccac ctcgcaaccc    60
atgcgacccc a                                                        71

<210> SEQ ID NO 242
<211> LENGTH: 71
<212> TYPE: DNA
<213> ORGANISM: Oncorhynchus mykiss

<400> SEQUENCE: 242
actccaaagc caccacagtc tcctccagcc atggtccatc cctccagtag cccaaccaat    60
taccaaacag a                                                        71

<210> SEQ ID NO 243
<211> LENGTH: 71
<212> TYPE: DNA
<213> ORGANISM: Oncorhynchus mykiss

<400> SEQUENCE: 243
acatgcgaca catggacaga ttaattagat tgggtcacaa cacattgtat tgcaaacatg    60
tgaagctata a                                                        71

<210> SEQ ID NO 244
<211> LENGTH: 71
<212> TYPE: DNA
<213> ORGANISM: Oncorhynchus mykiss

<400> SEQUENCE: 244
ctctcattcc tcctattcat atgtatatac actggactag ttagtgttat ggttgttatt    60
cactggcaat a                                                          71

<210> SEQ ID NO 245
<211> LENGTH: 71
<212> TYPE: DNA
<213> ORGANISM: Oncorhynchus mykiss

<400> SEQUENCE: 245
caaacaaccc tggaagtcaa atcaagaggc aaggcactgt gtttccttga aagccagagc     60
tgtttgtgtc c                                                          71

<210> SEQ ID NO 246
<211> LENGTH: 71
<212> TYPE: DNA
<213> ORGANISM: Oncorhynchus mykiss

<400> SEQUENCE: 246
ggaccagtgt ttcatatcct gtggtgagct tcacaggtca aatgtgatta atcataattg     60
aaatcaaatt a                                                          71

<210> SEQ ID NO 247
<211> LENGTH: 71
<212> TYPE: DNA
<213> ORGANISM: Oncorhynchus mykiss

<400> SEQUENCE: 247
aagagaatat ttggaatagc attggcaaat acacctagtg gggtggagct gcgtcagtag     60
tgcacagcac a                                                          71

<210> SEQ ID NO 248
<211> LENGTH: 71
<212> TYPE: DNA
<213> ORGANISM: Oncorhynchus mykiss

<400> SEQUENCE: 248
gaaaatactg ttactgtaga atataatagt cataatcctc tgatccaaat aattatgcat     60
aggtagtgtt c                                                          71

<210> SEQ ID NO 249
<211> LENGTH: 71
<212> TYPE: DNA
<213> ORGANISM: Oncorhynchus mykiss

<400> SEQUENCE: 249
ctcaacataa ttaaatacca acaccaatgt aaatcgttct tcagaaacat tgagtaaata     60
tacctttact a                                                          71

<210> SEQ ID NO 250
<211> LENGTH: 71
<212> TYPE: DNA
<213> ORGANISM: Oncorhynchus mykiss

<400> SEQUENCE: 250
agaaagcagg aagttcaggg gtcaactggg caagggcaat aagaggcatt tctaaccgtg     60
atcctgaacc c                                                          71

<210> SEQ ID NO 251
<211> LENGTH: 71
<212> TYPE: DNA
<213> ORGANISM: Oncorhynchus mykiss

<400> SEQUENCE: 251
cgaatcaagc caaataaagc ggccacatct caaatttggt cagcctttgg aggagaacga    60
taaacggact t                                                         71

<210> SEQ ID NO 252
<211> LENGTH: 71
<212> TYPE: DNA
<213> ORGANISM: Oncorhynchus mykiss

<400> SEQUENCE: 252
ccgcagatga catcactaca ctgcctgata cagcaaagcg tgctttgcgg tgagttaaaa    60
aaataccatg g                                                         71

<210> SEQ ID NO 253
<211> LENGTH: 71
<212> TYPE: DNA
<213> ORGANISM: Oncorhynchus mykiss

<400> SEQUENCE: 253
catgagctca agcacatctg cttctttctt caggggaaaa aaatacaggg atccccaact    60
gcatttgatt t                                                         71

<210> SEQ ID NO 254
<211> LENGTH: 71
<212> TYPE: DNA
<213> ORGANISM: Oncorhynchus mykiss

<400> SEQUENCE: 254
tgtagtctaa taatgagggg attagtgaaa actttaagtc agacctttgt ctttaaaaca    60
atagatttct g                                                         71

<210> SEQ ID NO 255
<211> LENGTH: 71
<212> TYPE: DNA
<213> ORGANISM: Oncorhynchus mykiss

<400> SEQUENCE: 255
atgttggcat tgtaggtgtc atagcaacca ggacctaatc cctgtaccaa acatgtgatt    60
aaaaacatat a                                                         71

<210> SEQ ID NO 256
<211> LENGTH: 71
<212> TYPE: DNA
<213> ORGANISM: Oncorhynchus mykiss

<400> SEQUENCE: 256
ttacccggct aaggagcgct ttcttcgcac ttggagtata atgaaacctc aaactgtctc    60
atttaatatg c                                                         71

<210> SEQ ID NO 257
<211> LENGTH: 71
<212> TYPE: DNA
<213> ORGANISM: Oncorhynchus mykiss

<400> SEQUENCE: 257
ttgggacagt ttaacgttca cctcaggaat ccacatcctt tcattttaag tttattttac    60
ttggcagagc a                                                         71

<210> SEQ ID NO 258
<211> LENGTH: 71
<212> TYPE: DNA
<213> ORGANISM: Oncorhynchus mykiss

<400> SEQUENCE: 258
caacaatgca acagaaatta gtgtgtgaca aaaatatgaa cggctgcttt gaaaattatt      60
atcaaggcag t                                                          71

<210> SEQ ID NO 259
<211> LENGTH: 71
<212> TYPE: DNA
<213> ORGANISM: Oncorhynchus mykiss

<400> SEQUENCE: 259
gtgcccttat cttaccgctg atcagtggca acccattagt ttttactaac tgaaaacacc      60
attgacattc t                                                          71

<210> SEQ ID NO 260
<211> LENGTH: 71
<212> TYPE: DNA
<213> ORGANISM: Oncorhynchus mykiss

<400> SEQUENCE: 260
actgcctggt tatgacacct gaaccctaca gagagtgtgg ggctatagtt aaaatttact      60
cccctaaggt t                                                          71

<210> SEQ ID NO 261
<211> LENGTH: 71
<212> TYPE: DNA
<213> ORGANISM: Oncorhynchus mykiss

<400> SEQUENCE: 261
aggatcccat cccataatga atgggtctag ctatacattt atgaccagtt gttttccggg      60
tttatgacct c                                                          71

<210> SEQ ID NO 262
<211> LENGTH: 71
<212> TYPE: DNA
<213> ORGANISM: Oncorhynchus mykiss

<400> SEQUENCE: 262
taaatagctt tgtggagtag attatgaatt gtattgatgc catatccact gttctgcaat      60
gactctccat a                                                          71

<210> SEQ ID NO 263
<211> LENGTH: 71
<212> TYPE: DNA
<213> ORGANISM: Oncorhynchus mykiss

<400> SEQUENCE: 263 acccttttgat gtgatttgct tctgagaaac atcataattt attgatgctt ccattaaagt     60
agcatagatg t                                                          71

<210> SEQ ID NO 264
<211> LENGTH: 71
<212> TYPE: DNA
<213> ORGANISM: Oncorhynchus mykiss

<400> SEQUENCE: 264

```
aaatcacagt gcagttatca caaaacatta tcttctgtgt tgtagcctaa ctagactata    60
cagctgtaaa a                                                         71

<210> SEQ ID NO 265
<211> LENGTH: 71
<212> TYPE: DNA
<213> ORGANISM: Oncorhynchus mykiss

<400> SEQUENCE: 265
aagtttgtac cccaaatttc catttatgga atggatagtt taattgcatt tttggattga    60
tacagtaacc a                                                         71

<210> SEQ ID NO 266
<211> LENGTH: 71
<212> TYPE: DNA
<213> ORGANISM: Oncorhynchus mykiss

<400> SEQUENCE: 266
gggttatgta taaatcgatg taattattat ttttgattta aaaggtataa tattgtataa    60
cattgtaata a                                                         71

<210> SEQ ID NO 267
<211> LENGTH: 71
<212> TYPE: DNA
<213> ORGANISM: Oncorhynchus mykiss

<400> SEQUENCE: 267
gatggcattc actatccttt aacaccacat cgtaggtgat gtggcacaaa agcagtgctt    60
aaaaaataaa t                                                         71

<210> SEQ ID NO 268
<211> LENGTH: 71
<212> TYPE: DNA
<213> ORGANISM: Oncorhynchus mykiss

<400> SEQUENCE: 268
cacacaaaaa ctattagccc atcgttggta tagtggcaaa atgttttaaa tgtcagcaat    60
caaattcaag a                                                         71

<210> SEQ ID NO 269
<211> LENGTH: 71
<212> TYPE: DNA
<213> ORGANISM: Oncorhynchus mykiss

<400> SEQUENCE: 269
tcagtgacgg ctgtgaacat aaagggtata gttgctttac tggtccacgt tcaaaaacca    60
gagttgagat t                                                         71

<210> SEQ ID NO 270
<211> LENGTH: 71
<212> TYPE: DNA
<213> ORGANISM: Oncorhynchus mykiss

<400> SEQUENCE: 270
accaatttta tagtgacaca gaaaaatatc tagatatgat tctcaccaaa gagaccatat    60
tttgaaatag t                                                         71

<210> SEQ ID NO 271
```

```
<211> LENGTH: 71
<212> TYPE: DNA
<213> ORGANISM: Oncorhynchus mykiss

<400> SEQUENCE: 271
ctcgatcttc tcaagtcaag tggccaatta aatatgaatc taaacacaac aatccagttt    60
gactagttgt t                                                          71

<210> SEQ ID NO 272
<211> LENGTH: 71
<212> TYPE: DNA
<213> ORGANISM: Oncorhynchus mykiss

<400> SEQUENCE: 272
aggacacacg ctgggtgagc aacacacatc cccagtcccc ctgagaaatc aggcttctta    60
caaggttata a                                                          71

<210> SEQ ID NO 273
<211> LENGTH: 71
<212> TYPE: DNA
<213> ORGANISM: Oncorhynchus mykiss

<400> SEQUENCE: 273
ggggcctttg tcacacagaa agagatgaca tcagttgcaa gagaggccat cagtgtgttc    60
aaggactgga a                                                          71

<210> SEQ ID NO 274
<211> LENGTH: 71
<212> TYPE: DNA
<213> ORGANISM: Oncorhynchus mykiss

<400> SEQUENCE: 274
ggaagtctag ggtggaaggg aggacattgt gcgggtcgtt ccaccaattg agtacctttt    60
cagcagtcac t                                                          71

<210> SEQ ID NO 275
<211> LENGTH: 71
<212> TYPE: DNA
<213> ORGANISM: Oncorhynchus mykiss

<400> SEQUENCE: 275
catctcaaaa ataagttaaa taaataaatt actatagtaa gtgccaaata aagtaacagg    60
gttgaatttt a                                                          71

<210> SEQ ID NO 276
<211> LENGTH: 71
<212> TYPE: DNA
<213> ORGANISM: Oncorhynchus mykiss

<400> SEQUENCE: 276
tgtagattaa acaacaaagt cagattatct gagccttgtg tgccccaact tcaacaagga    60
gaccgtattg t                                                          71

<210> SEQ ID NO 277
<211> LENGTH: 71
<212> TYPE: DNA
<213> ORGANISM: Oncorhynchus mykiss

<400> SEQUENCE: 277
ttatcaataa tttataatcaa tgactcacat cttgaatatc tacagatgta gacttgtgat    60
```

```
<210> SEQ ID NO 278
<211> LENGTH: 71
<212> TYPE: DNA
<213> ORGANISM: Oncorhynchus mykiss

<400> SEQUENCE: 278
aacgacctca tactgggccg gaggatctcc ttctatgagc tcaggggga aatagggtgt    60 gggaacttct c                                                       71

<210> SEQ ID NO 279
<211> LENGTH: 71
<212> TYPE: DNA
<213> ORGANISM: Oncorhynchus mykiss

<400> SEQUENCE: 279
aacaatacac tcttgtcact tgcctttact gagaaagtcg tggtggacac cagattccca    60
tgtgaaggag a                                                        71

<210> SEQ ID NO 280
<211> LENGTH: 71
<212> TYPE: DNA
<213> ORGANISM: Oncorhynchus mykiss

<400> SEQUENCE: 280
aagtcattga ccttgctgcc ttggtcgtcc ctctccgtgg tggtgaacac gcgcgttttg    60
gactcctctg t                                                        71

<210> SEQ ID NO 281
<211> LENGTH: 71
<212> TYPE: DNA
<213> ORGANISM: Oncorhynchus mykiss

<400> SEQUENCE: 281
tgctgaagct ggacaaggag aacgccgtcg accgcacaga gcaggctgag accgacaaga    60
aggcagcaga g                                                        71

<210> SEQ ID NO 282
<211> LENGTH: 71
<212> TYPE: DNA
<213> ORGANISM: Oncorhynchus mykiss

<400> SEQUENCE: 282
gatcagctgg agaacatcta caaggacaat ccctggtga atctccatta tgccactttt    60
agccaacaac t                                                        71

<210> SEQ ID NO 283
<211> LENGTH: 71
<212> TYPE: DNA
<213> ORGANISM: Oncorhynchus mykiss

<400> SEQUENCE: 283
tatgagcagc tgaaaaacaa ttaaaatatt tttttccctg tgtttgagga aggggaagag    60
tggacccagg g                                                        71

<210> SEQ ID NO 284
<211> LENGTH: 71
<212> TYPE: DNA
```
tgagctactg t                                                        71

<213> ORGANISM: Oncorhynchus mykiss

<400> SEQUENCE: 284

```
atatttcctt cctcacatcc ctggcaatta tagtataatc tgagccataa caacatgacc      60
tggatagatg a                                                          71
```

<210> SEQ ID NO 285
<211> LENGTH: 71
<212> TYPE: DNA
<213> ORGANISM: Oncorhynchus mykiss

<400> SEQUENCE: 285

```
aaataatggc atgcatttga tattagtgta tgttttaaaa cattacaggt tacagagaaa      60
ctataaggaa t                                                          71
```

<210> SEQ ID NO 286
<211> LENGTH: 71
<212> TYPE: DNA
<213> ORGANISM: Oncorhynchus mykiss

<400> SEQUENCE: 286

```
acattcaggt aatggtacat tttgtttaat taaacaactt tccatagttt gtggagaaag      60
ggtgtgtact c                                                          71
```

<210> SEQ ID NO 287
<211> LENGTH: 71
<212> TYPE: DNA
<213> ORGANISM: Oncorhynchus mykiss

<400> SEQUENCE: 287

```
ggttttatgc ttgaacattc attttggaat ttccacgact gtctctagct gctttaatct      60
tctttcaagg a                                                          71
```

<210> SEQ ID NO 288
<211> LENGTH: 71
<212> TYPE: DNA
<213> ORGANISM: Oncorhynchus mykiss

<400> SEQUENCE: 288

```
tagatgttga gtatatctaa cacttccaga acatctagtt tagtgctgat gtgtcatttc      60
tgttccaggc a                                                          71
```

<210> SEQ ID NO 289
<211> LENGTH: 71
<212> TYPE: DNA
<213> ORGANISM: Oncorhynchus mykiss

<400> SEQUENCE: 289

```
caatggaacg cctcctcttt ctaataaccc tagtaaagtg ccgtcaaatg tcgttgacag      60
atttgagtct t                                                          71
```

<210> SEQ ID NO 290
<211> LENGTH: 71
<212> TYPE: DNA
<213> ORGANISM: Oncorhynchus mykiss

<400> SEQUENCE: 290

```
aaaggatata ttgatgaata tgacctatgt actgtgctac ttaaattcag atagctgttt      60
gttcatgtgt g                                                          71
```

<210> SEQ ID NO 291
<211> LENGTH: 71
<212> TYPE: DNA
<213> ORGANISM: Oncorhynchus mykiss

<400> SEQUENCE: 291
gctatattaa ttcagaaatg ccattttctg tcatgaggga aaatatagtt ttacacttat   60
cccagaaaca c                                                        71

<210> SEQ ID NO 292
<211> LENGTH: 71
<212> TYPE: DNA
<213> ORGANISM: Oncorhynchus mykiss

<400> SEQUENCE: 292
tgtacattgt aaagatggag aaatattgac aaaaaaatgt cgtataggct actgtattac   60
ttgatatgtt t                                                        71

<210> SEQ ID NO 293
<211> LENGTH: 71
<212> TYPE: DNA
<213> ORGANISM: Oncorhynchus mykiss

<400> SEQUENCE: 293
tttaacccag cattgtgaca catttttatt aaatcaagga tgtgcagttt gttttatcca   60
cttcattaat a                                                        71

<210> SEQ ID NO 294
<211> LENGTH: 71
<212> TYPE: DNA
<213> ORGANISM: Oncorhynchus mykiss

<400> SEQUENCE: 294
aatttgacca atttgtcttc atacatttca gataaactca cgattcttaa gtcatgttgt   60 attttttaccg a                                                       71

<210> SEQ ID NO 295
<211> LENGTH: 71
<212> TYPE: DNA
<213> ORGANISM: Oncorhynchus mykiss

<400> SEQUENCE: 295
cctgactgaa agcagggcac aatatcagga agttgtatta gccaccatca tggcggtgga   60
aaattgtgct t                                                        71

<210> SEQ ID NO 296
<211> LENGTH: 71
<212> TYPE: DNA
<213> ORGANISM: Oncorhynchus mykiss

<400> SEQUENCE: 296
gttatggtga aagagaagct cagttacgga gcacaacagc aaatcctcaa caagccaaac   60
ctgcaagaca a                                                        71

<210> SEQ ID NO 297
<211> LENGTH: 71
<212> TYPE: DNA
<213> ORGANISM: Oncorhynchus mykiss

```
<400> SEQUENCE: 297
gacatctgga gagctaagga aacaaccaag cctgttggaa cttctattgg gtgtctctgc    60
tagcagtcca a                                                        71

<210> SEQ ID NO 298
<211> LENGTH: 71
<212> TYPE: DNA
<213> ORGANISM: Oncorhynchus mykiss

<400> SEQUENCE: 298
caataactag aaaaatacat ttcctaaaga aaatgggtgt gcttgcttgc ttgtcttaaa    60
gtatttatgt t                                                        71

<210> SEQ ID NO 299
<211> LENGTH: 71
<212> TYPE: DNA
<213> ORGANISM: Oncorhynchus mykiss

<400> SEQUENCE: 299
tatcaggaca agctggaact agatagctgg ttatgcaacg ttaactattg ggatcagaaa    60
ctgaactagc t                                                        71
```